(12) United States Patent
Cali et al.

(10) Patent No.: US 8,765,969 B2
(45) Date of Patent: *Jul. 1, 2014

(54) LUMINESCENCE-BASED METHODS AND PROBES FOR MEASURING CYTOCHROME P450 ACTIVITY

(75) Inventors: James J. Cali, Verona, WI (US); Dieter Klaubert, Arroyo Grande, CA (US); William Daily, Santa Maria, CA (US); Samuel K. Ho, New Bedford, MA (US); Susan Frackman, Madison, WI (US); Erika Hawkins, Pembroke (CA); Keith V. Wood, Mt. Horeb, WI (US)

(73) Assignee: Promega Corporation, Madison, WI (US)

( * ) Notice: Subject to any disclaimer, the term of this patent is extended or adjusted under 35 U.S.C. 154(b) by 148 days.

This patent is subject to a terminal disclaimer.

(21) Appl. No.: 12/217,374

(22) Filed: Jul. 3, 2008

(65) Prior Publication Data

US 2009/0023173 A1    Jan. 22, 2009

Related U.S. Application Data

(63) Continuation of application No. 10/665,314, filed on Sep. 19, 2003, now Pat. No. 7,692,022.

(60) Provisional application No. 60/412,254, filed on Sep. 20, 2002, provisional application No. 60/483,309, filed on Jun. 27, 2003.

(51) Int. Cl.
*C07D 417/04* (2006.01)

(52) U.S. Cl.
CPC ............................ *C07D 417/04* (2013.01)
USPC ..................................................... 548/178

(58) Field of Classification Search
USPC .................... 530/330, 331; 548/146, 178
See application file for complete search history.

(56) References Cited

U.S. PATENT DOCUMENTS

| | | |
|---|---|---|
| 4,612,302 A | 9/1986 | Szabo et al. |
| 4,655,022 A | 4/1987 | Natori |
| 4,665,022 A | 5/1987 | Schaeffer et al. |
| 4,684,620 A | 8/1987 | Hruby et al. |
| 4,826,989 A | 5/1989 | Batz et al. |
| 4,853,371 A | 8/1989 | Coy et al. |
| 4,992,531 A | 2/1991 | Patroni et al. |
| 5,035,999 A | 7/1991 | Geiger et al. |
| 5,098,828 A | 3/1992 | Geiger et al. |
| 5,114,704 A | 5/1992 | Spanier et al. |
| 5,283,179 A | 2/1994 | Wood |
| 5,283,180 A | 2/1994 | Zomer et al. |
| 5,290,684 A | 3/1994 | Kelly |
| 5,374,534 A | 12/1994 | Zomer et al. |
| 5,498,523 A | 3/1996 | Tabor et al. |
| 5,641,641 A | 6/1997 | Wood |
| 5,650,135 A | 7/1997 | Contag et al. |
| 5,650,289 A | 7/1997 | Wood |
| 5,726,041 A | 3/1998 | Chrespi et al. |
| 5,744,320 A | 4/1998 | Sherf et al. |
| 5,756,303 A | 5/1998 | Sato et al. |
| 5,780,287 A * | 7/1998 | Kraus et al. .................. 435/236 |
| 5,814,471 A | 9/1998 | Wood |
| 5,876,946 A | 3/1999 | Burbaum et al. |
| 5,976,825 A | 11/1999 | Hochman et al. |
| 6,143,492 A | 11/2000 | Makings et al. |
| 6,217,847 B1 | 4/2001 | Contag et al. |
| 6,291,164 B1 | 9/2001 | Blakesley |
| 6,299,858 B1 | 10/2001 | Serbedzija et al. |
| 6,376,208 B1 | 4/2002 | Kajiyama |
| 6,420,130 B1 | 7/2002 | Makings et al. |
| 6,514,687 B1 | 2/2003 | Makings et al. |
| 6,602,677 B1 | 8/2003 | Wood et al. |
| 6,638,713 B2 | 10/2003 | Makings et al. |
| 7,118,878 B1 | 10/2006 | Hawkins et al. |
| 7,524,876 B2 | 4/2009 | Takakura et al. |
| 7,692,022 B2 * | 4/2010 | Cali et al. ..................... 548/178 |
| 2002/0076777 A1 | 6/2002 | Merkulov et al. |
| 2003/0211560 A1 | 11/2003 | O'Brien et al. |
| 2003/0225036 A1 | 12/2003 | Kolesnikov et al. |
| 2003/0237103 A1 | 12/2003 | Jacob et al. |
| 2004/0146959 A1 | 7/2004 | Graham et al. |
| 2004/0171099 A1 | 9/2004 | Cali et al. |

(Continued)

FOREIGN PATENT DOCUMENTS

| | | |
|---|---|---|
| EP | 0411912 | 2/1991 |
| JP | 63-501571 | 6/1988 |

(Continued)

OTHER PUBLICATIONS

Farace et al., J. Clin. Chem. Clin. Biochem., vol. 28, No. 7, 1990.*

(Continued)

*Primary Examiner* — Alicia L Otton
(74) *Attorney, Agent, or Firm* — Michael Best & Friedrich LLP

(57) ABSTRACT

The invention provides compounds, compositions, methods, substrates, and kits useful for analyzing the metabolic activity in cells, tissue, and animals and for screening test compounds for their effect on cytochrome P450 activity. In particular, a one-step and two-step methods using luminogenic molecules, e.g. luciferins or coelenterazines, that are cytochrome P450 substrates and that are also bioluminescent enzyme, e.g., luciferase, pro-substrates are provided. The present method further provides a method for stabilizing and prolonging the luminescent signal in a luciferase-based assay using luciferase stabilizing agents such as reversible luciferase inhibitors.

4 Claims, 27 Drawing Sheets

(56) References Cited

U.S. PATENT DOCUMENTS

| | | | |
|---|---|---|---|
| 2004/0248225 | A1 | 12/2004 | Heindl et al. |
| 2005/0004103 | A1 | 1/2005 | Koshio et al. |
| 2005/0009098 | A1 | 1/2005 | Reymond et al. |
| 2005/0026171 | A1 | 2/2005 | Hawkins et al. |
| 2005/0118257 | A1 | 6/2005 | Bova |
| 2005/0153306 | A1 | 7/2005 | Harris |
| 2007/0015790 | A1 | 1/2007 | Cali et al. |
| 2007/0155806 | A1 | 7/2007 | Takakura et al. |
| 2008/0194522 | A1 | 8/2008 | Chen et al. |
| 2008/0299593 | A1 | 12/2008 | Cali et al. |
| 2010/0062470 | A1 | 3/2010 | Corona et al. |
| 2011/0003316 | A1 | 1/2011 | Cali et al. |

FOREIGN PATENT DOCUMENTS

| | | |
|---|---|---|
| JP | 01-502431 | 8/1989 |
| JP | 8-059686 | 3/1996 |
| JP | 2000-505-086 | 4/2000 |
| JP | 2000-270894 | 10/2000 |
| JP | 2002-080476 | 3/2002 |
| JP | 2006219381 | 8/2006 |
| RU | 2242471 | 12/2004 |
| WO | 87/02667 | 5/1987 |
| WO | 88/05434 | 7/1988 |
| WO | 96/31206 | 10/1996 |
| WO | 97/36885 | 10/1997 |
| WO | WO-99/60096 A2 | 11/1999 |
| WO | 00/16763 | 3/2000 |
| WO | WO-00/34506 A2 | 6/2000 |
| WO | WO-00/35900 A1 | 6/2000 |
| WO | WO-01/20002 A1 | 3/2001 |
| WO | WO-03/040100 A1 | 5/2003 |
| WO | WO-03/066611 A1 | 8/2003 |
| WO | 03/096980 | 11/2003 |
| WO | WO-2004/027378 A2 | 4/2004 |
| WO | WO-2006/130551 A2 | 12/2006 |
| WO | 2010/021686 | 2/2010 |

OTHER PUBLICATIONS

"U.S. Appl. No. 10/665,314, Notice of Allowance mailed May 15, 2009", 9 pgs.
"U.S. Appl. No. 10/665,314, Response filed Apr. 15, 2009 to Final Office Action mailed Jan. 15, 2009", 21 pgs.
"U.S. Appl. No. 11/444,145 Non-Final Office Action mailed Apr. 28, 2009", 15 pgs.
"U.S. Appl. No. 12/217,494, Preliminary Amendment filed Apr. 27, 2009", 20 pgs.
"Canadian Application Serial No. 2,497,560, Response filed Jul. 31, 2009 to Office Action mailed Feb. 3, 2009", 26 pgs.
"European Application Serial No. 08151520.7, Communication mailed on May 20, 2009", 2 pgs.
"International Application Serial No. PCT/US03/29078, International Preliminary Examination Report mailed Oct. 19, 2006", 4 pgs.
Carlile, D. J., et al., "In Vivo Clearance of Ethoxycoumarin and its Prediction from in vitro Systems", *Drug Metabolism and Disposition*,26(3), (1998), 216-221.
Markaglou, N., et al., "Immobilized enzyme reactors based upon the flavoenzymes monoamine oxidase A and B", *Journal of Chromatography B*, vol. 804, (2004), 295-302.
Stressor, D. M., et al., "Cytochrome P450 Flourometric Substrates:Identification of Drug and Isoform-Selective Probes for RAT CYP2D2 and Human CYP3A4", *Drug and Disposition*, 30(7), (2002), 845-852.
Japanese Patent Office Action for Application No. 2004-537859 dated Mar. 2, 2010 (18 pages) with translation.
"U.S. Appl. No. 10/665,314, Final Office Action mailed Jan. 15, 2009", 6 pgs.
"U.S. Appl. No. 11/444,145, Response filed Feb. 17, 2009 to Non-Final Office Action mailed Oct. 15, 2008", 33 pgs.
"Australian Application Serial No. 2003267245, Examiner's First Report mailed Nov. 29, 2006", 1 pg.
"Australian Application Serial No. 2003267245, Notice of Acceptance mailed Jun. 29, 2007", 3 pgs.
"Canadian Application Serial No. 2,497,560, Office Action mailed Feb. 3, 2009", 2 pgs.
"European Application Serial No. 03749715.3, Communication mailed Apr. 4, 2008", 6 pgs.
"European Application Serial No. 03749715.3, Response filed Jan. 30, 2009 to Communication mailed Apr. 4, 2008", 48 pgs.
"European Application Serial No. 03749715.3, Communication mailed on Feb. 24, 2009", 5 pgs.
"Japanese Application Serial No. 2004-537859, Appeal Brief mailed Dec. 3, 2008", 3 pgs.
"P450-Glo™ Assays", *Technical Bulletin No. 325*, Promega Corporation, Madison, WI, (Jun. 2003), 19 pgs.
Garrido-Hernandez, H., et al., "Design and Synthesis of Phosphotyrosine Peptidomimetic Prodrugs", *J. Med. Chem.*, 49, (2006), 3368-3376.
Beilstein Registry No. 1007132, Database Crossfire Beilstein, White, E.H. et al., J. Org. Chem. (1966) 31:1484-1488 (2 pages).
Benet, L.Z. et al., "Pharmacokinetics. The dynamics of drug absorption, distribution and elimination," Introduction and Chapter 1 of The Pharmacological Basis of Therapeutics, 9th Edition, McGraw-Hill (1996) 1-27.
Jiang, Y. et al., "*Crithidia fasciculata*: isolation, sequencing and expression of the hypoxanthine-guanine phosphoribosyltransferase gene," Exp. Parasitology (1996) 82:73-75.
Phillips, I.R. et al., "Preface: Cytochrome P450 protocols," Methods in Mol. Biol. (1998) 107:v-vi.
Salles, C. et al., "Biochemical characteristics of liver and brain monoamine oxidase from pacu," J. Fish Biol. (2001) 58:1301-1310.
Yun, B-S et al., "Coumarins with monamine oxidase inhibitory activity and antioxidative coumarino-lignans from *Hibiscus syriacus*," J. Natl. Prod. (2001) 64(9)1238-1240.
European Patent Office Examination Report for Application No. 06771475.8 dated Oct. 23, 2009 (3 pages).
Japanese Patent Office Action for Application No. 2004537859 dated Feb. 5, 2008 (8 pages) with translation.
United States Patent Office Action for U.S. Appl. No. 11/444,145 dated Dec. 3, 2009 (27 pages).
International Preliminary Report on Patentability for Application No. PCT/US06/020731 dated Sep. 12, 2007 (8 pages).
United States Patent Office Action for U.S. Appl. No. 12/217,494 dated Dec. 16, 2009 (18 pages).
Canadian Patent Office Action for Application No. 2,497,560, dated Dec. 21, 2009, 2 pages.
European Patent Office Action for Application No. 03749715.3 dated Jan. 20, 2010 (3 pages).
"5' Labelling—Fluorescein and Cyanine Dyes, Biotin", *Glen Report*, vol. 8, No. 2, http://www.glenres.com/GlenReports/GR8-2.pdf, (published online by Glen Research, Sterling, VA), (Dec. 1995), 8 pgs.
"U.S. Appl. No. 10/665,314, Response filed Jul. 24, 2006 to Restriction Requirement mailed Mar. 22, 2006", 37 pgs.
"U.S. Appl. No. 10/665,314, Advisory Action mailed Jun. 6, 2008", 3 pgs.
"U.S. Appl. No. 10/665,314, Final Office Action mailed Mar. 19, 2008", 5 pgs.
"U.S. Appl. No. 10/665,314, Response filed May 19, 2008 to Final Office Action mailed Mar. 19, 2008", 17 pgs.
"U.S. Appl. No. 10/665,314, Restriction Requirement mailed Mar. 22, 2006", 8 pgs.
"U.S. Appl. No. 10/665,314, Supplemental Response filed Jun. 19, 2008 to Advisory Action mailed Jun. 6, 2008", 18 pgs.
"U.S. Appl. No. 10/665,314, Non-Final Office Action mailed Oct. 11, 2007", 16 pgs.
"U.S. Appl. No. 10/665,314, Amendment and Response filed Jan. 10, 2008 to Office Action mailed Oct. 11, 2007", 39 pgs.
"U.S. Appl. No. 10/665,314, Non-Final Office Action mailed Jul. 18, 2008", 14 pgs.
"U.S. Appl. No. 10/665,314, Response filed Oct. 20, 2008 to Non Final Office Action mailed Jul. 18, 2008", 25 pgs.
"U.S. Appl. No. 11/444,145, Non-Final Office Action mailed Mar. 24, 2008", 16. pgs.

(56) References Cited

OTHER PUBLICATIONS

"U.S. Appl. No. 11/444,145, Response filed Oct. 11, 2007 to Restriction Requirement mailed Aug. 1, 2007", 25 pgs.
"U.S. Appl. No. 11/444,145, Non-Final Office Action Mailed Oct. 15, 2008", 16 pgs.
"U.S. Appl. No. 11/444,145, Preliminary Amendment mailed Aug. 22, 2006", 3 pgs.
"U.S. Appl. No. 11/444,145, Response filed Jun. 24, 2008 to Non Final Office Action mailed Mar. 24, 2008", 53 pgs.
"U.S. Appl. No. 11/444,145, Restriction Requirement mailed Aug. 1, 2007", 7 pgs.
"Beilstein Registry No. 1007132", *Database Crossfire Beilstein*, (White, E. H., et al., J. Org. Chem., vol. 31 (1966), 1484-1488, 2 pgs.
"Beilstein Registry No. 1034055", *Database Crossfire Beilstein*, (McCapra, F., et al., Chem. Commun. (1968), 22-23, 1 pg.
"Beilstein Registry No. 1041968", *Database Crossfire Beilstein*, (White, et al., Bioorg. Chem., vol. 1 (1971), 92-116), 2 pgs.
"Beilstein Registry No. 1119094", *Database Crossfire Beilstein*, (Benkoe, et al., Montsh. Chem., vol. 106 (1975), 1027-1032), 3 pgs.
"Beilstein Registry No. 1119095", *Database Crossfire Beilstein*, (Benkoe, A., et al., Monatsh. Chem., vol. 106 (1975), 1027-1032), 2 pgs.
"Beilstein Registry No. 1126922", *Database Crossfire Beilstein*, (Benkoe, et al., Monatsh. Chem., vol. 106, (1975), 1027-1032, 3 pgs.
"Beilstein Registry No. 1129927", *Database Crossfire Beilstein*, (Benkoe, et al., Monatsh. Chem., vol. 106 (1975), 1027-1032, 2 pgs.
"Beilstein Registry No. 30484", *Database Crossfire Beilstein*, (White, et al., J. Am. Chem. Soc., vol. 85 (1963), 337-343, 12 pgs.
"Beilstein Registry No. 3984932", *Database Crossfire Beilstein*, (White, et al., J. Org. Chem., vol. 30 (1965), 2344-2348, 2 pgs.
"Beilstein No. 4240164", *Database Crossfire Beilstein*, (Arness, R., et al., Carbohydr. Res., vol. 1, No. 1 (1990), 225-233, 2 pgs.
"Beilstein Registry No. 926292", *Database Crossfire Beilstein*, (White, et al., J. Org. Chem., vol. 30 (1965), 2344-2348, 2 pgs.
"Chemistry 2131: Organic Chemistry for the Life Sciences (3)", [online] [retrieved Dec. 17, 2004]. Retrieved from the Internet: <URL: http://www.mta.ca/~acockshu/c2131elimination.html>, (Mount Allison University),3 pgs.
"Database Accession No. 4240164", *Database Crossfire Beilstein* Beilstein Institute zur Foerderung der chemischen Wissenschaften, Frankfurt am Main, De, (1991), 2 pgs.
"Database Crossfire Beilstein Registry No. 179309", © 1988-2006, *Beilstein Institute zur foerderung der chemistein Wissenchaften*; 30, (1965), 2344-2348.
"European Application No. 03749715.3 Supplemental European Search Report mailed Jun. 14, 2007", 5 pgs.
"European Application Serial No. 06771475.8, Office Action mailed Jun. 12, 2008", (Feb. 13, 2008), 5 pgs.
"European Application Serial No. 06771475.8, Response filed Oct. 22, 2008 to Communication mailed Jun. 12, 2008", 22 pgs.
"European Application Serial No. 08151520.7, European Search Report mailed Jun. 5, 2008", 16 pgs.
"International Application Serial No. PCT/US03/29078, International Search Report mailed Oct. 8, 2004", 4 pgs.
"International Application Serial No. PCT/US2006/020731, International Search Report mailed Mar. 13, 2007", 8 pgs.
"International Application Serial No. PCT/US2006/020731, Partial International Search Report mailed Oct. 2, 2006", 5 pgs.
"International Application Serial No. PCT/US2006/020731, Written Opinion mailed Mar. 13, 2007", 9 pgs.
"Japanese Application Serial No. 2004-537859, Decision of Rejection mailed Aug. 5, 2008", (w/ English Translation),4 pgs.
"Japanese Application Serial No. 2004-537859, Demand for Appeal filed Nov. 4, 2008 Against Decision of Rejection mailed Aug. 5, 2008", (w/ English Translation),12 pgs.
Allen, T., et al., "Cloning and Expression of the Adenine Phophoribosyltransferase Gene from *Leishmania donovanin*", *Molecular and Biochemical Parasitology*, 74, (1995), 99-103.

Amess, R., et al., "Synthesis of luciferin glycosides as substrates for novel untrasensitive enzyme assays", *Carbohydrate Research*, 205, (1990),225-233.
Ben-Shlomo, Y., et al., "Using Monoamine Oxidase Type B Inhibitors in Parkinson's Disease", *BMJ*, vol. 329, (Sep. 11, 2004), 581-582.
Binda, C., et al., "Structure-Function Relationships in Flavoenzyme-Dependent Amine Oxidations—A Comparison of Polyamine Oxidase and Monoamine Oxidase", *The Journal of Biological Chemistry*, 277(27), (2002), 23973-23976.
Black, S. D., et al., "P-450 Cytochromes: Structure and Function", *Adv. Enzymol. Relat. Areas Mol. Biol.*, 60, (1987), 35-87.
Bowie, L. J., et al., "Synthesis of a New Substrate Analog of Firefly Luciferin.", *Biochemistry*. vol. 12(10), (1973), 1845-1852.
Branchini, B. R., et al., "Naphtyl- and Quinolylluciferin: Green and Red Light Emitting Firefly Luciferin Analogues", *Photochemistry and Photobiology*, 49(5), (1989), 689-695.
Charng, Y., et al., "Molecular Cloning and Expression of the Gene Encoding ADP-Glucose Pyrophosphorylase from the Cyanobacterium *Anabaena* sp. Strain PCC 7120", *Plant Molecular Biology*, 20, (1992),37-47.
Chen, K., et al., "R1, a Novel Repressor of the Human Monoamine Oxidase A", *The Journal of Biological Chemistry*, 280(12), (2005),11552-11559.
Craig, F. F., et al., "Membrane-permeable luciferin esters for assay of firefly luciferase in live intact cells", *Biochemical Journal*, 276(3), (1991),637-641.
Demir, B., et al., "Platelet Monoamine Oxidase Activity in Alcoholism Subtypes: Relationship to Personality Traits and Executive Functions", *Alcohol & Alcoholism*, 37(6), (2002),597-602.
Dukhovich, A., et al., "Time course of luciferyl adenylate synthesis in the firefly luciferase reaction", *FEBS Letters*, 395(2-3), (1996),188-190.
Eriksson, J., et al., "Method for Real Time Detection of Inorganic Pyrophosphatase Activity", *Analytical Biochemistry*, 293(1), (2001),67-70.
Farace, C., et al., "Synthesis and Characterization of a New Substrate of *Photinus pyralis* luciferase: 4-methyl-*D*-luciferin", *Journal of Clinical Chemistry and Clinical Biochemistry*, 28(7), (1990), 471-474.
Feldmann, R., et al., "Decreased Metabolism and Viability of Mycoplasma Hominis Induced by Monoclonal Antibody-Mediated Agglutination", *Infection and Immunitty*, 60(1), (1992),166-174.
Flickinger, B., "Using Metabolism Data in Early Development", *Drug Disc. Dev.*, 4(9)., (2001),53-56.
Gabelova, A., et al., "Mutagenicity of 7*H*-Dibenzo[c,g]Carbazole and its Tissue Specific Derivatives in Genetically Engineered Chinese Hamster V79 Cell Lines Stably Expressing Cytochrome P450", *Mutation Research*, 517, (2002),135-145.
Gandelman, O., et al., "Cytoplasmic factors that Affect the intensity and stability of Bioluminescence from firefly luciferase in living mammalian cells.", *Journal of Bioluminescence and Chemiluminescence*, 9(6), (1994),363-371.
Gomez-Lechon, M., et al., "Expression and Induction of a Large Set of Drug-Metabolizing Enzymes by the Highly Differentiated Human Heptoma Cell Line BC2", *Eur. J. Biochem.*, 268, (2001),1448-1459.
Graham-Lorence, S., et al., "P450s: Structural Similarities and Functional Differences", *The FASEB Journal*, 10, 206-214,(1996),206-214.
Guengerich, F. P., et al., "Common and Uncommon Cytochrome P-450 Reactions Related to Metabolism and Chemical Toxicity", *Chem. Res. Tox.*, 14(6), (2001),611-650.
Gutierrez, M. C., et al., "The First Fluorogenic Assay for Detecting a Baeyer-Villigerase Activity in Microbial Cells", *Org. Biomol. Chem.*, 1, (2003),3500-3506.
Hardman, J. G., et al., *Goodman & Gilman's The Pharmacological Basis of Therapeutics*, Ninth Edition, McGraw-Hill Companies, Inc., (1996), 1-27.
Hawkins, E. M., et al., "Coelenterazine derivatives for improved solution stability", *Luminescene*, 17, (Proceedings of the International Symposium on Bioluminescence And Chemiluminescence),(2002), 91-92.

(56) References Cited

OTHER PUBLICATIONS

Holt, A., "Imidazoline Binding Sites on Receptors and Enzymes: Emerging Targets for Novel Antidepressant Drugs?", *J. Psychiatry Neuorosci*, 28(6), (2003),409-414.

Hynson, R. M. G. et al., "Conformational Changes in Monoamine Oxidase A In Response to Ligand Binding or Reduction", *Biochimica et Biophysica Acta*, 1672, (2004),60-66.

Inouye, S. , et al., "The Use of *Renilla* Luciferase, *Oplophorus* Luciferase, and Apoaequorin as Bioluminscent Reporter Protein in the Presence of Coelenterazine Analogues as Substrate", *Biochemical and Biophysical Research Communications*, 233, (1997),349-353.

Jagadeeswaran, P., et al., "Nucleotide Sequence and Analysis of Deletion Mutants of the *Escherichia coli* gpt Gene in Plasmid pSV$_2$ gpt, Gene, 31," *Gene*, 31, (1996),309-313.

Jiang, Y., et al., "*Crithidia fasciculata*: Isolation, Sequencing, and Expression of the Hypoxanthine-Guanine Phosphoribosyltransferase Gene", *Experimental Parasitology*, 82, (1996), 73-75.

Kalmar, G., et al., "Cloning and Expression of Rat Liver CTP-:Phosphocholine Cytidlytransferase: An Ampipathetic Protein that Controls Phophatidylcholine Synthesis", *Proc. Natl. Acad. Sci USA*, 87, (1990), 6029-6033.

Katz, I. R., et al., "Monoamine Oxidase, an Intracellular Probe of Oxygen Pressure in Isolated Cardiac Myocytes", *The Journal of Biological Chemistry*, 259(12), (1984),7504-7509.

Kelly, J. H., et al., "A Fluorescent Cell-Based Assay for Cytochrome P-450 Isozyme 1A2 Induction and Inhibition", *Journal of Biomolecular Screening*, 5(4), (2000),249-253.

Kim, D.-J. , et al., "Molecular Cloning of Cucumber Phosphoenolpyruvate Carboxykinase and Developmental Regulation of Gene Expression", *Plant Molecular Biology*, 26, (1994),423-434.

Kim, J. J., et al., "Selective Enhancement of Emotional, But Not Motor, Learning in Monoamine Oxidase A-Deficient Mice", *Proc. Natl. Acad. Sci. USA*, 94, (May 1997), 5929-5933.

Ladror, U., et al., "Cloning, Sequencing, and Expression of Pyrophosphate-Dependent Phosphofructokinase from *Propionibacterium freudenreichii*", *The Journal of Biological Chemistry*, 266(25), (1991),16550-16555.

Leemann, T., et al., "Cytochrome P450TB (CYP2C): A Major Monooxygenase Catalyzing Diclofenac 4'-Hydroxylation in Human Liver", *Life Sci.*, 52(1), (1993),29-34.

Lembert, N., "Firefly luciferase can use L-luciferin to produce light", *Biochemical Journal*, 317( Pt 1), (Jul. 1, 1996),273-277.

Leyh, T. , et al., "The Sulfate Activation Locus of *Escherichia coli* K12: Cloning, Genetic, and Enzymatic Characterization", *The Journal of Biological Chemistry*, 263(5), (1988),2409-2416.

Ludin, K. M., et al., "The *ade4* Gene of *Schizosaccharomyces pombe*: Cloning, Sequence and Regulation", *Curr Genet*, 25, (1994), 465-468.

Mancy, A. , et al., "Diclofenac and Its Derivatives As Tools for Studying Human Cytochromes P450 Active Sites: Particular Efficiency and Regioselectivity of P450 2Cs", *Biochemistry*, 38, (1999),14264-14270.

Marolda, C., et al., "Identification, Expression, and DNA Sequence of the GDP-Mannose Biosynthesis Genes Encoded by the 07 *rfb* Gene Cluster of Strain VW187 (*Escherichia coli* 07:K1)", *Journal of Bacteriology*, 175(1), (1993),148-158.

Masuda-Nishimura, I., et al., "Development of a rapid positive/absent test for coliforms using sensitive bioluminescence assay", *Lett Appl Microbiol.*, 30(2), (2000),130-135.

Miller, V. P., et al., "Fluorometric High-Throughput Screening for Inhibitors of Cytochrome P450", *Ann. NY Acad. Sci.* 919, (2000),26-32.

Miska, W., et al., "A new type of ultrasensitive bioluminogenic enzyme substrates, I. Enzyme substrates with D-Luciferin as leaving group", *Biological Chemistry Hoppe-Seyler*, 369(5), (May 5, 1998),407-411.

Miska, W., et al., "Evaluation of the Bioluminescence-enchanced zona binding assay", *Bioluminescence And Chemiluminescence: Molecular Reporting with Photons*, Proceedings of the International Symposium on Bioluminescence and Chemiluminescence, (Oct. 4-8, 1996),315-318.

Miska, W, et al., "Synthesis and characterization of luciferin derivatives for use in bioluminescence enhanced enzyme immunoassays", *Journal of Clinical Chemistry and Clinical Biochemistry*, vol. 25, (1987),23-30.

Mitani, M., et al., "Chemiluminescent Assay of β-D-Galactosidase Using Cypridina Luciferin Analogue: 3-(β-D-Galactopyranosyloxy)-6-(4-methoxyphenyl)-2-methyl-imidazo[1,2-α]pyrazine", *Analytical Sciences*, 10(5), (1994), 813-814.

Monsees, T., et al., "A Novel Bioluminogenic Assay for Alpha-Chymotrypsin", *Journal of Bioluminescene and Chemiluminescence*; 10(4), (Jul. 1995),213-218.

Monsees, T., et al., "Synthesis and Characterization of a bioluminogenic substrate for α-chymotrypsin", *Analytic Biochemistry*; 222(2), (1994),329-334.

Müller-Röber, B., et al., "Isolation and Expression Analysis of cDNA Clones Encoding a Small and a Large Subunit of ADP-Glucose Pyrophosphorylase from Sugar Beet", *Plant Molecular Biology*, 27, (1995),191-197.

Nakagawa, S., et al., "Nucleotide Sequence of the FAD Synthetase Gene from *Corynebacterium ammoniagenes* and Its Expression in *Escherichia coil*", *Biosci. Biotech Biochem.*, 59(4), (1995), 694-702.

Nelson, D. R., et al., "P450 Superfamily: Update on New Sequences, Gene Mappin, Accession Nos. and Nomenclature", *Pharmacogenetics*, 6, (1996),1-42.

Nicolaus, B. J., "Symbiotic Approach to Drug Drug Design", *Decision Making in Drug Research*, (Jan. 1, 1983),173-186.

Phillips, I. R., et al., "Preface—Cytochrome P450 Protocols", *Methods in Mol. Biol.*, 107, (1998), pp. v-vi.

Pla, J., et al., "Cloning of the *Candida albicans* H1S1 Gene by Direct Complementation of a C. *Albicans* Histidine Auxotroph Using an Improved Double-ARS Shuttle Vector", *Gene*, 165, (1995), 115-120.

Rahman, A., et al., "Selective Biotransformation of Taxol to 6α-Hydroxytaxol by Human Cytochrome P450 2C8", *Cancer Res.*, 54(21), (1994),5543-5546.

Renwick, A. B., et al., "Evaluation of 7-benzyloxy-4-trifluoromethyl-coumarin, some other 7-hydroxy-4-trifluoro-methylcoumarin derivatives and 7-benzyloxyquinoline as fluorescent substrates for rat hepatic cytochrome P450 enzymes", *Xenobiotica*, vol. 31, No. 12,(2001),861-878.

Rose, A., et al., "A Phosphoribosylanthranilate in Transferase Gene Is Defective in Blue Fluorescent *Arabidopsis thaliana* Tryptophan Mutants", *Plant Physiol.*, 100, (1992), 582-592.

Sai, Y., et al., "Assessment of Specificity of Eight Chemical Inhibitors Using cDNA-Expressed Cytochromes P450", *Xenobiotica*, 30(4), (2000),327-343.

Shanmugam, K., et al., "Purification and Characterization of a tRNA Nucleotidyltransferase From Lupinus Albus and Functional Complementation of a Yeast Mutation by the Corresponding cDNA", *Plant Molecular Biology*, 30, (1996),281-295.

Shimomura, O., et al., "Semi-synthetic Aequorins with Improved Sensitivity to $Ca^{2+}$ Ions", *Biochem. J.*, 261, (1989), 913-920.

Shou, M., et al., "A Kinetic Model for the Metabolic Interaction of Two Substrates at the Active Site of Cytochrome P450 3A4", *J. Biol. Chem.*, 276(3), (2001), 2256-2262.

Sussman, H. E., et al., "Choosing the Best Reporter Assay", *The Scientist*, 15(15), [online]. Retrieved from the Internet: <URL: http://www.the-scientist.com/article/display/12529/ profile2_010723.html>, (Jul. 23, 2001), 25-27.

Tassaneeyakul, W. , et al., "Specificity of Substrate and Inhibitor Probes for Human Cytochromes P450 1A1 and 1A2", *J. Pharmacol. Exp. Ther.* 265(1), (1993),401-407.

Teranishi, K., "Coelenterazine analogs as chemiluminescent probe for superoxide anion", *Analytical Biochemistry*, 249(1), (Jun. 15, 1997),37-43.

Toya, Y., et al., "Improved synthetic methods of firefly luciferin derivatives for analysis use in bioluminescent analysis of hydrolytic

(56) References Cited

OTHER PUBLICATIONS enzymes; carboxylyic esterase and alkaline phosphatase", *Bulletin of the Chemical Society of Japan*, vol. 65(10), (1992),2604-2610.
Ubeaud, G., et al., "Estimation of flavin-containing monooxygenase activity in intake hapatoxyte monolayers or rat, hamster, rabbit, dog and human by using *N*-oxidation of benzidamine", *European Journal of Pharmaceutical Sciences*, vol. 8, (1999),255-260.
Van Vleet, T., et al., "Metabolism and Cytotoxicity of Aflatoxin B1 in Cytochrome P450 Expressing Human Lung Cells", *Journal of Toxicological and Environmental Health*, 65, (2002),853-867.
Vinitsky, A., et al., "Cloning and Nucleic Acid Sequence of the *Salmonella typhimurium pncB* Gene and Structur of Nicotnate Phosphoribosyltransferase", *Journal of Bacteriology*, 173(2), (1991),536-540.
Vonstein, V., et al., "Molecular Cloning of the *pyrE* Gene from the Extreme Thermophile *Thermus flavus*", *J. Bacterio*, 177(8), (1995), 4540-4543.
White, E. H., et al., "Analogs of Firefly Luciferin", *Journal of Organic Chemistry*, 30, (1965), 2344-2348.
White, E. H., et al., "Analogs of Firefly Luciferin, III", *Journal of Organic Chemistry*, 31, (1966),1484-1488.
Wood, K. A., "Engineering Luciferase enzymes and substrates for novel assay capabilities", *Proceedings of SPIE—Miscroarrays and Combinatorial Techniques: Design, Fabrication, And Analysis II*, 5328, (Jun. 2004), 69-77.
Wrighton, S. A., et al., "The Human Hepatic Cytochromes P450 Involved in Drug Metabolism", *Critical Reviews in Toxicology*, 22(1), (1992),1-21.
Yang, J., et al., "An Easily Synthesized Photolyzable Luciferase for In Vivo Luciferase Activity Measurement", *Biotechniques*, vol. 15(5), (1993), 848-850.
Yoshitomi, S., et al., "Establishment of the Transformants Expressing Human Cytochrome P450 Subtypes in HepG2, and their Applications on Drug Metabolism and Toxicology", *Toxicology in Vitro*, 15 (2001), 245-246.
Youdin, M. B., et al., "Novel Substrates and Products of Amine Oxidase-Catalysed Reactions", *Biochemical Society Transactions*, vol. 19, (1990), 224-228.
Yun, C-H., et al., "Rate-determining Steps in Phenacetin Oxidations by Human Cytochrome P450 1A2 and Selected Mutants", *Biochemistry*, 39, (2000), 11319-11329.
Zapata, G., et al., "Sequence of the Cloned *Escherichia coli* K1 CMP-*N*-Acetylneuraminic Acid Synthetase Gene", *The Jorunal of Biological Chemistry*, 264(25), (1989),14769-17774.
Zhou, M., et al., "A One-Step Fluorometric Method for the Continuous Measurement of Monoamine Oxidase Activity", *Analytical Biochemistry*, 253, (1997),169-174.
Zhou, M., et al., "A Stable Nonfluorescent Derivative of Resorufin for the Fluorometric Determination of Trace Hydrogen Peroxide: Applications in Detecting the Activity of Phagocyte NADPH Oxidase and Other Oxidases", *Analytical Biochemistry*, 253, (1997),162-168.
Zhou, W., et al., "New bioluminogenic substrates for monoamine oxidase assays", *Journal of the American Chemical Society*, 128 (10), (Mar. 15, 2006),3122-3123.
Zhou, G., et al., "Platelet Monoamine Oxidase B and Plasma β-Phenylethylamine in Parkinson's Disease",*J. Neurol. Neuorosurg. Psychiatry*, 70, (2001),229-231.
O'Brien, M.A. et al., "Homogeneous, bioluminescent protein assays: caspase-3 as a model," J. Biomol. Screen. (2005) 10(2):137-148.
Yang, X. et al., "Homogeneous enzyme immunoassay modified for application to luminescence-based biosensors," Anal. Biochem. (2005) 336:102-107.
United States Patent Office Action for U.S. Appl. No. 11/444,145 dated Jul. 20, 2010 (14 pages).
United States Patent Office Action for U.S. Appl. No. 12/217,494 dated Jun. 28, 2010 (10 pages).
"Amplex Red monoamine oxidase assay kit (A12214)," Molcular Probes (Oct. 1, 2004) 4 pages, retrieved from the Internet: http://probes.invitrogen.com/media/pis/mp12214.pdf.

Abyshev, A.Z. et al., "Preparation and antiviral effect of benzopyran-2-one derivatives," Khimiko-Farmatsevticheskii Zhurnal (1996) 30(7):17-19; Database CA Accession No. 125:237748.
Aparna, M.V.L. et al., "Synthesis and 5-HT2A antagonist activity of some 7-(3-aminopropoxy)-4-methyl-chromen-2-ones," Indian J. Pharm. Sci. (2005) 67(4):467-472; Database CA Accession No. 145:62752.
Shinde, N.D. et al., "Synthesis of some sulfonamido and amino alkanes and their antifungal activity," Asian J. Chem. (1996) 8(1):85-90, Database CA Accession No. 124:232194.
Wahler, d. et al., "Enzyme fingerprints of activity, and stereo- and anantionselectivity from fluorogenic and chromogenic substrate arrays," Chem. A European Journal. (2002) 8(14):3211-3228.
European Patent Office Action for Application No. 06771475.8 dated Dec. 14, 2010 (3 pages).
European Patent Office Action for Application No. 08151520.7 dated Dec. 17, 2010 (8 pages).
European Patent Office Extended Search Report for Application No. 10075500.8 dated Dec. 10, 2010 (8 pages).
European Patent Office Extended Search report for Application No. 10075501.6 dated Dec. 9, 2010 (5 pages).
European Patent Office Extended Search Report for Application No. 10075502.4 dated Dec. 17, 2010 (9 pages).
Takahashi, S. et al., "Benzimidazole N-oxide. VIII. The reactivity of ethyl 1-methy-2-benzimidazolecarboxylate 3-oxide and related compounds," Chem. Pharm. Bull. (1968) 16(3):527-538.
United States Patent Office Notice of Allowance for U.S. Appl. No. 11/444,145 dated Jan. 24, 2011 (19 pages).
United States Patent Office Notice of Allowance for U.S. Appl. No. 12/543,376 dated Jul. 9, 2012 (10 pages).
European Patent Office Action for Application No. 06771475.8 dated Oct. 18, 2011 (3 pages).
European Patent Office Action for Application No. 08151520.7 dated Dec. 1, 2011 (7 pages).
United States Patent Office Action for U.S. Appl. No. 12/217,494 dated Nov. 16, 2012 (3 pages).
European Patent Office Examination Report for Application No. 09789154.3 dated Nov. 14, 2012 (6 pages).
European Patent Office Action for Application No. 10075502.4 dated Dec. 14, 2012 (4 pages).
European Patent Office Action for Application No. 10075501.6 dated Dec. 21, 2012 (3 pages).
United States Patent Office Action for U.S. Appl. No. 12/217,494 dated Jan. 14, 2013 (3 pages).
European Patent Office Action for Application No. 08151520.7 dated Feb. 19, 2013 (8 pages).
United States Patent Office Notice of Allowance for U.S. Appl. No. 12/217,494 dated Feb. 21, 2013 (5 pages).
Ll, A.R, "Evaluation of luciferin-isopropyl acetal as a CYP3A4 substrate for human hepatocytes: effects of organic solvents, cytochrome P450 (P450) inhibitors, and P450 inducers," Drug Metabolism and Disposition (2009) 37(8):1598-1603.
International Search Report and Written Opinion for Application No. PCT/US2009/004696 dated Nov. 19, 2009 (13 pages).
Japanese Patent Office Action for Application No. 2008-146920 dated Jul. 7, 2011 (7 pages).
United States Patent Office Notice of Allowance for U.S. Appl. No. 12/754,164 dated Sep. 21, 2011 (5 pages).
Geiger, R. et al., "A new ultrasensitive bioluminogenic enzyme substrate for beta-galactosidase," Biol. Chem. Hoppe-Seyler (1992) 373:1187-1191.
White, E.H. et al., "Amino analogs of firefly luciferin and biological activity thereof," J. Amer. Chem.. Soc. (1966) 88 (9):2015-2018.
European Patent Office Action for Application No. 10075500.8 dated Jan. 11, 2012 (4 pages).
European Patent Office Action for Application No. 10075501.6 dated Jan. 11, 2012 (3 pages).
European Patent Office Action for Application No. 10075502.4 dated Jan. 11, 2012 (4 pages).
Japanese Patent Office Action for Application No. 2008-514754 dated Jan. 12, 2012 (12 pages) with English translation.
United States Patent Office Action for U.S. Appl. No. 12/217,494 dated Jan. 26, 2012 (14 pages).

(56) References Cited

OTHER PUBLICATIONS

United States Patent Office Action for U.S. Appl. No. 12/543,376 dated Jan. 26, 2012 (7 pages).
United States Patent Office Action for U.S. Appl. No. 12/754,164 dated May 13, 2011 (5 pages).
United States Patent Office Action for U.S. Appl. No. 12/217,494 dated Aug. 7, 2012 (9 pages).
Lee et al., "Synthesis of 7'-[123I]iodo-d-luciferin for in vivo studies of firefly luciferase gene expression," Bioorg. Med. Chem. Lett. 2004, v.14, pp. 1161-1163.
Cali et al., "Characterization of Human Sterol 27-Hydroxylase. A Mitochondrial Cytochrome P-450 That Catalyzes Multiple Oxidation Reactions in Bile Acid Biosynthesis," J. Biol. Chem., 266:12, 7774-7778 (1991).
Cali et al., "Screen for Cytochrome P450 Activity Using a Luminescent Assay," Cell Notes, I3 (2005) pp. 8-10.
Cali, "Bioluminescent P450 assays that use D-luciferin derivatives as substrates for CYPIAI. JA2. JBI, 2C8, 2C9, 2J2, 3A4, 3A7, 4AJ I, 4F3B. 4FI 2 and 19," Proc. 14th Int. Conf Cytochromes P450, Medimond Int. Proc. (2005).
Cali, "Screen for CYP450 Inhibitors Using P450-Glo™ Luminescent Cytochrome P450 Assays," Cell Notes.7: 2-4 (2003).
Chandran et al., "Latent Fluorophore Based on the Trimethyl Lock," J. Am. Chem. Soc., 127:1652-1653 (2005).
Ellis et al., "Evidence That Aspartic Acid 301 Is a Critical Substrate-Contact Residue in the Active Site of Cytochrome P450 2D6," J. Biol Chem., 270:49, 29055-29058 (1995).
Greene, T.W.; Wutz, P.G.M. "Protecting Groups in Organic Synthesis," 3rd edition, John Wiley & Sons, Inc., New York (1999).
Greenwald et al., "Controlled Release of Proteins from Their Poly(Ethylene Glycol) Conjugates: Drug Delivery Systems Employing 1,6-Elimination," Bioconjugate Chem., 14:395-403 (2003).
Greenwald et al., "Drug Delivery Systems Employing 1,4- or 1,6-Elimination: Poly(ethylene glycol) Prodrugs of Amine-Containing Compounds," J. Med. Chem., 42:3657-3667 (1999).
Huffman, et al., "Lithium Alkoxides of Cinchona Alkaloids as Chiral Controllers for Enantioselective Acetylide Addition to Cyclic N-Acyl Ketimines," J. Org. Chem. 1995, 60, 1590-1594.
International Union of Pure and Applied Chemistry, "Definitive Rules for Nomenclature of Organic Chemistry," J. Am. Chem. Soc. 1960, 82, 5566.
Mazeas et al., "Synthesis of New Melatoninergic Ligands Including Azaindole Moiety," Heterocycles, 50:1065-1080 (1999).
Paquette, Leo A.; "Principles of Modern Heterocyclic Chemistry," (W.A. Benjamin, New York, 1968).
Rendic, "Summary of Information on Human CYP Enzymes: Human P450 Metabolism Data," Drug Metab. Rev. 34: 83-448 (2002).
Sasson et al., "From Azides to Nitriles. A Novel Fast Transformation Made Possible by BrF3," Org Lett, 7:11, 2177-2179 (2005).
Shimada et al., "Oxidation of Xenobiotics by Recombinant Human Cytochrome P450 1B1," Drug Metab. Dispos., 29:5, 617-622 (1997).
Stevens et al., "Developmental Expression of the Major Human Hepatic CYP3A Enzymes," J. Pharm. Exp. Ther., 307:2, 573-582 (2003).
Takahashi et al., "Heteroaromatic N-Oxides. X. 1) Synthesis and Reactions of Benzothiazole 3-Oxide," Chem & Pharm. Bull., 18:6, 1176-1184 (1970).
Tucker, et al., "Synthesis of a Series of 4-(Arylethynyl)-6-chloro-4-cyclopropyl-3,4-dihydroquinazolilHn-)2-(o nes as Novel Non-nucleoside HIV-1 Reverse Transcriptase Inhibitors," J. Med. Chem. 1994, 37, 2437-2444.
Wang et al., "Synthesis of a Novel Esterase-Sensitive Cyclic Prodrug System for Peptides That Utilizes a "Trimethyl Lock"-Facilitated Lactonization Reaction," J. Org. Chem., 62:1363-1367 (1997).
Wei et al., "Activation of Antibacterial Prodrugs by Peptide Deformylase," Bioorg. Med. Chem. Lett., I0, 1073-1076 (2000).
Weissberger, "The Chemistry of Heterocyclic Compounds, A Series of Monographs," John Wiley & Sons, New York, 1950.
European Patent Office Action for Application No. 10075502.4 dated Dec. 16, 2013 (3 pages).

* cited by examiner

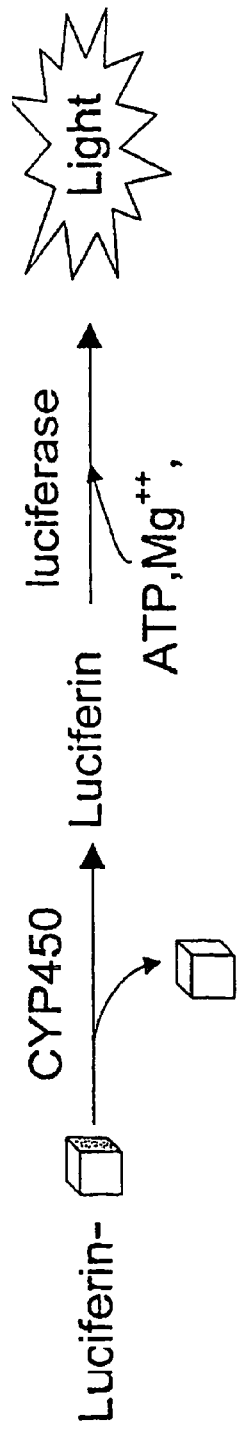
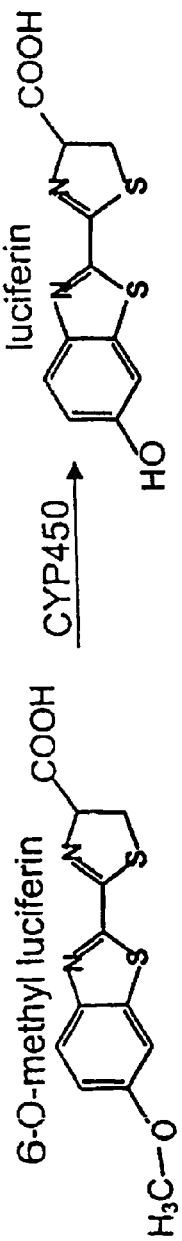
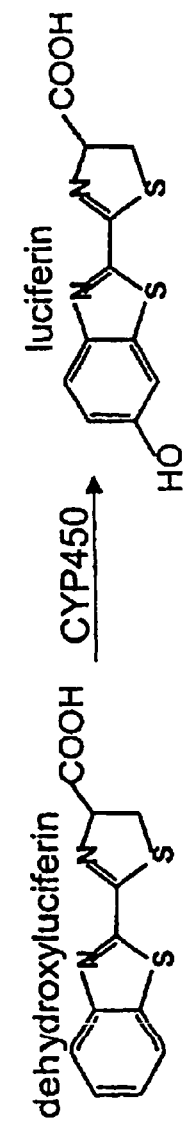
FIG. 1

D-luciferin and D-luciferin derivatives.

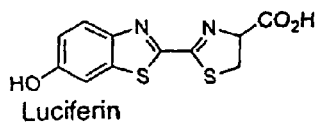
Luciferin

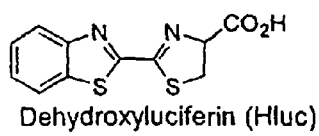
Dehydroxyluciferin (Hluc)

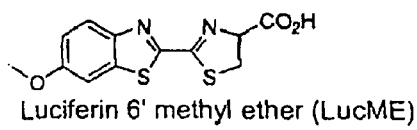
Luciferin 6' methyl ether (LucME)

Luciferin 6' ethyl ether

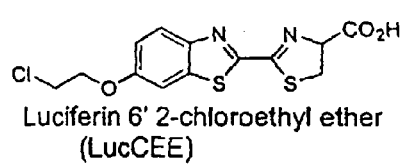
Luciferin 6' 2-chloroethyl ether (LucCEE)

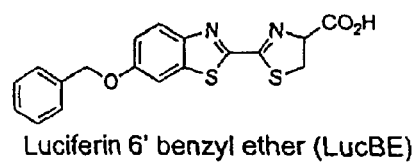
Luciferin 6' benzyl ether (LucBE)

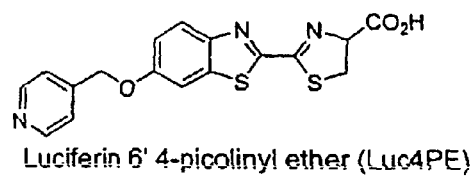
Luciferin 6' 4-picolinyl ether (Luc4PE)

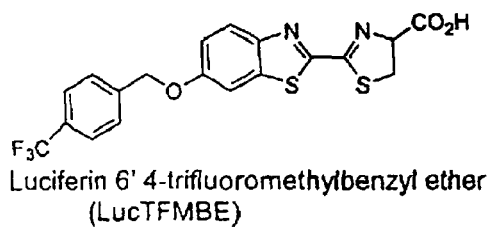
Luciferin 6' 4-trifluoromethylbenzyl ether (LucTFMBE)

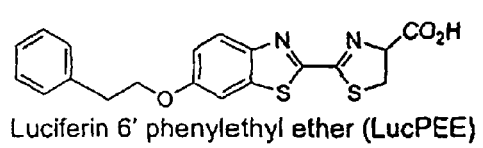
Luciferin 6' phenylethyl ether (LucPEE)

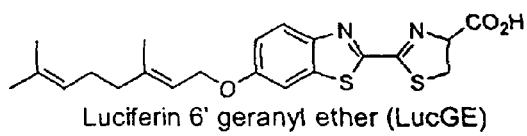
Luciferin 6' geranyl ether (LucGE)

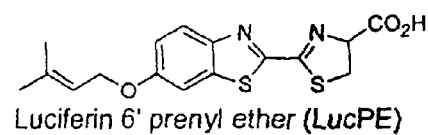
Luciferin 6' prenyl ether (LucPE)

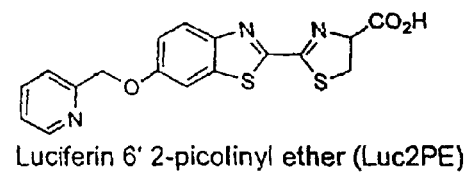
Luciferin 6' 2-picolinyl ether (Luc2PE)

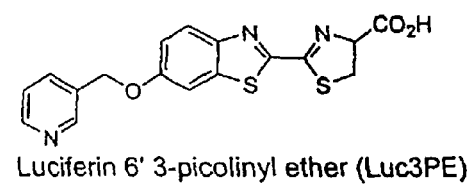
Luciferin 6' 3-picolinyl ether (Luc3PE)

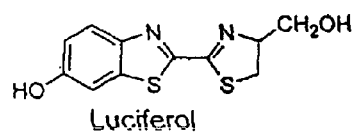
Luciferol

*FIG. 2*

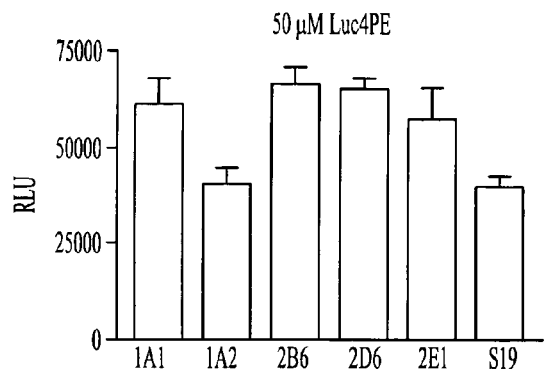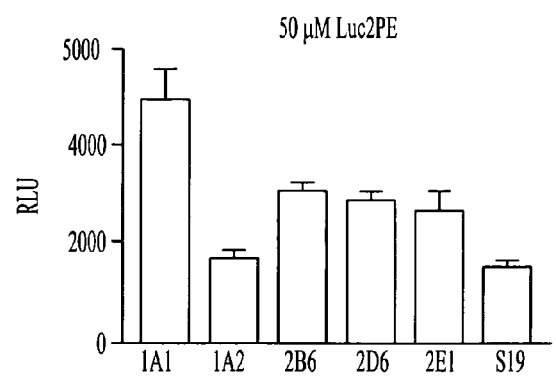
*FIG. 9A*  *FIG. 9B*
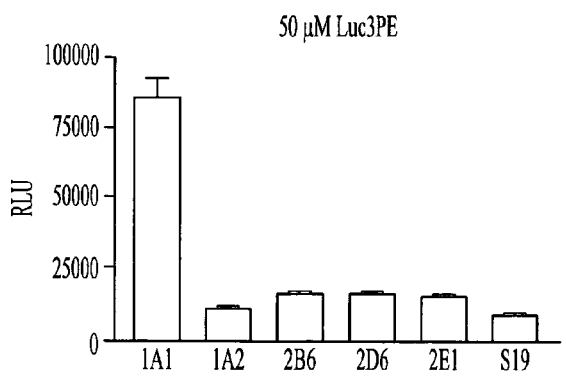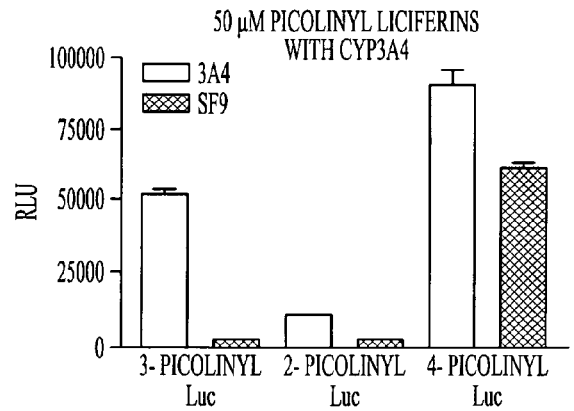
*FIG. 9C*  *FIG. 9D*

US 8,765,969 B2

LUMINESCENCE-BASED METHODS AND PROBES FOR MEASURING CYTOCHROME P450 ACTIVITY

CROSS-REFERENCE TO RELATED APPLICATIONS

This application is a continuation of U.S. patent application Ser. No. 10/665,314, filed Sep. 19, 2003, now U.S. Pat. No. 7,692,022 which application claims the benefit of U.S. Provisional Application No. 60/412,254, filed Sep. 20, 2002, and U.S. Provisional Application No. 60/483,309, filed Jun. 27, 2003, each of which is incorporated herein by reference in its entirety.

FIELD OF THE INVENTION

The present invention relates to methods, substrate compounds, and kits for analyzing the metabolic activity in animals, cells or in cell-free reaction formulations and for screening test compounds for their effect on metabolic activity. In particular, metabolic activity may be analyzed by employing a luminogenic molecule, e.g. luciferin derivative or coelenterazines, as either a cytochrome P450 substrate or a dual cytochrome P450 substrate and bioluminescent enzyme pro-substrate. In the case where the luminogenic molecule is a cytochrome P450 substrate and a bioluminescent enzyme pro-substrate, P450 metabolism of the luminogenic molecule in a first reaction generates the substrate for a bioluminescent enzyme. The bioluminescent enzyme then acts on the substrate in a second light-emitting reaction. P450 activity is then ascertained by measuring the luminescence of the reaction mixture relative to a control reaction mixture. The present invention also relates to a method and kit for relieving inhibition of luciferase by its inhibitor inorganic pyrophosphate (iPP) using a pyrophosphatase such as inorganic pyrophosphatase enzyme (iPPase).

BACKGROUND OF THE INVENTION

The presence and activity of enzymes can be used to determine the health or metabolic state of a cell. Enzymes are also markers for the cell type since the occurrence and activity of certain enzymes is frequently characteristic of a particular cell. For instance, the activity of certain enzymes can often be used to distinguish cells of bacterial, plant or animal origin, or to distinguish the identity of tissue from which the enzyme originates.

Detection of the presence and activity of enzymes can be facilitated by substrates that are converted by the enzyme of interest to a product that has at least one property that can be measured. These reporter molecules include fluorescent and chromogenic substrates. Fluorescent substrates have been preferable because, in many cases, they have a very high sensitivity and may permit measurements in living single cells with high spatial and temporal resolution. Chromogenic substrates can be very specific but often lack a high degree of resolution.

One family of enzymes useful for measuring the activity of living cells or in extracts of cells is the Cytochrome P450 family. Cytochrome P450s (CYP450s) are a large family of heme-containing enzymes that, in addition to the endogenous role in cell proliferation and development, includes many catalysts for detoxification and activation of lipophilic xenobiotics including therapeutic drugs, chemical carcinogens and environmental toxins. In some cases the metabolite(s) is more toxic than the parent compound. However, in other cases, metabolism of a therapeutic compound reduces the bioavailablity of the compound, lowering efficacy. This family of genes and the polymorphisms within the family play important roles in the interindividual variation in drug metabolism, occurrence and severity of side effects and therapeutic failures.

Hundreds of cytochrome P450s have been identified in diverse organisms including bacteria, fungi, plants, and animals (18). All CYP450s use a heme cofactor and share structural attributes. Most CYP450s are 400 to 530 amino acids in length. The secondary structure of the enzyme is about 70% alpha-helical and about 22% beta-sheet. The region around the heme-binding site in the C-terminal part of the protein is conserved among cytochrome P450s. A ten amino acid signature sequence in this heme iron ligand region has been identified which includes a conserved cysteine residue involved in binding the heme iron in the fifth coordination site. In eukaryotic CYP450s, a membrane-spanning region is usually found in the first 15-20 amino acids of the protein, generally consisting of approximately 15 hydrophobic residues followed by a positively charged residue (18, 19.)

Some of the genes encoding CYP450s are inducible at the transcription level by the compounds they metabolize (1,2). The genes encoding CYP450s have been divided into families based on homology of deduced amino acid sequences (3). All mammals share at least 14 CYP450 families but most drug metabolism is catalyzed by only three families: CYP1, CYP2 and CYP3. Most of the P450 catalyzed drug metabolism in humans takes place in the liver and is accounted for by about 13 enzymes: CYP1A1, CYP1A2, CYP2A6, CYP2B6, CYP2C8, CYP2C9, CYP2C18, CYP2C19, CYP2D6, CYP2E1, CYP3A4, CYP3A5 and CYP3A7 (4).

Because of the central role CYP450s play in drug clearance, toxicity and drug-drug interactions, CYP450s make useful targets for narrowing the field of compounds that should be moved forward in the drug development process (5,8). Furthermore, knowledge of CYP450/drug interactions can be predictive of drug disposition in a patient. There is a need for screening assays that can be used in high throughput mode. Compounds with properties that change in an easily detectable way upon oxidation by a CYP450 are useful as probes in high throughput assays for detecting effects on CYP450 activity (6,7). There is also need for a method for analyzing metabolic activity in cells under physiological conditions, using a substrate that is specific for CYP450 isozymes and yields products that are easily detectable. The signal should be detectable in cell-free extracts of cells and in living cells and the assay should have a low background signal.

Finally, there is a need to protect luciferase activity from its inhibitor inorganic pyrophosphate. Although the inventors do not intend to limit the source of pyrophosphate, pyrophosphate may be present as a contaminant in orthophosphate salts used in buffers containing a luciferase-based reaction or may be generated as a product of a luciferase reaction with ATP, $O_2$ and luciferin.

SUMMARY OF THE INVENTION

Applicants have fulfilled these needs by providing methods, substrate compounds, and kits which can identify a compound, e.g., drug candidate, affecting a cytochrome P450 enzyme in a highly specific manner.

The invention provides luminogenic molecules that are useful as P450 substrates or as dual P450 substrates and pro-substrates of bioluminescent enzymes. In one embodiment of the invention, the luminogenic molecules are derivatives of (4S)-4,5-dihydro-2-(6-hydroxy-benzothiazolyl)-4-thiazolecarboxylic acid (D-luciferin) or 2-(4-hydroxybenzyl)-6-(4-hydroxyphenyl)-8-benzyl-3,7-dihydroimidazo[1,2-a]pyrazine-3-one (coelenterazine) which are P450 substrates and pro-substrates of luciferase. In the absence of prior P450 metabolism, these luciferin derivatives alone have limited or no capacity to interact with luciferase in light generating reactions. These compounds are selectively converted by CYP450s to light generating substrates for luciferase reactions and thereby provide the basis of assays with a luminescent readout.

The invention also provides a method for direct and indirect determination of P450 activity based on luminogenic molecules that are natural coelenterazine and coelenterazine derivatives (collectively referred to as coelenterazines).

The invention also provides methods for using luminogenic molecules to determine whether a candidate drug (or class of candidate drugs) is a CYP450 enzyme substrate or regulator or CYP450 gene regulator, and related methods for selecting a candidate drug that will not be too efficiently metabolized by at least one CYP450 enzyme and/or that the drug will not act as an inhibitor of at least one CYP450 enzyme, and/or elicit an unfavorable drug-drug interaction. Methods of screening a candidate drug (or libraries of drug candidates) of the present invention may be performed by a one-step or a two-step CYP450/bioluminescent enzyme method in a cell-free, cell-based, tissue-based or animal-based environment or may be part of a high or ultra high throughput screening of libraries of drug candidates.

The invention also provides a method and kit for relieving inhibition of luciferase by its inhibitor inorganic pyrophosphate (iPP) which may be present as a contaminant or generated as a product of a luciferase-based reaction with ATP, O2 and luciferin.

The invention also provides a method and kit for enhancing or stabilizing a luminescent signal in a luciferase-based reaction that employs a reversible luciferase inhibitor.

Thus, in one embodiment of the invention, a method is provided for measuring the activity of a cytochrome P450 enzyme comprising:
(a) providing a luminogenic molecule wherein the molecule is a cytochrome P450 substrate and a pro-substrate of bioluminescent enzyme;
(b) contacting the luminogenic molecule with at least one cytochrome P450 enzyme and at least one bioluminescent enzyme to produce a reaction mixture; and
(c) determining cytochrome P450 activity by measuring luminescence of the reaction mixture.

In one aspect of this embodiment of the invention, step (b) further includes a pyrophosphatase such as an inorganic pyrophosphatase.

In another aspect of this embodiment of the invention, the luminogenic molecule, the cytochrome P450 enzyme, and the bioluminescent enzyme are contacted at about the same time.

In another aspect of this embodiment of the invention, the luminogenic molecule is contacted with at least one cytochrome P450 enzyme to form a first reaction mixture prior to contacting with the bioluminescent enzyme to form a second reaction mixture.

In another aspect of this embodiment of the invention, the second reaction mixture further comprises a detergent, preferably a non-ionic detergent.

In another embodiment of the invention, a method is provided for measuring cytochrome P450 enzyme activity in a cell comprising:

(a) providing a luminogenic molecule wherein the molecule is a cytochrome P450 substrate and a pro-substrate of bioluminescent enzyme;
(b) contacting a cell with the luminogenic molecule and a bioluminescent enzyme to produce a mixture; and
(c) determining cytochrome P450 activity of the cell by measuring luminescence of the mixture.

In one aspect of this embodiment of the invention, cell is recombinant and expresses the bioluminescent enzyme.

In another aspect of this embodiment of the invention, step (b) cell is further contacted with a lysis reagent.

In another aspect of this embodiment of the invention, the cell is lysed prior to step (b).

In another aspect of this embodiment of the invention, the cell is lysed prior to step (c).

In another aspect of this embodiment of the invention, the cell is contacted first with the luminogenic molecule to produce a first reaction mixture prior to contact with the bioluminescent enzyme to produce a second reaction mixture. The second reaction mixture may further comprises a detergent such as a non-ionic detergent and/or a pyrophosphatase such as an inorganic pyrophosphatase.

In another embodiment of the invent, a method is provided for measuring cytochrome P450 enzyme activity in animal tissue comprising:
(a) providing a luminogenic molecule wherein the molecule is a cytochrome P450 substrate and a pro-substrate of bioluminescent enzyme;
(b) contacting an animal tissue with the luminogenic molecule and a bioluminescent enzyme to provide a mixture; and
(c) determining cytochrome P450 activity of the tissue by measuring luminescence of the mixture.

In one aspect of this embodiment of the invention, the tissue is contacted first with the luminogenic molecule for a first predetermined time period prior to contact with the bioluminescent enzyme to provide a second mixture. The second reaction mixture may further comprise a detergent such as a non-ionic detergent and/or a pyrophosphatase such as inorganic pyrophosphatase.

In another embodiment of the invention, a method is provided for measuring cytochrome P450 enzyme activity in an animal comprising:
(a) providing a luminogenic molecule wherein the molecule is a cytochrome P450 substrate and a pro-substrate of bioluminescent enzyme;
(b) administering the luminogenic molecule to the animal;
(c) obtaining a biological sample from the animal; and
(d) contacting the biological sample with a bioluminescent enzyme to form a reaction mixture; and
(e) determining cytochrome P450 activity of the animal by measuring luminescence.

In one aspect of this embodiment of the invention, the reaction mixture further comprises a detergent such as a non-ionic detergent and/or a pyrophosphatase such as an inorganic pyrophosphatase.

In another embodiment of the invention, a method is provided for measuring cytochrome P450 enzyme activity in a transgeneic animal having a bioluminescent enzyme transgene, said method comprising:
(a) providing a luminogenic molecule wherein the molecule is a cytochrome P450 substrate and a pro-substrate of bioluminescent enzyme;
(b) administering the luminogenic molecule to a transgeneic animal having a bioluminescent enzyme transgene; and
(c) determining cytochrome P450 activity of the animal by measuring luminescence of tissue from the transgeneic animal.

In another aspect of this embodiment of the invention, the bioluminescent enzyme transgene is a luciferase transgene.

In another embodiment of the invention, a method is provided for screening a compound for its effect on cytochrome P450 activity comprising:
 (a) providing a compound for screening;
 (b) providing a luminogenic molecule wherein the molecule is a cytochrome P450 substrate and a pro-substrate of bioluminescent enzyme;
 (c) contacting the compound, the luminogenic molecule, at least one cytochrome P450 enzyme, and a bioluminescent enzyme to produce a reaction mixture; and
 (d) determining cytochrome P450 activity, if any, resulting from the interaction of the compound with the cytochrome P450 enzyme by measuring luminescence of the reaction mixture.

In one aspect of this embodiment of the invention, the compound, luminogenic molecule, the cytochrome P450 enzyme, and the bioluminescent enzyme are contacted at about the same time.

In another aspect of this embodiment of the invention, the compound, luminogenic molecule and at least one cytochrome P450 enzyme are contacted first to form a first reaction mixture prior to contacting with the bioluminescent enzyme to form a second reaction mixture. The second reaction mixture further includes a detergent such as a non-ionic detergent and/or a pyrophosphatase such as an inorganic pyrophosphatase.

In another aspect of this embodiment of the invention, the compound is contacted first with the one or more cytochrome P450 enzymes to form a first reaction mixture, the first reaction mixture are then contacted with the luminogenic molecule to form a second reaction mixture, and the second reaction mixture is then contacted with a bioluminescent enzyme to form a third reaction mixture. The third reaction mixture may further include a detergent such as a non-ionic detergent and/or a pyrophosphatase such as an inorganic pyrophosphatase.

In another embodiment of the invention, a method is provided for determining the effect of a compound on cytochrome P450 enzyme activity of a cell comprising the steps of:
 (a) providing a compound for testing (b) contacting a cell with a test compound, a luminogenic molecule and a bioluminescent enzyme, wherein the luminogenic molecule is a cytochrome P450 substrate and a pro-substrate of bioluminescent enzyme; and
 (c) determining cytochrome P450 enzyme activity of the cell, if any, resulting from the exposure of the cell to the test compound by measuring and comparing luminescence from said cell with a second cell not exposed to the test compound.

In one aspect of this embodiment of the invention, the cell is recombinant and expresses the bioluminescent enzyme.

In another aspect of this embodiment of the invention, the cell is contacted first with the compound to produce a first reaction mixture prior to contact with the luminogenic molecule to produce a second reaction mixture. The second mixture may further comprise a bioluminescent enzyme. The bioluminescent enzyme may be added to the second reaction mixture after a predetermined time period. The second reaction mixture further includes a detergent such as a non-ionic detergent and/or a pyrophosphate such inorganic pyrophosphate.

In another aspect of this embodiment of the invention, step (b) further includes a pyrophosphatase such as an inorganic pyrophosphatase.

In another embodiment of the invention, a method is provided for determining the effect of a compound on cytochrome P450 enzyme activity of animal tissue comprising the steps of:
 (a) providing a test compound;
 (b) contacting an animal tissue with the test compound, a luminogenic molecule and a bioluminescent enzyme, wherein the luminogenic molecule is a cytochrome P450 substrate and a pro-substrate of bioluminescent enzyme; and
 (c) determining cytochrome P450 enzyme activity of the tissue, if any, resulting from the exposure of the tissue to the test compound by measuring and comparing luminescence from said tissue with a control tissue not exposed to the test compound.

In one aspect of this embodiment of the invention, the animal tissue expresses the bioluminescent enzyme.

In another aspect of this embodiment of the invention, the tissue is contacted with the test compound to produce a first mixture prior to contact with the luminogenic molecule to produce a second mixture. The second mixture further comprises a bioluminescent enzyme. The bioluminescent enzyme may added to the second reaction mixture after a predetermined time period. The second reaction mixture may further include a detergent such as a non-ionic detergent.

In another aspect of this embodiment of the invention, step (b) may further include a pyrophosphatase such as an inorganic pyrophosphatase.

In another embodiment of the invention, a method is provided for determining the effect of a compound on cytochrome P450 enzyme activity in an animal comprising:
 (a) providing a compound for testing;
 (b) administering the test compound to an animal;
 (c) administering a luminogenic molecule to the animal, wherein the luminogenic molecule is a cytochrome P450 substrate and a pro-substrate of bioluminescent enzyme;
 (d) obtaining a biological sample from said animal;
 (e) contacting the biological sample with a bioluminescent enzyme; and
 (f) determining cytochrome P450 enzyme activity of said animal after exposure of said animal to the test compound by measuring and comparing luminescence from said biological sample with a second biological sample taken from an animal not exposed to said test compound.

In one aspect of this embodiment of the invention, step (c) is performed after step (b) after a predetermined time period has elapsed.

In another aspect of this embodiment of the invention, the biological sample is taken from the animal just prior to exposure to the test compound.

In another aspect of this embodiment of the invention, the biological sample comprises blood, serum, bile, urine, feces, or tissue.

In another embodiment of the invention, a method is provided for determining the effect of a compound on cytochrome P450 enzyme activity in an transgeneic animal having a bioluminescent enzyme transgene, said method comprising:
 (a) providing a compound for testing;
 (b) administering the test compound to a transgeneic animal having a bioluminescent enzyme transgene;
 (c) administering a luminogenic molecule to the animal, wherein the luminogenic molecule is a cytochrome P450 substrate and a pro-substrate of the bioluminescent enzyme; and
 (d) determining cytochrome P450 enzyme activity of said animal after exposure of said animal to the test compound by measuring and comparing luminescence from tissue from said transgeneic animal with a second biological sample taken from another transgeneic animal not exposed to said test compound.

In one aspect of this embodiment of the invention, step (c) is performed after step (b) after a predetermined time period has elapsed.

In another aspect of this embodiment of the invention, the bioluminescent enzyme transgene is a luciferase transgene.

In another embodiment of the invention, a high throughput method is provided for rapidly screening a plurality of compounds to determine their effect on cytochrome P450 activity, said method comprising:

(a) providing compounds for screening;
(b) contacting the compounds to be screened with (i) a luminogenic molecule wherein the luminogenic molecule is a cytochrome P450 substrate and a pro-substrate of bioluminescent enzyme; (ii) one or more cytochrome P450 enzymes; and (iii) one or more bioluminescent enzymes to form reaction mixtures, each reaction mixture having one or more compounds; and
(c) determining cytochrome P450 enzyme activity, if any, resulting from the interaction of one or more compounds with one or more cytochrome P450 enzymes by measuring luminescence of the reaction mixtures.

In one aspect of this embodiment of the invention, the compounds are contacted first with the one or more cytochrome P450 enzymes to form first reaction mixtures, the first reaction mixtures are then contacted with the luminogenic molecule to form second reaction mixtures, and the second reaction mixtures are then contacted with a bioluminescent enzyme to form third reaction mixtures. The third reaction mixture may further include a detergent such as a non-ionic detergent.

In another aspect of this embodiment of the invention, the compounds are contacted first with one or more cytochrome P450 enzymes and the luminogenic molecule to form first reaction mixtures prior to contact with one or more bioluminescent enzymes to form a second reaction mixture. The second reaction mixture may further comprise a detergent such as a non-ionic detergent.

In another aspect of this embodiment of the invention, the compounds are contacted simultaneously or contemporaneously with the one or more cytochrome P450 enzymes and the luminogenic molecule to form first reaction mixtures prior to contacting with one or more bioluminescent enzymes to form second reaction mixtures.

In another aspect of this embodiment of the invention, step (b) further comprises a pyrophosphatase such as an inorganic pyrophosphatase.

In another embodiment of the invention, a high throughput method is provided for rapidly screening a plurality of compounds to determine their effect on cytochrome P450 activity of a cell, said method comprising:

(a) providing compounds for screening;
(b) contacting cells with the compounds to be screened, a luminogenic molecule, and one or more bioluminescent enzymes to form reaction mixtures, wherein the luminogenic molecule is a cytochrome P450 substrate and a pro-substrate of bioluminescent enzyme and each reaction mixture having one or more compounds;
(c) determining cytochrome P450 enzyme activity, if any, resulting from the interaction of one or more compounds with one or more cytochrome P450 enzymes by measuring luminescence of the reaction mixtures.

In one aspect of this embodiment of the invention, the cells are recombinant and express bioluminescent enzyme.

In another aspect of this embodiment of the invention, the bioluminescent enzyme from an exogenous source is used.

In another aspect of this embodiment of the invention, steps (b) and/or (c) further comprises a pyrophosphatase such as an inorganic pyrophosphatase.

In another aspect of this embodiment of the invention, the cells are first contacted with the compounds and luminogenic molecule for a first predetermined time period, then contacted with the bioluminescent enzyme for a second predetermined time period. Detergent such as non-ionic detergent may be present during the second predetermined time period.

In another aspect of this embodiment of the invention, the cells are first contacted with the compounds for a first predetermined time period, then contacted with the luminogenic molecule for a second predetermined time period, then contacted with the bioluminescent enzyme for a third predetermined time period. Detergent such as non-ionic detergent may present in the mixture during the third predetermined time period.

In another aspect of this embodiment of the invention, the cells are first contacted with the compounds for a first predetermined time period, then contacted with the luminogenic molecule and bioluminescent enzyme for a second predetermined time period.

In another aspect of this embodiment of the invention, the cells, compounds, luminogenic molecule, and bioluminescent enzyme are contacted simultaneously.

In another embodiment of the invention, a high throughput method is provided for rapidly screening a plurality of compounds to determine their effect on cytochrome P450 activity of animal tissue, said method comprising:

(a) providing compounds for screening;
(b) contacting animal tissue with the compounds to be screened, a luminogenic molecule, and one or more bioluminescent enzymes to form reaction mixtures, wherein the luminogenic molecule is a cytochrome P450 substrate and a pro-substrate of bioluminescent enzyme and each reaction mixture having one or more compounds;
(c) determining cytochrome P450 enzyme activity, if any, resulting from the interaction of one or more compounds with one or more cytochrome P450 enzymes by measuring luminescence of the reaction mixtures.

In one aspect of this embodiment of the invention, the tissue expresses at least one bioluminescent enzyme.

In another aspect of this embodiment of the invention, the tissue is first contacted with the compounds and luminogenic molecule for a first predetermined time period prior to contact with the bioluminescent enzyme. Detergent such as non-ionic detergent may be added after the first predetermined time period. Detergent and bioluminescent enzyme may be added at the same time.

In another aspect of this embodiment of the invention, detergent is added prior to addition of the bioluminescent enzyme.

In another aspect of this embodiment of the invention, the tissue is first contacted with the compounds for a first predetermined time period, then contacted with the luminogenic molecule for a second predetermined time period, then contacted with the bioluminescent enzyme for a third predetermined time period. Detergent such as non-ionic detergent may be added after the second predetermined time period. Detergent and bioluminescent enzyme may be added at the same time. Detergent and bioluminescent enzyme may be added at the same time.

In another aspect of this embodiment of the invention, the tissue is first contacted with the compounds for a first predetermined time period, then contacted with the luminogenic molecule and bioluminescent enzyme for a second predetermined time period.

In another aspect of this embodiment of the invention, the tissue, compounds, luminogenic molecule, and bioluminescent enzyme are contacted simultaneously. In another aspect of this embodiment of the invention, steps (b) or (c) further comprises (iv) a pyrophosphatase such as an inorganic pyrophosphatase.

In another embodiment of the invention, a high throughput method is provided for rapidly screening a plurality of compounds to determine their effect on cytochrome P450 activity of animal, said method comprising:

(a) providing compounds for screening;

(b) contacting a living teleost with the compounds to be screened, a luminogenic molecule, and a bioluminescent enzyme to form reaction mixtures, wherein the luminogenic molecule is a cytochrome P450 substrate and a pro-substrate of bioluminescent enzyme and each reaction mixture having one or more compounds;

(c) determining cytochrome P450 enzyme activity, if any, resulting from the interaction of one or more compounds with one or more cytochrome P450 enzymes by measuring luminescence of the reaction mixtures that include test compounds in comparison to control mixtures without test compounds.

In one aspect of this embodiment of the invention, the telost is transgeneic and expresses bioluminescent enzyme.

In another aspect of this embodiment of the invention, the telosts are first contacted with the compounds and luminogenic molecule for a first predetermined time period prior to contact with the bioluminescent enzyme.

In another aspect of this embodiment of the invention, the telosts are first contacted with the compounds for a first predetermined time period, then contacted with the luminogenic molecule for a second predetermined time period, then contacted with the bioluminescent enzyme for a third predetermined time period.

In another aspect of this embodiment of the invention, the telosts are first contacted with the compounds for a first predetermined time period, then contacted with the luminogenic molecule and bioluminescent enzyme for a second predetermined time period.

In another aspect of this embodiment of the invention, the telosts, compounds, luminogenic molecule, and bioluminescent enzyme are contacted simultaneously.

In another aspect of this embodiment of the invention, steps (b) or (c) further comprises (iv) a pyrophosphatase such as an inorganic pyrophosphatase.

In another embodiment of the invention, in any of the above methods, the luminogenic molecule is a luciferin derivative and the bioluminescent enzyme is a luciferase. Preferably the luciferin derivative has a formula:

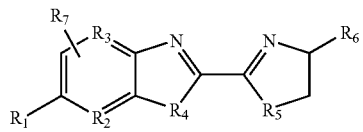

wherein $R_1$ represents hydrogen, hydroxyl, amino, $C_{1-20}$ alkoxy, substituted $C_{1-20}$ alkoxy, $C_{2-20}$ alkenyloxy, substituted $C_{2-20}$ alkenyloxy, halogenated $C_{2-20}$ alkoxy, substituted halogenated $C_{2-20}$ alkoxy, $C_{3-20}$ alkynyloxy, substituted $C_{3-20}$ alkynyloxy, $C_{3-20}$ cycloalkoxy, substituted $C_{3-20}$ cycloalkoxy, $C_{3-20}$ cycloalkylamino, substituted $C_{3-20}$ cycloalkylamino, $C_{1-20}$ alkylamino, substituted $C_{1-20}$ alkylamino, di $C_{1-20}$ alkylamino, substituted di$C_{1-20}$ alkylamino, $C_{2-20}$ alkenylamino, substituted $C_{2-20}$ alkenylamino, di $C_{2-20}$ alkenylamino, substituted di $C_{2-20}$ alkenylamino, $C_{2-20}$ alkenyl $C_{1-20}$ alkylamino, substituted $C_{2-20}$ alkenyl $C_{1-20}$ alkylamino, $C_{3-20}$ alkynylamino, substituted $C_{3-20}$ alkynylamino, di $C_{3-20}$ alkynylamino, substituted di alkylamino, $C_{3-20}$ alkynyl $C_{2-20}$alkenylamino, or substituted $C_{3-20}$ alkynyl $C_{2-20}$alkenylamino;

$R_2$ and $R_3$ independently represents C or N;

$R_4$ and $R_5$ independently represents S, O, $NR_9$ wherein $R_9$ represents hydrogen or $C_{1-20}$ alkyl, $CR_9R_{10}$ wherein $R_9$ and $R_{10}$ independently represent H, $C_{1-20}$ alkyl, or fluorine;

$R_6$ represents $CH_2OH$; $COR_{11}$ wherein $R_1$ represents H, OH, $C_{1-20}$ alkoxide, $C_{2-20}$ alkenyl, or $NR_{12}R_{13}$ wherein $R_{12}$ and $R_{13}$ are independently H or $C_{1-20}$ alkyl; or —$OM^+$ wherein $M^+$ is an alkali metal or a pharmaceutically acceptable salt; and $R_7$ represents H, $C_{1-4}$ alkyl, $C_{1-20}$ alkenyl, halogen, or $C_{1-6}$ alkoxide, with the proviso that $R_1$ is not OH or $NH_2$, $R_7$ is not H, $R_6$ is not $COR_{11}$, $R_{11}$ is not OH, $R_3$ and $R_2$ are not both carbon, and $R_4$ and $R_5$ are not both S at the same time (luciferin and aminoluciferin).

In another embodiment of the invention, in any of the above methods, the luminogenic molecule comprises coelenterazine or coelenterazine derivatives and the bioluminescent enzyme is a luciferase. Preferably the coelenterazine derivative has a formula:

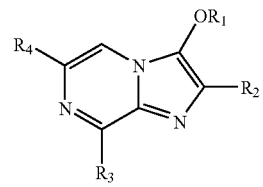

wherein $R_1$ is $C_{1-20}$ alkyl, branched $C_{3-20}$ alkyl, $C_{3-20}$ cycloalkyl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino; and $R_2$, $R_3$, and $R_4$ are independently hydrogen, $C_{1-20}$ alkyl, $C_{3-20}$ cycloalkyl, branched $C_{3-20}$ alkyl, aryl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino, aryl substituted with $C_{1-20}$ alkoxy, hydroxy, halogen, $C_{1-20}$ alkylamino, or di $C_{1-20}$ alkylamino. Preferably $R_4$ is aryl or aryl substituted with $C_{1-20}$ alkoxy, hydroxy, halogen, $C_{1-20}$ alkylamino, or $C_{1-20}$ dialkylamino.

In another embodiment of the invention, a kit is provided for determining the effect of a substance on cytochrome P450 enzyme activity comprising:

(a) one or more luminogenic molecules wherein the molecule is a cytochrome P450 enzyme substrate and a pro-substrate of luciferase enzyme; and (b) directions for using the kit.

In one aspect of this embodiment of the invention, the kit further comprises one or more bioluminescent enzymes such as a luciferase. Examples of luciferase include, without limitation, firefly lucifereaase or *Renilla* luciferase.

In another aspect of this embodiment of the invention, the kit further comprises ATP and magnesium ions.

In another aspect of this embodiment of the invention, the kit further comprises a detergent such as a non-ionic detergent.

In another aspect of this embodiment of the invention, the kit further comprising a pyrophosphatase such as an inorganic pyrophosphatase.

In another aspect of this embodiment of the invention, the luminogenic molecule is a D-luciferin derivative that is a substrate of a cytochrome P450 enzyme and a pro-substrate of a luciferase enzyme. Preferably the luciferin derivative has a formula:

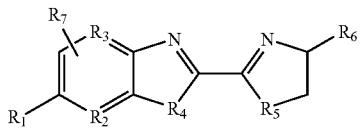

wherein $R_1$ represents hydrogen, hydroxyl, amino, $C_{1-20}$ alkoxy, substituted $C_{1-20}$ alkoxy, $C_{2-20}$ alkenyloxy, substituted $C_{2-20}$ alkenyloxy, halogenated $C_{2-20}$ alkoxy, substituted halogenated $C_{2-20}$ alkoxy, $C_{3-20}$ alkynyloxy, substituted $C_{3-20}$ alkynyloxy, $C_{3-20}$ cycloalkoxy, substituted $C_{3-20}$ cycloalkoxy, $C_{3-20}$ cycloalkylamino, substituted $C_{3-20}$ cycloalkylamino, $C_{1-20}$ alkylamino, substituted $C_{1-20}$ alkylamino, di $C_{1-20}$ alkylamino, substituted di$C_{1-20}$ alkylamino, $C_{2-20}$ alkenylamino, substituted $C_{2-20}$ alkenylamino, di $C_{2-20}$ alkenylamino, substituted di $C_{2-20}$ alkenylamino, $C_{2-20}$ alkenyl $C_{1-20}$ alkylamino, substituted $C_{2-20}$ alkenyl $C_{1-20}$ alkylamino, $C_{3-20}$ alkynylamino, substituted $C_{3-20}$ alkynylamino, di $C_{3-20}$ alkynylamino, substituted di $C_{3-20}$ alkynylamino, $C_{3-20}$ alkynyl $C_{1-20}$ alkylamino, substituted $C_{3-20}$ alkynyl $C_{1-20}$ alkylamino, $C_{3-20}$ alkynyl $C_{2-20}$alkenylamino, or substituted $C_{3-20}$ alkynyl $C_{2-20}$alkenylamino;

$R_2$ and $R_3$ independently represents C or N;

$R_4$ and $R_5$ independently represents S, O, $NR_8$ wherein $R_8$ represents hydrogen or $C_{1-20}$ alkyl, $CR_9R_{10}$ wherein $R_9$ and $R_{10}$ independently represent H, $C_{1-20}$ alkyl, or fluorine;

$R_6$ represents $CH_2OH$; $COR_{11}$ wherein $R_{11}$ represents H, OH, $C_{1-20}$ alkoxide, $C_{2-20}$ alkenyl, or $NR_{12}R_{13}$ wherein $R_{12}$ and $R_{13}$ are independently H or $C_{1-20}$ alkyl; or —$OM^+$ wherein $M^+$ is an alkali metal or a pharmaceutically acceptable salt; and $R_7$ represents H, $C_{1-6}$ alkyl, $C_{1-20}$ alkenyl, halogen, or $C_{1-6}$ alkoxide, with the proviso that $R_1$ is not OH or $NH_2$, $R_7$ is not H, $R_6$ is not $COR_{11}$, $R_{11}$ is not OH, $R_3$ and $R_2$ are not both carbon, and $R_4$ and $R_5$ are not both S at the same time (luciferin and aminoluciferin).

In another aspect of this embodiment of the invention, the luminogenic molecule comprises coelenterazine or a coelenterazine derivative. Preferably the coelenterazine derivative has a formula:

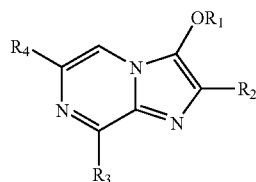

wherein $R_1$ is $C_{1-20}$ alkyl, branched $C_{3-20}$ alkyl, $C_{3-20}$ cycloalkyl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino; and $R_2$, $R_3$, and $R_4$ are independently hydrogen, $C_{1-20}$ alkyl, $C_{3-20}$ cycloalkyl, branched $C_{3-20}$ alkyl, aryl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino, aryl substituted with $C_{1-20}$ alkoxy, hydroxy, halogen, $C_{1-20}$ alkylamino, or di $C_{1-20}$ alkylamino. Preferably $R_4$ is aryl or aryl substituted with $C_{1-20}$ alkoxy, hydroxy, halogen, $C_{1-20}$ alkylamino, or $C_{1-20}$ dialkylamino.

In another aspect of this embodiment of the invention, the kit further comprises a reversible luciferase inhibitor. Preferably, the reversible luciferase inhibitor is 2-(4-aminophenyl)-6-methylbenzothiazole (APMBT) or 2-amino-6-methylbenzothiazole (AMBT).

In another embodiment of the invention, a D-luciferin derivative is provided that is a substrate of a cytochrome P450 enzyme and a pro-substrate of luciferase enzyme.

In another embodiment of the invention, a composition is provided which comprises the D-luciferin derivative that is a substrate of a cytochrome P450 enzyme and a pro-substrate of luciferase enzyme.

In one aspect of this embodiment of the invention, the composition further comprises a pyrophosphatase such as an inorganic pyrophosphatase.

In another embodiment of the invention, a D-luciferin derivative is provided having the formula:

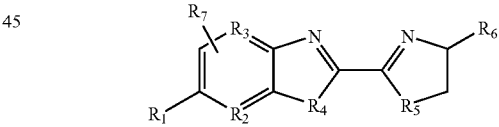

wherein $R_1$ represents hydrogen, hydroxy, $C_{1-20}$ alkoxy or $C_{1-20}$ alkenyloxy wherein the alkoxy and alkenyloxy are substituted with halogen, hydroxy, amino, cyano, azido, heteroaryl or aryl substituted with haloalkyl; or $R_1$ represents $C_{3-20}$ alkynyloxy; cycloalkoxy, cycloalkylamino, $C_{1-20}$ alkylamino, di$C_{1-20}$ alkylamino, $C_{2-20}$ alkenylamino, di$C_{2-20}$ alkenylamino, $C_{2-20}$ alkenyl $C_{1-20}$alkylamino, $C_{3-20}$ alkynylamino, di$C_{3-20}$ alkynylamino, $C_{3-20}$ alkynyl $C_{1-20}$alkylamino, or $C_{3-20}$ alkynyl $C_{2-20}$alkenylamino, wherein each of the above groups are optionally substituted with halogen, hydroxy, amino, cyano, azido, heteroaryl or aryl substituted with haloalkyl;

$R_2$ and $R_3$ independently represent C or N;

$R_4$ and $R_5$ independently represent S; O; $NR_9$ wherein $R_9$ represents hydrogen or $C_{1-20}$ alkyl; $CR_9R_{10}$ wherein $R_9$ and $R_{10}$ independently represent H, $C_{1-20}$ alkyl or fluorine;

R₆ represents CH₂OH; COR₁₁ wherein R₁₁ represents hydrogen, hydroxy, $C_{2-20}$ alkenyl, or —OM⁺ wherein M⁺ is an alkali metal or a pharmaceutically acceptable salt; and R₇ represents hydrogen, $C_{1-6}$ alkyl, $C_{2-20}$ alkenyl, halogen or $C_{1-6}$ alkoxide, provided that when R₁ is hydroxy, R₇ is not hydrogen, R₁₁ is not hydroxy, R₂ and R₃ are not both carbon, and R₄ and R₅ are not both S (luciferin);

when R₁ is hydrogen, R₇ is not hydrogen, R₁₁ is not hydroxy, R₂ and R₃ are not both carbon, and R₄ and R₅ are not both S (dehydroluciferin); and when R₁ is hydroxy, R₇ is not hydrogen, R₆ is not CH₂OH, R₂ and R₃ are not both carbon, and R₄ and R₅ are not both S (luciferol).

In one aspect of this embodiment of the invention, the compound is selected from the group consisting of luciferin 6' 2-chloroethyl ether;
luciferin 6' 4-picolinyl ether;
luciferin 6' 4-trifluoromethylbenzyl ether;
luciferin 6' 2-picolinyl ether; or
luciferin 6' 3-picolinyl ether.

In another aspect of this embodiment of the invention, the compound is selected from the group consisting of luciferin 6' benzyl ether;
luciferin 6' 4-trifluoromethylbenzyl ether;
luciferin 6' phenylethyl ether;
luciferin 6' geranyl ether; or
luciferin 6' prenyl ether.

In another aspect of this embodiment of the invention, a composition is provided which comprises the D-luciferin derivative. The composition may further comprise a pyrophosphatase such as an inorganic pyrophosphatase.

In another embodiment of the invention, a method is provided for measuring P450 enzyme activity comprising (a) providing a coelentrazine or a coelenterazine derivative that is a P450 substrate and is chemiluminescent;

(b) contacting a coelentrazine or coelenterazine derivative with at least one cytochrome P450 enzyme to form a reaction mixture; and (c) determining cytochrome P450 activity by measuring chemoluminescence of the reaction mixture.

In another embodiment of the invention, a method is provided for measuring cytochrome P450 enzyme activity in a cell comprising:

(a) providing a coelentrazine or a coelenterazine derivative that is a P450 substrate and is chemiluminescent;

(b) contacting a cell with the coelenterazine or coelenterazine derivative to form a reaction mixture; and (c) determining cytochrome P450 activity of the cell by measuring the chemiluminescence of the reaction mixture.

In one aspect of this embodiment of the invention, step (b) cell is further contacted with a lysis agent.

In another aspect of this embodiment of the invention, the cell is lysed prior to step (b).

In another aspect of this embodiment of the invention, the cell is lyzed prior to step (c).

In another embodiment of the invention, a method is provided for measuring cytochrome P450 enzyme activity in animal tissue comprising:

(a) providing coelenterazine or a coelenterazine derivative that is a P450 substrate and is chemiluminescent;

(b) contacting an animal tissue with the coelenterazine or a coelenterazine derivative and a bioluminescent enzyme to provide a mixture; and (c) determining cytochrome P450 activity of the tissue by measuring luminescence of the mixture.

In another embodiment of the invention, a method is provided for measuring cytochrome P450 enzyme activity in an animal comprising:

(a) providing coelenterazine or a coelenterazine derivative that is a P450 substrate and is chemiluminescent;

(b) administering the coelentrazine or a coelenterazine derivative to an animal;

(c) obtaining a biological sample from the animal; and (d) determining cytochrome P450 activity of the animal by measuring chemiluminescence of the sample.

In another embodiment of the invention, a method is provided for screening a compound for its effect on cytochrome P450 activity comprising:

(a) providing a compound for screening;

(b) providing coelenterazine or a coelenterazine derivative that is a substrate of cytochrome P450 and is chemiluminescent;

(c) contacting the compound, coelentrazine or a coelenterazine derivative, and a cytochrome P450 enzyme to produce a reaction mixture; and (d) determining cytochrome P450 activity, if any, resulting from the interaction of the compound with the cytochrome P450 enzyme by measuring chemiluminescence of the reaction mixture.

In another embodiment of the invention, a method is provided for determining the effect of a compound on cytochrome P450 enzyme activity of a cell comprising the steps of:

(a) providing a compound for testing;

(b) contacting a cell with a test compound and coelentrazine or a coelenterazine derivative that is a substrate of cytochrome P450 and that is chemiluminescent; and (c) determining cytochrome P450 enzyme activity of the cell, if any, resulting from the exposure of the cell to the test compound by measuring and comparing chemiluminescence from said cell with a second cell not exposed to the test compound.

In another embodiment of the invention, a method is provided for determining the effect of a compound on cytochrome P450 enzyme activity of animal tissue comprising the steps of (a) providing a test compound;

(b) contacting an animal tissue with a test compound and coelentrazine or a coelenterazine derivative that is a substrate of cytochrome P450 and that is chemiluminescent; and (c) determining cytochrome P450 enzyme activity of the tissue, if any, resulting from the exposure of the tissue to the test compound by measuring and comparing chemiluminescence from said tissue with a control tissue not exposed to the test compound.

In another embodiment of the invention, a method is provided for determining the effect of a compound on cytochrome P450 enzyme activity in an animal comprising:

(a) providing a compound for testing;

(b) administering the test compound to an animal;

(c) administering coelentrazine or a coelenterazine derivative that is a substrate of cytochrome P450 and that is chemiluminescent;

(d) obtaining a biological sample from said animal;

(e) determining cytochrome P450 enzyme activity of said animal after exposure of said animal to the test compound by measuring and comparing chemiluminescence from said biological sample with a second biological sample taken from an animal not exposed to said test compound.

In another embodiment of the invention, a high throughput method is provided for rapidly screening a plurality of compounds to determine their effect on cytochrome P450 activity, said method comprising:

(a) providing compounds for screening;

(b) contacting the compounds to be screened with (i) coelentrazine or a coelenterazine derivative that is a substrate of cytochrome P450 and that is chemiluminescent; and (ii) one or more cytochrome P450 enzymes, each reaction mixture having one or more compounds; and (c) determining cytochrome P450 enzyme activity, if any, resulting from the interaction of one or more compounds with one or more cytochrome P450 enzymes by measuring chemiluminescence of the reaction mixtures.

In another embodiment of the invention, a high throughput method for rapidly screening a plurality of compounds to determine their effect on cytochrome P450 activity of a cell, said method comprising:

(a) providing compounds for screening;

(b) contacting cells with the compounds to be screened and coelenterazine or a coelenterazine derivative that is a substrate of cytochrome P450 and that is chemiluminescent to form reaction mixtures, each reaction mixture having one or more compounds;

(c) determining cytochrome P450 enzyme activity, if any, resulting from the interaction of one or more compounds with one or more cytochrome P450 enzymes by measuring chemiluminescence of the reaction mixtures.

In another embodiment of the invention, a high throughput method is provided for rapidly screening a plurality of compounds to determine their effect on cytochrome P450 activity of animal tissue, said method comprising: (a) providing an animal tissue with CYP450 activity (a) providing compounds for screening;

(b) contacting animal tissue with the compounds to be screened and coelenterazine or a coelenterazine derivative that is a substrate of cytochrome P450 and that is chemiluminescent to form reaction mixtures, each reaction mixture having one or more compounds;

(c) determining cytochrome P450 enzyme activity, if any, resulting from the interaction of one or more compounds with one or more cytochrome P450 enzymes by measuring chemiluminescence of the reaction mixtures.

In another embodiment of the invention, a high throughput method is provided for rapidly screening a plurality of compounds to determine their effect on cytochrome P450 activity of animal, said method comprising:

(a) providing compounds for screening;

(b) contacting a living teleost with the compounds to be screened and coelenterazine or a coelenterazine derivative that is a substrate of cytochrome P450 and that is chemiluminescent to form reaction mixtures, each reaction mixture having one or more compounds;

(c) determining cytochrome P450 enzyme activity, if any, resulting from the interaction of one or more compounds with one or more cytochrome P450 enzymes by measuring chemiluminescence of the reaction mixtures that include test compounds in comparison to control mixtures without test compounds.

In another embodiment of the invention, in any of the above methods involving coleentrazine or derivative that is a substrate of cytochrome P450 and that is chemiluminescent, preferably the coelenterazine derivative has a formula:

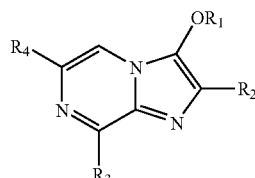

wherein $R_1$ is $C_{1-20}$ alkyl, branched $C_{3-20}$ alkyl, $C_{3-20}$ cycloalkyl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino; and $R_2$, $R_3$, and $R_4$ are independently hydrogen, $C_{1-20}$ alkyl, $C_{3-20}$ cycloalkyl, branched $C_{3-20}$ alkyl, aryl, aralkyl, $C_{1-20}$ alkyl substituted with $C_{1-20}$ alkoxy, hydroxy, halogen, $C_{1-20}$ alkylamino, or di$C_{1-20}$ alkylamino, aralkyl substituted with $C_{1-20}$ alkoxy, hydroxy, halogen, $C_{1-20}$ alkylamino, or di$C_{1-20}$ alkylamino, aryl substituted with $C_{1-20}$ alkoxy, hydroxy, halogen, $C_{1-20}$ alkylamino, or di $C_{1-20}$ alkylamino.

In one aspect of this embodiment of the invention, preferably $R_4$ is aryl or aryl substituted with $C_{1-20}$ alkoxy, hydroxy, halogen, $C_{1-20}$ alkylamino, or $C_{1-20}$ dialkylamino.

In another aspect of this embodiment of the invention, the coelentrazine derivative is coelenterazine HH, methoxycoelenterazine HH or coelenterazine.

In another embodiment of the invention, a method is provided for enhancing the stability of a luminescent signal generated by a luciferase-based reaction mixture comprising contacting a luciferase with a reversible luciferase inhibitor in an amount effective to enhance the stability and prolong the lifetime of the luminescent signal relative to the luminescent signal generated in a comparable luciferase-based reaction mixture in the absence of the inhibitor.

In one aspect of this embodiment of the invention, the reversible luciferase inhibitor is a competitive inhibitor.

In another aspect of this embodiment of the invention, the reversible luciferase inhibitor comprises 2-(4-aminophenyl)-6-methylbenzothiazole (APMBT) or 2-amino-6-methylbenzothiazole (AMBT).

In another aspect of this embodiment of the invention, the effective amount of the inhibitor ranges from about 1 micromolar to about 1 millimolar in the reaction mixture.

In another aspect of this embodiment of the invention, the effective amount of the inhibitor ranges from about 1 micromolar and about 500 micromolar in the reaction mixture.

In another aspect of this embodiment of the invention, the effective amount of the inhibitor ranges from about 10 micromolar to about 200 micromolar in the reaction mixture.

In another aspect of this embodiment of the invention, the effective amount of the inhibitor ranges is about 100 micromolar in the reaction mixture.

BRIEF DESCRIPTION OF THE DRAWINGS

FIG. 1. Luminescent CYP450 reaction scheme.

FIG. 2. Structures: D-luciferin ((4S)-4,5-dihydro-2-(6-hydroxy-benzothiazolyl)-4-thiazolecarboxylic acid) and D-luciferin derivatives.

FIG. 9. Two-step detection of CYP450 de-picolinylase activity. D-luciferin derivatives luc2PE, luc3PE, and luc4PE were incubated in a CYP450 reaction mix for 60 minutes at 37° C. before combining with a luciferase reaction mixture. In this Figure, the bars labeled "Sf9" are the controls. These are Sf9 cell membranes without CYP450 expression. Luminescence was read within 12 minutes of combining the reactions on a Berthold Orion luminometer.

DETAILED DESCRIPTION OF THE INVENTION

Figure 3A:
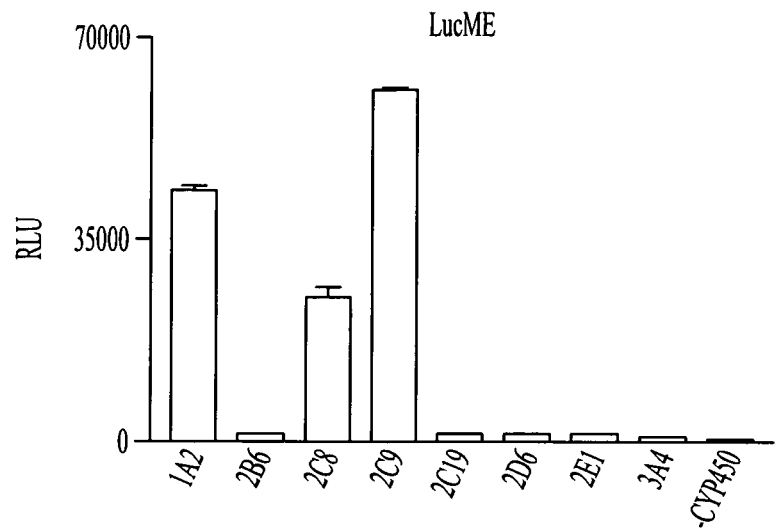
FIG. 3. Two-step luminescent CYP450 reactions. D-luciferin derivatives were incubated in a CYP450 reaction mix for 60 minutes at 37° C. before combining with a luciferase reaction mixture. In —CYP450 controls, CYP450 Sf9 cell microsomes were replaced with control (no CYP450) Sf9 cell membranes (panels B, C, D and E) or H₂O (panel A) or both (panel F, G, H, and I). Luminescence was read within 12 minutes of combining the reactions on a Turner Reporter (panels A, B, C and E) or Berthold Orion (panels D, F, G, and H) luminometer.
Figure 3B:
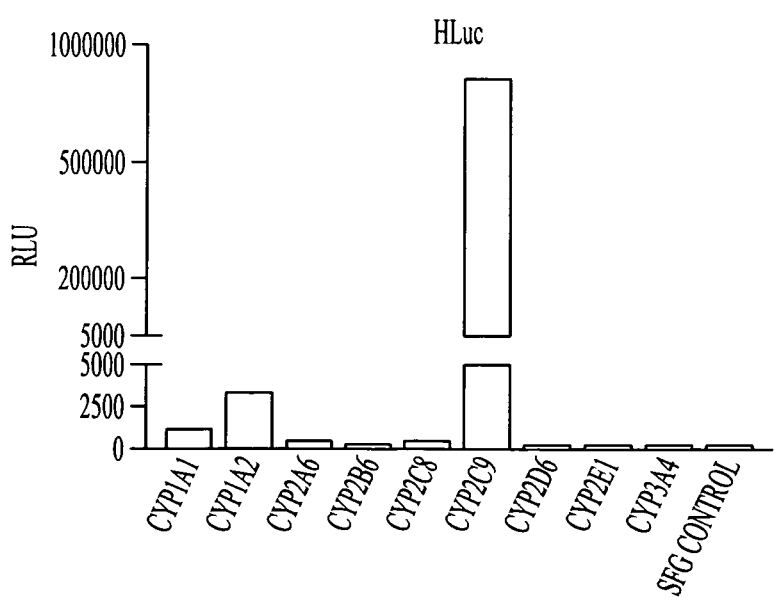
Figure 3C:
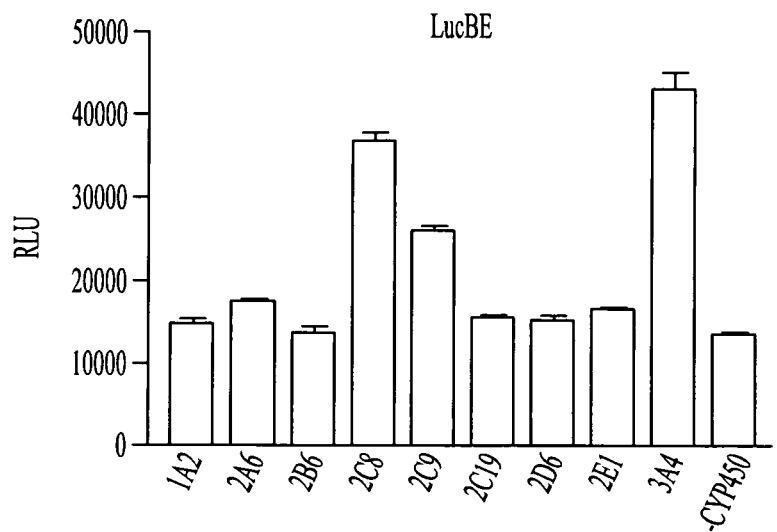
Figure 3D:
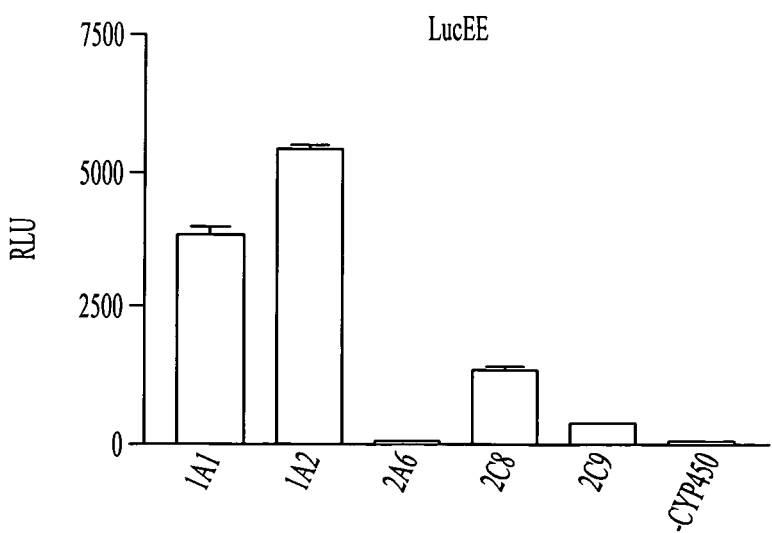
Figure 3E:
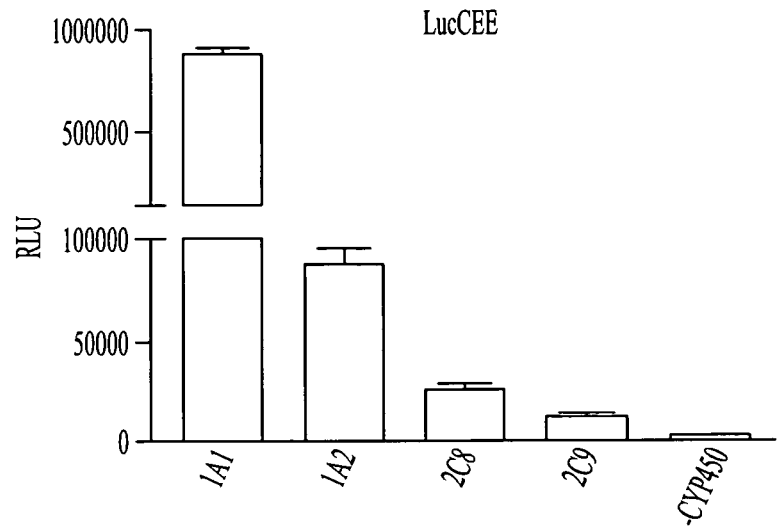
Figure 3F:
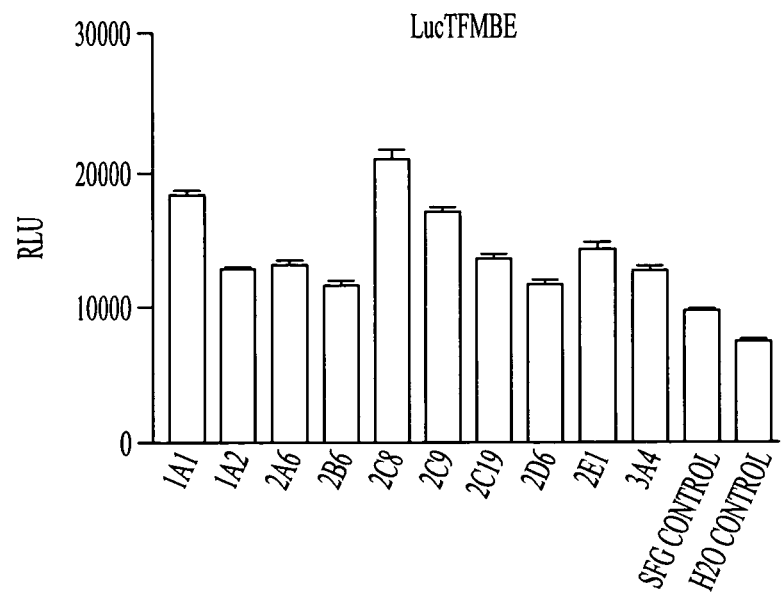
Figure 3G:
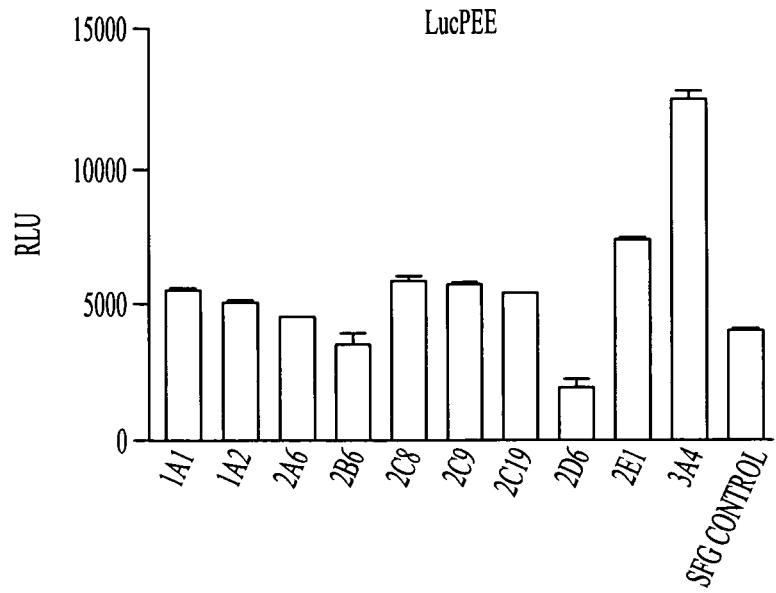
Figure 3H:
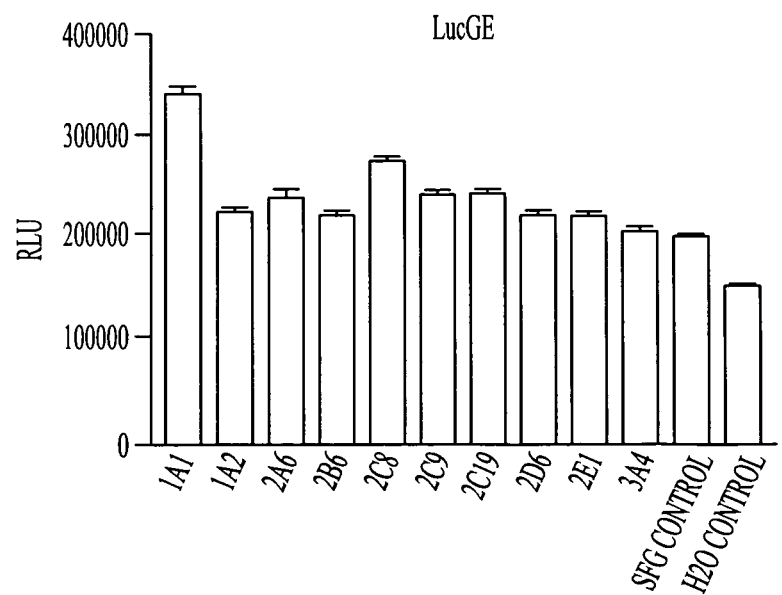
Figure 3I:
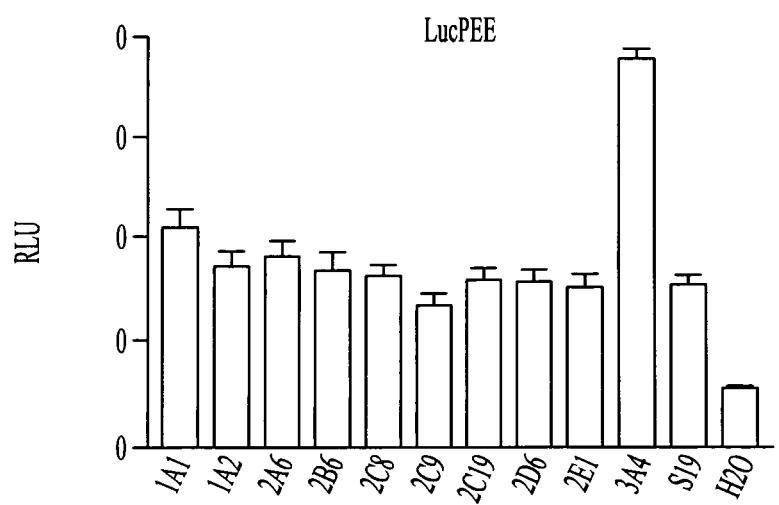

As defined herein, the term "cytochrome P450" or "CYP450" or "P450 enzyme," unless specified otherwise, refers to a family of heme-based oxidase enzymes involved in the metabolism of hydrophobic drugs, carcinogens, and other potentially toxic compounds and metabolites circulating in blood. It is known that the liver is the major organ for xenobiotic metabolism, containing high levels of the most important CYP450 mixed-function oxidases. These mixed-function oxidases are divided into subfamilies, which include CYP1A, 2A, 2C, 2D, 2E, and 3A. Within these subfamilies, there are numerous human P450 enzymes, often termed "isozymes" or "isoforms." The human CYP3A, CYP2D6, CYP2C, and CYP1A isoforms are known to be important in drug metabolism. See, e.g., Murray, M., 23 Clin. Pharmacokinetics 132-46 (1992). CYP3A4 is by far the major isoform in human liver and the small intestines, comprising 30% and 70% respectively of the total CYP450 protein in those tissues. Based primarily on in vitro studies, it has been estimated that the metabolism of 40% to 50% of all drugs used in humans involve CYP3A4 catalyzed oxidations. See Thummel, K. E. & Wilkinson, G. R., In Vitro and In Vivo Drug Interactions Involving Human CYP 3A, 38 Ann. Rev. Pharmacol. Toxicol., 389-430 (1998).

The term "luminescent", as used herein, includes bio-luminescence (i.e. light produced by a living organism), or chemi-luminescence (light produced when a chemical reaction proceeds). When the enzyme involved has evolved in an organism by natural selection for the purpose of generating light, or the enzyme involved is a mutated derivative of such an enzyme, the luminescent reactions are also called "bioluminescent reactions" and the enzyme involved is also called a "bioluminescent enzyme." Examples of bioluminescent enzymes include, without limitation, firefly luciferase, *Renilla* luciferase, *Cypridina* luciferase, *Aequorin* photoprotein, *Obelin* photoprotein, and the like.

The term "luminogenic molecule" as used herein refers to a molecule capable of creating light via a chemical or biochemical reaction (e.g. beetle luciferin (or D-luciferin), coelenterazine, or a functional analog thereof). The luminogenic molecule could be either a P450 substrate or a P450 substrate/bioluminescent enzyme pro-substrate. Generally, a luminogenic molecule is either a high-energy molecular species (e.g. a stabilized dioxetane), or it is transformed into a high-energy molecular species by a chemical reaction. The chemical reaction is usually oxidation by oxygen, superoxide, or peroxide. In each case, the energy within the luminogenic molecule is released by the chemical reaction. Although at least some of this energy is released as photons of light, the energy can also be released in other forms, such as heat. The luminogenic molecules that do not yield light disperse their energy through alternative modes, often termed "dark pathways".

The term "luciferin derivative" as used herein refers to a type of luminogenic molecule or compound having a substantial structure of D-luciferin and maybe a substrate of one or more cytochrome P450 enzymes and a pro-substrate of luciferase. In the presence of cytochrome P450, the compound is metabolized into luciferin, a substrate of luciferase. In the absence of prior P450 metabolism, some of the compound(s) may bind to luciferase as evidenced by their capacity to inhibit a reaction with luciferin (data not shown), however, they are not turned over as substrate in light-generating reactions. Without being bound by any theory of operation, it is believed that these compounds are most likely competitive inhibitors of luciferase.

The term "coelenterazines" as used herein refers to natural coelenterazines and coelenterazine derivatives. Coelenterazines are known to luminesce when acted upon by a wide variety of bioluminescent proteins, specifically marine luciferases. Examples of marine luciferases include *Renilla* luciferase, aequorin, *Gaussia* luciferase, *Oplophorus* luciferase, and *Cypridina* luciferase. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

The term "luciferase," unless specified otherwise, refers to a naturally occurring or mutant luciferase. The luciferase, if naturally occurring, may be obtained easily by the skilled from an organism. If the luciferase is one that occurs naturally or is a mutant, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding same. Luciferases are available from Promega Corporation, Madison, Wis.

The term "pyrophosphatase," unless specified otherwise, refers to any agent such as an enzyme (naturally occurring or mutant) that is capable of breaking down or hydrolyzing pyrophosphate that is generated during the course of a reaction, already present in the reaction mixture, or introduced into a reaction mixture. The agent should be added at a concentration sufficient to either catalyze the hydrolysis of pyrophosphate in the reaction mixture at a rate that will prevent accumulation of pyrophosphate or prevent accumulation of pyrophosphate in any other manner. The amount of agent needed is readily determined by standard procedures. While inorganic pyrophosphatases (hydrolyases) are preferred agents in practicing this invention, there are many enzyme types (e.g., transferases, kinases, and synthetases) that may also be used in the practice of the invention. See, for example, U.S. Pat. No. 6,291,164 which is incorporated by reference in its entirety. A number of such enzymes have been cloned and expressed in a recombinant host. See, for example, Ladror, U. S. et al., J. Biol. Chem. 266:16550-16555 (1991) (Pyrophosphate: fructose-6-phosphate 1-phosphotransferase); Leyh, T. S. et al., J. Biol. Chem. 263:2409-2416 (1988) (ATP: sulfate adenylyltransferase); Leyh, T. S. et al., J. Biol. Chem. 267: 10405-10410 (1992) (ATP: sulfate adenylyltransferase); Weissbom, A. C., et al., J. Bacteriology 176:2611-2618 (1994) (UTP:glucose-1-phosphate uridylyltransferase); Allen, T. et al., Mol. Biochem. Parasitol. 74:99 (1995) (Adenine phosphoribosyltransferase); Vonstein, V. et al., J. Bacteriol. 177:4540 (1995) (Orotate phosphotibosyltransferase); Charng, Y. Y. et al., Plant Mol. Biol. 20:37 (1992) (Glucose-1-phosphate adenylyltransferase); Kim, D. J. and Smith, S. M., Plant Mol. Biol. 26:423 (1994) (Phosphoenolpyruvate carboxykinase); Jiang, Y. et al., Exp. Parasitol. 82:73 (1996) (Hypoxanthine-guanine phosphoribosyltransferase); Pla, J. et al., Gene 165:115 (1995) (ATP phosphoribosyltransferase); Feldman, R. C. et al., Infect. Immun. 60:166 (1992) (Uracil phosphoribosyltransferase); Vinitsky, A., J. Bacteriol. 173:536 (1991) (Micotinate phosphoribosyltransferase); Ludin, K. M. et al., Curr. Genet. 25:465 (1994) (Amidophosphoribosyltransferase); Rose, A. B. et al., Plant Physiol. 100: 582 (1992) (Anthranilate phosphoribosyltransferase); Hughes, K. T. et al., J. Bacteriol. 175:479 (1993) (Quinolate phosphoribosyltransferase); Jagadeeswaran, P. et al., Gene 31:309 (1984) (Xanthine-guanine phosphoribosyltransferase); Nakagawa, S., Biosci. Biotech. Biochem. 59:694 (1995) (FMN adenylyltransferase); Marolda, C. L. and Valvano, M. A., J. Bacteriol. 175:148 (1993) (Mannose-1-phosphate guanylyltransferase); Kalmar, G. B., Proc. Natl. Acad. Sci. USA 87:6029 (1990) (Choline phosphate cytidylyltransferase); Muller-Rober, B. et al., Plant Mol. Biol. 27:191 (1995) (Glucose-1-phosphate adenylyltransferase); Sharmugam, K. et al., Plant Mol. Biol. 30:281 (1996) (tRNA nucleotidyltransferase); Zapata, G. A. et al., J. Biol. Chem. 264:14769 (1989) (Acylneuraminate cytidylyltransferase); and Vakylenko, S. B. et al., Antiobiot. Khimioter. 38:25 (1993) (Gentamycin 2'-nucleotidyltransferase). If such enzymes are used, it may be necessary to also employ a substrate which is capable of either accepting a phosphate radical to give a phosphorylated product from pyrophosphate or effecting transfer of a pyrophosphate radical when in the presence of the enzyme.

In one embodiment of the invention, luciferin derivatives are provided that are substrates of CYP450 and are pro-substrates of luciferase. When these luciferin derivatives are exposed to certain CYP450 isoforms, these isoforms metabolize the derivatives into compounds that can be readily detected in a light-emitting reaction in the presence of the enzyme luciferase. In the absence of CYP450, the luciferin derivatives may bind to luciferase, however they are not turned over as substrate in light-generating reactions. In practicing the invention, the luciferin derivatives of the invention preferably have the following formula:

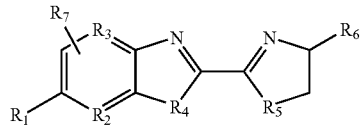

wherein $R_1$ represents hydrogen, hydroxyl, amino, $C_{1-20}$ alkoxy, substituted $C_{1-20}$ substituted alkoxy, $C_{2-20}$ alkenyloxy, $C_{2-20}$ substituted alkenyloxy, $C_{1-20}$ halogenated alkoxy, $C_{1-20}$ substituted halogenated alkoxy, $C_{3-20}$ alkynyloxy, $C_{3-20}$ substituted alkynyloxy, cycloalkoxy, substituted cycloalkoxy, cycloalkylamino, substituted cycloalkylamino, $C_{1-20}$ alkylamino, $C_{1-20}$ substituted alkylamino, $C_{1-20}$ substituted alkylamino $C_{1-20}$ dialkylamino, or $C_{1-20}$ substituted dialkylamino, $C_{2-20}$ alkenylamino, $C_{2-20}$ substituted alkenylamino, $C_{2-20}$ dialkenylamino, $C_{2-20}$ substituted dialkenylamino, $C_{2-20}$ alkenylalkylamino, or $C_{2-20}$ substituted alkenylalkylamino, $C_{3-20}$ alkynylamino, $C_{3-20}$ substituted alkynylamino, $C_{3-20}$ dialkynylamino, $C_{3-20}$ substituted dialkynylamino, $C_{3-20}$ alkynylalkylamino, $C_{3-20}$ substituted alkynylalkylamino, $C_{3-20}$ alkynylalkenyl amino, or $C_{3-20}$ substituted alkynylalkenylamino;

$R_2$ and $R_3$ independently represents C or N;

$R_4$ and $R_5$ independently represents S; O; $NR_5$ wherein $R_8$ represents hydrogen or $C_{1-20}$alkyl; $CR_9R_{10}$ wherein $R_9$ and $R_{10}$ independently represent H, $C_{1-20}$ alkyl, or fluorine;

$R_6$ represents $COR_{11}$ wherein $R_{11}$ represents H, OH, $C_{1-20}$ alkoxide, $C_{2-20}$ alkenyl, $CH_2OH$, or $NR_{12}R_{13}$ wherein $R_{12}$ and $R_{13}$ are independently H or $C_{1-20}$ alkyl; and $R_7$ represents H, $C_{1-6}$ alkyl, $C_{1-20}$ alkenyl, halogen, or $C_{1-6}$ alkoxide.

In practicing this invention, particularly preferred luciferin derivatives include luciferin 6' methyl ether (Luc ME), luciferin 6' ethyl ether (Luc EE), luciferin 6' chloroethyl ether (Luc CEE), luciferin 6' benzyl ether (Luc BE), luciferin 6' 3-picolinyl ether (Luc 3PE) and 6' deoxyluciferin (H Luc).

In another embodiment of the invention, a method is provided for measuring the activity of a cytochrome P450 enzyme. A luminogenic molecule that is a P450 substrate and a bioluminescent enzyme pro-substrate is contacted with one or more cytochrome P450 enzymes and bioluminescent enzyme, either simultaneously or in a stepwise manner, for a predetermined time. In the presence of P450, the luminogenic molecule is metabolized into a substrate for the bioluminescent enzyme in a first reaction. The bioluminescent enzyme then acts on the substrate in a second light emitting reaction. Cytochrome P450 activity is determined by measuring the amount of luminescence that is generated from reaction mixture relative to a control (e.g., no P450 enzyme). For the P450 reaction to occur, P450 reductase, NADPH and $Mg^{+2}$ are generally present in the system. Similarly, the presence of ATP and $Mg^{+2}$ is generally necessary for firefly luciferase activity but not for Renilla luciferase activity. Any suitable concentration of luminogenic molecule may be employed in the reaction mixture. In practicing this invention, the concentration of the luminogenic molecule generally ranges between about 10 nM to 1 mM, preferably in the linear range of the substrate dose response by a particular P450 isoform, most preferably at the Km for the particular substrate/P450 isoform reaction or at Vmax for that reaction.

The invention also provides a method for determining P450 activity based on luminogenic molecules that are natural coelenterazine and coelenterazine derivatives (collectively referred to as coelenterazines). The P450 acts on these luminogenic molecules in one of two ways. In one reaction pathway, the luminogenic molecules are P450 substrates and bioluminescent enzyme pro-substrates and do not exhibit the characteristic coelenterazine chemiluminescent (luminescence in the absence of a bioluminescent enzyme, e.g. *Renilla*-type luciferase). P450 metabolism of the luminogenic molecule in a first reaction generates the substrate for the *Renilla* luciferase. The *Renilla* luciferase then acts on the substrate in a second light-emitting reaction. P450 activity is then ascertained by measuring the luminescence of the reaction mixture relative to a control reaction mixture. In the second reaction pathway, coelenterazine or coelenterazine derivatives exhibit chemiluminescence and are substrates for *Renilla*-type luciferase. P450 metabolism of such a luminogenic molecule results in the loss of chemiluminescence and activity with *Renilla*-type luciferase. In both types of reaction pathways, P450 activity may be detected either directly by a change in chemiluminescence by the action of the P450 alone or indirectly by a change in bioluminescence from a *Renilla*-type luciferase. Useful, but non-limiting, coelenterazines are disclosed in U.S. patent application Ser. No. 10/053,482, filed Nov. 2, 2001, the disclosure which is hereby incorporated by reference in its entirety.

Luciferases differ somewhat in the ranges of conditions, of pH, ionic strength, temperature, ATP concentration, magnesium ion concentration, luciferin concentration, and the like, over which they are active in the luciferase-luciferin reaction. Likewise, cytochrome P450 enzymes differ somewhat in the ranges of conditions, of pH, ionic strength, temperature, cofactor requirements, substrate concentration, and the like, over which they are active in. It is, however, a simple matter for a skilled artisan to ascertain such ranges, and even the optimum ranges, for any particular luciferase and any particular cytochrome P450 enzyme. In practicing this invention, the amount of luciferase enzyme that may be employed in a reaction mixture generally ranges between about 0.1 microgram/mL to about 200 microgram/mL, preferably about 0.5 microgram/mL to about 100 microgram/mL. The amount of P450 enzyme that may be employed in a reaction mixture generally ranges between about 0.1 picomoles to about 200 picomoles, preferably about 0.4 to about 80.0 picomoles.

The skilled artisan is also aware that compositions other than those specifically recited above will be or may be present in any assay reaction mixture, in order to, for example, maintain or enhance the activity of the enzyme or as a consequence of the procedures used to obtain the aliquot of sample being subjected to the assay procedures. Thus, typically buffering agents, such as Tricine, HEPPS, HEPES, MOPS, Tris, glycylglycine, a phosphate salt, or the like, will be present to maintain pH and ionic strength; a proteinaceous material, such as a mammalian serum albumin (preferably bovine serum albumin) or lactalbumin or an ovalbumin, that enhances the activity of luciferases in the luciferase-luciferin reaction, may be present; EDTA or CDTA (cyclohexylenediaminetetraacetate) or the like, may be present, to suppress the activity of metal-containing proteases or phosphatases that might be present in systems (e.g., cells) from which luciferase to be assayed is extracted and that could adversely affect the luciferase or the ATP. Glycerol or ethylene glycol, which stabilize luciferases, might be present. Similarly, detergents or surfactants, particularly non-ionic detergents, such as those of octoxynol (e.g., sold under the trademark "Triton X" of Rohm & Haas, such as Triton X-100) might be included, typically as remnants, carried into a solution used in an assay according to the invention, of a solution used to lyse cells from which luciferase is extracted for the assay. Counterions to the magnesium will, of course, be present; as the skilled will understand, the chemical identities and concentrations of these counterions can vary widely, depending on the magnesium salt used to provide the magnesium ion, the buffer employed, the pH of the solution, the substance (acid or base) used to adjust the pH, and the anions present in the solution from sources other than the magnesium salt, buffer, and acid or base used to adjust pH. In practicing this invention, $MgSO_4$ or $MgCl_2$ are the preferred sources of magnesium ion. In one procedure, the magnesium ion can be supplied as the carbonate salt, to provide the desired magnesium ion concentration, in a solution with the buffer to be used (e.g., Tricine) and then the pH of the buffered solution can be adjusted by addition of a strong acid, such as sulfuric, which will result in loss of most of the carbonate (and bicarbonate) as carbon dioxide and replacement of these anions with sulfate, bisulfate, Tricine anion, and possibly also other types of anions (depending on other substances (e.g., phosphate salts) that provide anions and might be present in the solution). Oxygen-diffusion from the air into the solution in which the assay method is carried out is sufficient to provide the molecular oxygen required in the P450 and luciferase-luciferin reactions. In any case, it is well within the skill of the ordinarily skilled to readily ascertain the concentrations of the various components in an assay reaction mixture, including the components specifically recited above in the description of the method, that are effective for activity of the P450 enzyme in the P450 reaction and luciferase in the luciferase-luciferin reaction.

The luminescence of the luciferin-luciferase reaction may be measured using a commercially available luminometer, a scintillation counter, a photomultiplier photometer or a photoemulsion film. In one aspect of this invention, a one-step method for measuring P450 activity is provided.

In the one-step method, the luminogenic molecule is contacted with both the cytochrome P450 enzyme and the bioluminescent enzyme simultaneously or contemporaneously and the mixture is allowed to incubate for a predetermined time period. The cytochrome P450 metabolizes the luminogenic molecule into a substate for the bioluminescent enzyme in a first reaction. The bioluminescent enzyme then acts on the substate in a second light emitting reaction. Cytochrome P450 activity is indirectly determined by measuring the amount of luminescence that is generated from the assay mixture relative to a control mixture. Controls may involve replacement of P450 enzyme with water or the P450 buffer, replacement of recombinant P450 membrane preparation with a similar preparation that lacks P450 enzyme, elimination of NADPH, or heat denaturation of P450 enzyme prior to addition of the luciferin substrate. Luminescence can be measured after a predetermined incubation time period or continuously from the time the reaction is initiated. For instance, the assay results shown in FIGS. 6 and 7 were read continuously from the time the reaction was initiated.

In another and preferred aspect of this invention, a two-step method for measuring P450 activity is provided. In the two-step method, the luminogenic molecule is first incubated with the cytochrome P450 enzyme for a first predetermined time period. The P450 enzyme metabolizes the luminogenic molecule and converts it into a substrate for the bioluminescent enzyme. Thereafter, the reaction mixture containing the P450 enzyme and substrate is contacted with a bioluminescent, e.g., luciferase, enzyme for a second predetermined time period. The bioluminescent enzyme acts on the substrate in a second light emitting reaction. Cytochrome P450 activity is then indirectly determined by measuring the amount of luminescence that is generated from the reaction mixture relative to a control (e.g., no active P450 enzyme).

In practicing this aspect of the invention, a detergent, preferably non-ionic, is preferably added to the P450/luminogenic molecule mixture just prior to or at the same time as contact with the bioluminescent, e.g., luciferase, enzyme in the second step of the two-step reaction system. The detergent quenches the P450 enzyme without interfering with the luciferase enzyme, thus allowing the analyst to measure luciferin (or luciferin derivative metabolite(s)) concentration dependent luminescence at the time of stopping the reaction without the complexity of having luciferin continuously added to the pool by an active P450 enzyme. Moreover, the non-ionic detergent stimulates the luciferase and results in a somewhat brighter reaction. In the case where a test compound such as a drug is a luciferase inhibitor, the non-ionic detergent diminishes the inhibitory effect on the luciferase and thus offers an advantage to the analyst who is interested only in the effects of the test compound on P450 activity. Suitable, but non-limiting, detergents include Tergitol (non-ionic); Brij 35 (non-ionic); Brij 58 (non-ionic); Polymixin B; Triton X-100 (non-ionic); Triton X-305 (non-ionic); Triton N101 (non-ionic); Chaps (zwitterionic); Chapso (zwitterionic); Bigchap (non-ionic); Thesit (non-ionic); Pluronic L64 (non-ionic); Rhodasurf 870; Chemal LA-9; Sulfonyl 465; Deoxycholate (anionic); and CTAB (cationic). In practicing this invention, Tergitol type NP-9, a polyglycol ether non-ionic surfactant, is preferred. The amount of detergent present in the assay mixture generally ranges between about 0.03% to about 2.0%, preferably between about 0.1% to about 1.0%.

For the one-step system and the first step of the two-step reaction systems, the reaction mixture generally included the following components: 25 mM $KPO_4$ at pH 7.4 for CYP2C9, 100 mM $KPO_4$ at pH 7.4 for CYP1A2 etc. Other components were 1.3 mM NADP+, 3.3 mM glucose-6-phosphate, 0.4 units/mL glucose-6-phosphate dehydrogenase, 3.7 mM $MgCl_2$. For the one-step system, 200 micromolar ATP is also used. For the second step (luciferase reaction) of the two-step system, 5 mM to 200 mM Tricine buffer, preferably 20 mM to 200 mM Tricine buffer, is used although HEPES, HEPPS, MOPS, Phosphate, and Bicine buffers are also useful. Other components include 0.7 mM to 7.1 mM $MgSO_4$ (or $MgCl_2$), and 0.1 micromolar to 1 mM, preferably 10 micromolar to 250 micromolar, ATP. For the one-step system and the first step of the two-step reaction system, the reactions are generally carried out at about 20° to 42° C., preferably about 22° to 37° C. For the second step of the two-step reaction system, the reactions are generally carried out at a temperature of about 4° to 60° C., preferably about 200 to 42° C. While any suitable predetermined time may be used for the one-step or two-step reaction systems, the predetermined time for the one-step reaction system and the first step of the two-step reaction system generally ranges between about 1 minute to about 18 hours, usually about 1 minute to about 4 hours (for the one step reaction system) or about 10 minutes to about 1 hour (for the first step of the two-step reaction system). For the second step of the two-step reaction system, luminescence is determined immediately to about 18 hours, preferably immediately to about 3 hours after initiation of the luciferase reaction.

In another aspect of this invention, a reagent, method and kit for stabilizing luminescence-based reactions is provided. It has been discovered that the use of certain luciferase stabilizing molecules such as reversible inhibitors of luciferase may provide a protective effect against the known self-catalyzed auto-degradation of the luciferase enzyme, thus prolonging the luminescence signal and facilitating batch processing of reaction mixtures. As defined herein, a luciferase stabilizing agent is any molecule or group of molecules that substantially stabilizes luciferase against self-catalyzed auto-degradation of luciferase by slowing down the bioluminescence reaction. Without the stabilizing agent, the luminescent signal half-life may be as low as a few minutes, e.g., about three minutes. When stabilizing agent is used, the signal half-life of the luciferased based reaction can be extended by as long as two hours or longer including overnight, depending on the choice of stabilizing agent and the concentration used. Examples of luciferase stabilizing molecules include, without limitation, reversible inhibitors of luciferase. Bioluminescent signals may decay rapidly, especially in the case where a firefly luciferase is used. These enzymes are known to inactivate at a rate that is positively correlated with the luminogenic reaction rate. While bright signals resulting from rapid luciferase reaction rates may be desirable, the rapid inactivation at high rates imposes a practical limitation on the assay. A stable luminescent signal would facilitate reading multiple samples in sequence without a significant time-dependent decay between samples. To achieve a stable luminescent signal, it is possible to slow the reaction rate and thereby diminish rate of signal decay. One method for slowing the luciferase reaction rate is to include a luciferase inhibitor that is competitive with luciferin. In this invention, 2-amino-6-methylbenzothiazole (AMBT) or 2-(4-aminophenyl)-6-methylbenzothiazole (APMBT), both competive inhibitors of firefly luciferase, were found to be particularly useful in achieving a stable luminescent signal. Generally, the luciferase stabilizing agent is introduced after the completion of the P450 reaction and may be introduced prior to or at the start of the second step of two-step luminescent CYP450 assays.

In practicing this aspect of the invention, any suitable amount of luciferase inhibitor may be used that is effective to enhance the stability and prolong the lifetime of the luminescent signal relative to the luminescent signal generated in a comparable luciferase-based reaction mixture in the absence of the inhibitor. Preferably the amount of inhibitor should be such that the signal half-life is at least about two hours or more to allow for sample batch processing. Generally, the amount of the inhibitor ranges from about 1 micromolar to about 1 millimolar in the reaction mixture, preferably from about 1 micromolar and about 500 micromolar in the reaction mixture, more preferably from about 10 micromolar to about 200 micromolar in the reaction mixture, and most preferably about 100 micromolar in the reaction mixture.

In another embodiment of the invention, test compounds such as candidate drugs can be screened and evaluated for their activities as substrates of or regulators, either inhibitors or activators of a cytochrome P450 enzyme by using the luminogenic molecules, e.g. luciferin derivatives of the present invention. A candidate drug may be determined to be regulator or a substrate of a cytochrome P450 enzyme by contacting a cytochrome P450 enzyme with the candidate drug, under conditions suitable for interaction therebetween, providing at least one luciferin derivative, under conditions that would, in the absence of an inhibitor or substrate of the cytochrome P450 enzyme, be suitable for interaction with the cytochrome P450 enzyme, and detecting the presence of luminescent signal of luciferin and/or a luciferin derivative metabolite in the presence of the luciferase, wherein luciferin and/or a luciferin derivative metabolite would be, in the absence of an inhibitor of the cytochrome P450 enzyme, the product of the reaction between the cytochrome P450 enzyme and the luciferin derivative. Such efficient P450 substrates and regulators, as deemed appropriate by those of skill in the art, may be removed from a screening library where such efficient cytochrome P450 substrates and regulators are not desired in the remainder of the screening for a candidate drug.

In one aspect of the invention, a method is provided to distinguish between a substrate and an inhibitor of cytochrome P450 enzymes. Typically, the candidate compound is incubated with at least one cytochrome P450 enzyme under conditions, which allow for metabolism of the candidate compound prior to providing the luminogenic molecule, e.g., luciferin derivative, under conditions that would, in the absence of an inhibitor or substrate of the cytochrome P450 enzyme, be suitable for interaction between the luciferin derivative and the cytochrome P450 enzyme. Any luciferin produced by the P450 metabolism of the luciferin derivative would then interact with luciferase in a light-emitting second reaction. The resulting light emitting reaction is compared to the one obtained from contacting a cytochrome P450 enzyme with the candidate drug, under conditions suitable for interaction therebetween, providing at least one luciferin derivative, under conditions that would, in the absence of an inhibitor of the cytochrome P450 enzyme, be suitable for interaction between the luciferin derivative and the cytochrome P450 enzyme. Metabolism of the candidate drug by a cytochrome P450 enzyme reduces its concentration in the assay medium and may lead to an apparent loss of cytochrome P450 inhibitory activity compared to conditions without metabolism of the compound which would indicate it was a substrate for the enzyme. An inhibitory compound that was not metabolized would show equal potency, irrespective of the time of addition of the optical cytochrome p450 enzyme substrate.

In another aspect of the invention, the drug candidate is preferably contacted first with the P450 enzyme for a first predetermined time period. Thereafter, the mixture is contacted with the luminogenic molecule, e.g., luciferin derivative and bioluminescent enzyme, e.g., luciferase, simultaneously or contemporaneously and the mixture is allowed to incubate for a second predetermined time period. Cytochrome P450 activity is determined by measuring the amount of luminescence that is generated from the reaction mixture relative to a control (e.g., no P450 enzyme).

In yet another (and preferred) aspect of the invention, the drug candidate is preferably incubated first with the P450 enzyme for a first predetermined time period to form a first mixture. Thereafter, the first mixture is contacted with the luminogenic molecule, e.g., luciferin derivative, to form a second mixture that is allowed to incubate for a second predetermined time period. The second mixture is then contacted with a bioluminescent enzyme, e.g., luciferase, to form a third mixture which is allowed to incubate for a third predetermined time period. Thereafter, the P450 activity resulting from the interaction of the enzyme with the drug candidate is determined by measuring luminescence after the third predetermined time period relative to a control (e.g., no drug) reaction.

Any suitable concentration ranges for compound screenings may be used in practicing this invention. For primary library screening, the concentration of test compounds used generally ranges from about 1 to about 100 micromolar, usually about 10 micromolar. Secondary and further screens of primary hit test compounds generally employ wider ranges to establish the dose dependency of the response and depends, in part, on the potency of the test compound.

In practicing this aspect of the invention, non-ionic detergent is preferably added to the second mixture prior to the addition of luciferase in order to denature or deactivate the P450 enzyme. Suitable detergents and amounts are described above.

In another embodiment of the invention, a high throughput assay method is provided for screening a plurality of compounds to determine their effect on cytochrome P450 activity. The test compounds are contacted with one or more types of P450 enzymes, the luminogenic molecule, e.g., luciferin derivative, and bioluminescent enzyme, e.g., luciferase, for a predetermined period of time. Thereafter, the P450 activity resulting from the interaction of the P450 enzyme with the compounds are determined by measuring luminescence.

In one aspect of the invention, the compounds are preferably contacted first with the P450 enzymes for a first predetermined time period. Thereafter, the mixture is contacted with the luminogenic molecule, e.g., luciferin derivative and bioluminescent enzyme, e.g., luciferase simultaneously or contemporaneously and the mixture is allowed to incubate for a second predetermined time period. Cytochrome P450 activity is determined by measuring the amount of luminescence that is generated after the second predetermined time period relative to a control (e.g., non-P450 enzyme) reaction. In another (and preferred) aspect of the invention, the compounds are preferably contacted first with the P450 enzymes for a first predetermined time period to form first mixtures. Thereafter, the first mixtures are contacted with the luciferin derivative to form second mixtures that are allowed to incubate a second predetermined time period. The second mixtures are then contacted with luciferase to form a third mixture which is allowed to incubate for a third predetermined time period. Thereafter, the P450 activities resulting from the interaction of the enzyme with the test compounds are determined by measuring luminescence of the reaction mixture relative to a control (e.g., no P450 enzyme) reaction mixture. In practicing this aspect of the invention, non-ionic detergent is preferably added to the second mixture prior to the addition of luciferase. Suitable detergents and amounts are described above.

For compound screening, P450 is contacted first with the test compound for a predetermined time period prior to addition of the luminogenic molecule, e.g., luciferin derivative. Another approach would involve contacting the P450 with the drug and luciferin simultaneously. Yet another approach would involve contacting the P450 with the luciferin first for a predetermined time period prior to addition of the test compound.

In another embodiment of the invention, a cell-based method is provided for screening test compound to determine its effect on cytochrome P450 activity of the cell. The test compound is contacted with a cell, the luminogenic molecule, e.g., luciferin derivative, and bioluminescent enzyme, e.g., luciferase, for a predetermined period of time. Thereafter, the P450 activity resulting from the interaction of the cell with the compound is determined by measuring luminescence of the reaction mixture relative to a control (minus test compound) reaction mixture.

In one aspect of the invention, the compound is preferably contacted first with the cell for a predetermined time period. Thereafter, the cell is contacted with the luciferin derivative and luciferase simultaneously or contemporaneously and the cell is allowed to incubate with the derivative and luciferase for a second predetermined time period. Cytochrome P450 activity of the cell is determined by measuring the amount of luminescence generated from the reaction mixture relative to a control reaction mixture (e.g., minus test compound). In another (and preferred) aspect of the invention, the test compound is preferably contacted first with the cell for a predetermined time period. Thereafter, the exposed cell is then contacted with the luciferin derivative and incubated for a second predetermined time period. The cell is then contacted with luciferase to form a third mixture which is allowed to incubate for a third predetermined time period. Thereafter, the P450 activity of the cell resulting from the interaction of the cell with the test compounds are determined by measuring luminescence of the reaction mixture relative to a control reaction mixture (e.g., minus test compound). In practicing this aspect of the invention, non-ionic detergent is preferably added to the second mixture prior to or at the same time as the addition of luciferase to ensure more complete release of luciferin or luciferin derivative metabolites(s), resulting in a stronger signal and a more sensitive assay. Detergent will rupture the cells and release luciferin. In the absence of detergent, however, luciferin or luciferin derivative metabolite(s) may leak out of the cell due to its cell permeability and this would form the basis for a real-time live cell assay with luciferase and ATP in the medium. Suitable detergents and concentration ranges are described above.

In practicing this aspect of the invention, suitable cells would include any cell that expresses one or more P450 enzymes and its requisite cofactors such as P450 reductase that utilizes the luciferin derivatives. Such cells can be used to examine the effects of test compounds on CYP450 enzyme activities present in the cell at the time the test compound is applied. The cells can also be used to examine the effects of test compounds on the expression of endogenous CYP450 genes or transgenes that encode CYP450s with gene regulatory sequences. In this case test compound-induced changes in gene expression can be detected by measuring changes in the level of p450 enzyme activity. Representative examples include: (a) Primary hepatocytes from human or animal sources (commercially available from several sources: Gentest, Woburn, Mass.; Clonetics, Inc., San Diego, Calif.; Xenotech LLC, Lenexa, Kans.); (b) Hepatocytic cell lines: HepG2, HepG2C3A. Commercially available from Amphioxus Cell Technologies Inc. (Houston, Tex.) and from American Type Culture Collection (ATCC), THLE-3 Commercially available from ATCC, HepLiu porcine hepatocyte line, commercially available from MultiCell Technologies (Warwick, R.I.), and BC2 human hepatoma cell line (Gomez-Lechon, M. J. et al (2001) "Expression and induction of a large set of drug-metabolizing enzymes by the highly differentiated human hepatoma cell line BC2", *Eur. J. Biochem.* 268, 1448-1459); (c) Cells expressing recombinant P450s such as: HepG2 (Yoshitomi, S. et al (2001) "Establishment of the transformants expressing human cytochrome P450 subtypes in HepG2, and their applications on drug metabolism and toxicology", *Toxicol. In Vitro* 15(3), 245-256), Chinese hamster ovary (CHO) cells (Gabelova, A. et al (2002) "Mutagenicity of 7H-dibenzo(c,g)carbazole and its tissue specific derivatives in genetically engineered Chinese hamster V79 cell lines stably expressing cytochrome p450", *Mutation Research*, 517(1-2), 135-145), BEAS-2B, SV40 immortalized human bronchial epithelial cells (Coulombe, R. A. et al (2002) "Metabolism and cytotoxicity of aflatoxin B1 in cytochrome P450-expressing human lung cells" *J. Toxicol. Env. Health Part A,* 65(12), 853-867), MCL-5B lymphoblastoid cell line (commercially available from Gentest, Woburn Mass.); and (d) non-mammalian cells such as yeast, bacterial, plant, fungal etc. with native expression of P450(s) or the same having been transformed with an expressible P450 cDNA(s) and P450 reductase.

For cell-based compound screening, any suitable amount of test compound may be used, depending on the potency of the test compound and toxicity. For primary library screening, the concentration of test compounds used typically ranges from about 1 to about 1000 micromolar, usually about 10-100 micromolar. Any suitable incubation time may be used. Generally, the time period for incubation of a test compound with cells typically ranges from about 1 minute to about 96 hours, usually about 24 hours to about 72 hours.

Any suitable number of cells may be used for cell-based compound screening, including cell-based high throughput screening. A single cell would be the low end of a general range while for a cell culture receptacle surface with adherent cells, cell confluence or super confluence would be considered to be the upper end of the general range for adherent cells. For suspension cultures, a cell-saturated suspension would be considered the upper end of a general range. In practicing this invention, the preferred number of cells would be the minimum number of cells where signal is detectable above background to a maximum number of cells described for the general range. For the incubation period, the suitable temperature and pH ranges will depend on the requirements of the cell. Generally, most cells are cultured at pH 7.4 and at 37° C., but most cells are viable, at least temporarily, over a range of temperature of 4 to 42° C. and at pH ranges of about 6 to 9.

The cell-based luminescence detection assay can be performed in a number of different ways. For instance, in one embodiment, luciferase and ATP may be added to the cell medium and luminescence could be detected directly as luciferin leaks out of the cells. In this case the temperature, pH, salt concentration, and other growth requirements will depend on the requirements of the cells. Luciferase is generally active at the physiological salt, pH and temperature conditions typically employed in cell culture.

In another embodiment of the cell-based luminescence detection assay, culture medium may be removed from the culture and added to a luciferase reaction. The conditions for this would be essentially as already described for the second step of a two-step reaction assay described above.

In yet another embodiment of the cell-based assay of the invention, the cells may be lysed in an appropriate lysis buffer that contains ATP, luciferase along with detergent(s) to ensure lysis and then luminescence is read immediately. For animal cells, a buffer with 0.1-1.0% non-ionic detergents such as Triton X 100 or Tergitol is typically sufficient. Bacteria, plant, fungal or yeast cells are usually more difficult to lyse. Detergents, freeze/thaw cycles, hypotonic buffers, sonication, cavitation or combinations of these methods may be used. The method of lysis must produce a lysate that is compatible with luciferase activity. In the case where detergent is used, the detergent is one that is compatible with active luciferase. Luminescence would be proportional to the luciferin or luciferin derivative metabolite(s) generated by the P450 reaction and then released from the cells. In a representative example of cell-based luminescence detection, a volume of lysis buffer is added to an equivolume of the spent cell culture medium. In a variation of this embodiment of the invention, a cell lysate may be prepared with a lysis buffer that does not contain luciferase and ATP, then an aliquot of the lysate could be added to a one-step or two-step luciferase-based assay as described above.

In yet another embodiment of the cell-based luminescence detection assay of the invention, a cell that either transiently or stably expresses a recombinant bioluminescent enzyme, e.g., luciferase, may be used. Any conventional method for creating transient or stable transfected cells may be used. An expressible cDNA vector that has been introduced to the cell encodes the luciferase. Luminescence would then evolve as a P450(s) also present in the cell metabolizes the luciferin derivative supplied in the medium. P450 activity may be determined by measuring luminescence after a predetermined time period either in situ directly or after lysis. Vectors for making the cells by transient or stable transfection are available from Promega (Madison, Wis.), Clontech (Pal Alto, Calif.) and Stratagene (La Jolla, Calif.).

In another embodiment of the invention, a tissue-based method is provided for screening a test compound or library of compounds to determine their effect on cytochrome P450 activity of the cell. The test compound is contacted with tissue, the luminogenic molecule, e.g., luciferin derivative, and bioluminescent enzyme, e.g., luciferase for a predetermined period of time. Thereafter, the P450 activity resulting from the interaction of the tissue with the compound is determined by measuring luminescence of the reaction mixture relative to a control (minus test compound) reaction mixture. Representative examples of tissue include, without limitation, liver, intestine, and lung. The tissue may be used in the form of minces or slices such as liver slices. Generally, the same considerations provided above for cell-based assays would be applicable.

In another embodiment of the invention, a method is provided for screening a test compound to determine its effect on the cytochrome P450 activity of an animal. The test compound and the luminogenic molecule, e.g., luciferin derivative, are administered to the animal. After a predetermined time period, a biological specimen is removed from the animal. Representative biological specimen includes blood and serum, urine, feces, bile, cerebrospinal fluid, lymph, saliva, tears, and mucous (basically any body fluid where CYP450 metabolites might be found). Blood/serum, urine, feces and bile are preferable biological specimens. Blood and feces would likely need to be processed. For instance, blood specimens may be processed to remove cells and produce serum. A fecal specimen may be processed to produce an extract. Most of the other fluids would ideally be added directly to a luciferase assay or may be optionally diluted prior to addition to the luciferase assay. The specimen is then contacted with luciferase, ATP and $Mg^{2+}$. After a predetermined time period, P450 activity resulting from the interaction of the animal with the compound is determined by measuring luminescence relative to a control. One type of control would include a specimen obtained from the animal prior to administration of the test compound. This type of control would involve administration of the luciferin derivative without exposure to the drug and the samples and measurements would be taken at a set time. At a later time, after the luciferin is cleared from its system, the test experiment, luciferin derivative plus drug exposure, would be performed on the same animal in the same way. This control has the advantage of using the same animal as test and control. This principle could also be applied to cell-based and tissue slice assays. An alternative approach would be to have separate test and control animals. The test animals would receive luciferin derivative and drug while the control animals would receive only luciferin derivative In one aspect of the invention, the compound and luciferin derivative are preferably administered to the animal either simultaneously or contemporaneously. After a first predetermined time period, a biological specimen is obtained from the animal. The biological specimen is then contacted with luciferase for a second predetermined time period. The effect of the test compound on cytochrome P450 activity of the animal is determined by measuring the luminescence produced from the reaction mixture relative to a control reaction mixture (e.g. specimen obtained from control animals as described above).

In another aspect of the invention, the compound is preferably administered first to the animal. After a first predetermined time period, the luciferin derivative is then administered to the animal. After a second predetermined time period, a biological specimen is obtained from the animal. The biological specimen is then contacted with luciferase for a predetermined time period. The effect of the test compound on cytochrome P450 activity of the animal is determined by measuring the amount of luminescence that is generated from the luciferase reaction mixture relative to a control (e.g., based on a specimen obtained from control animals as described above).

The test compounds and luminogenic molecules, e.g., luciferin derivatives, may be formulated by any suitable means and can be used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of non-toxic auxiliary substances, such as wetting agents, pH buffering agents, and the like. If desired, absorption enhancing preparations (e.g., liposomes) may be utilized.

The amount of the test composition required as an in vivo dose as well as the amount of luciferin derivative used will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In non-human animal studies, applications of potential drug candidates are commenced at higher dosage levels, with dosage being decreased until the desired effect is no longer achieved or adverse side effects disappear. The dosage can range broadly depending upon the desired affects and the therapeutic indication. Typically, dosages may be between about 10 microgram/kg and 100 mg/kg body weight, preferably between about 100 microgram/kg and 10 mg/kg body weight. Administration is preferably oral. Oral administration would be preferable, although absorption through skin or mucous membranes, intravenous, subcutaneous or intraperitoneal injection routes may be used. While control of dosage may be problematic in some instances, oral administration would allow the analyst to examine first pass metabolism that is greatly influenced by p450s in the cells lining the gut where the compounds are absorbed. Administration by injection may be better for controlling dose in animals.

In yet another aspect of the invention, an animal-based high throughput assay for screening compounds is provided. Laboratory animals are useful for defining mechanisms of drug activity and for testing therapeutic regimens. More recently, zebrafish and other teleosts have been found to be particularly useful for in vivo high throughput screening of compounds that employ intact animals. As defined herein, the term "teleost" means of or belonging to the Telostei or Teleostomi, a group consisting of numerous fishes having bony skeletons and rayed fins. Teleosts include, for example, zebrafish, medaka, Giant rerio, and puffer fish. See, for instance, U.S. Pat. No. 6,299,858 (Phylonix, Inc., assignee), which is incorporated by reference in its entirety. For instance, test compound and luciferin derivative may be administered to living embryonic teleosts contained in multi-well plates. The teleosts are maintained in a suitable medium such as water. After one or more predetermined time periods, the medium is then contacted with luciferase for a second predetermined time period. The effect of the test compound on cytochrome P450 activity of the animal may be determined by measuring the luminescence produced from the mixture relative to a control reaction mixture absent test compound.

In another aspect of the invention, the compound is preferably administered first to the teleosts. After a first predetermined time period, the animal is contacted with the luciferin derivative. After a second predetermined time period, the medium is then contracted with luciferase. The effect of the test compound on cytochrome P450 activity of the animal may be determined by measuring the luminescence produced from the mixture relative to a control reaction mixture absent test compound.

Transgeneic animals with a luciferase transgene are also useful in animal-based assays for ascertaining P450 activity and for screening one or more compounds. Luciferase transgenes have been efficiently expressed in livers, mostly in mouse. Xenogen, Inc. and others has developed transgeneic animals such as mouse and rat with a luciferase transgene that gets expressed in target tissues such as liver. See, for instance, U.S. Pat. Nos. 5,650,135 and 6,217,847, which are incorporated by reference in their entirety. Generally, such transgeneic animals are injected with luciferin and imaging technology (in vivo biophotonic imaging) is then used to measure luminescence at the site of luciferase expression in the living, intact animal. Thus, in another aspect of the invention, a transgenic animal having a bioluminescence enzyme, e.g., luciferase, transgene may be administered a luminogenic substrate that will be converted to into a substrate for a bioluminescence enzyme in tissues where the appropriate P450 is expressed. If the bioluminescence enzyme, e.g., luciferase, transgene is also expressed in that tissue, light will be produced and such light may be detected by any suitable means. As discussed above, one or more drugs can be tested for P450 effects in such transgeneic animals in a animal-based assay. Alternatively, tissue from such transgeneic animals can be used in a tissue-based assay. A drug that inhibits P450 enzyme activity will diminish the signal and a drug that induces P450 gene expression will enhance the signal.

The invention further provides a method and kit for relieving inhibition of firefly lucifererase by its inhibitor inorganic pyrophosphate (iPP). The presence of iPP in a luciferase-based reaction is undesirable because it may affect the reproducibility of the reaction. Pyrophosphate is a product of a luciferase-based reaction with ATP, O2 and luciferin. Under certain conditions, iPP may accumulate to inhibitory levels. In addition, components of a luciferase-based reaction may contribute inhibitory amounts of iPP. For example, orthophosphate salts used to buffer the reaction may contain iPP as a contaminant. While avoiding the use of phosphate buffered solutions can solve the iPP problem, this is often inconvenient or impractical, particularly in P450 reactions where phosphate buffers are generally used. It has been discovered that the inclusion of a pyrophosphatase such as an inorganic pyrophosphatase enzyme (iPPase) in the luciferase-based reaction reduces or prevents luciferase inhibition by iPP that may already be present in the assay mixture or that may be generated during the course of the luciferase reaction. While this discovery is generally applicable to all luciferase-based reactions where potential inhibition of luciferase by iPP may be a problem, the inclusion of a pyrophosphatase such as iPPase in luminescent cytochrome P450 (P450) assays has been found to be particularly useful. Without being bound by any theory of operation, it is believed that the pyrophosphatase, e.g., iPPase, acts to prevent the build-up of iPP as well as remove it from a solution by hydrolyzing the iPP into orthophosphate.

In practicing this invention, the pyrophosphatase, e.g., iPPase, may be added prior to, simultaneously with, or shortly after luciferase addition. Preferably, the pyrophosphatase, e.g., iPPase, is added to the assay mixture simultaneously with luciferase addition to degrade any iPP already present in the mixture and generated during the luciferase reaction. The amount of pyrophosphatase, e.g., iPPase, used in the reaction is sufficient to remove or eliminate any iPP that may already be present or may be subsequently generated during the course of the luciferase reaction. Generally, in the presence of a pyrophosphatase, e.g., iPPase, the level of iPP in the reaction mixture is eliminated or reduced to an amount which has little or no significant effect on luciferase activity during a luciferase reaction. That is, the level of iPP is low enough to reduce luciferase inhibition to an insignificant level. The iPPase may be derived from a variety of sources including without limitation, yeast, prokaryotes and mammals. In practicing this invention, iPPase derived from *Saccharomyces cerevisiae* is preferred.

In one embodiment of this invention, the pyrophosphatase, e.g., iPPase, may be included in a cell-free or celled-based luminescent P450 assay. P450 enzymes convert luciferin derivatives that are pro-substrates for firefly luciferase into luciferin substrates that then react with luciferase to generate light. For instance, in the first step of the two-step method described above, a P450 enzyme may be incubated with a luciferin derivative under suitable assay reaction conditions. In a second step, the luciferin substrate generated in the first step is then detected luminogenically when luciferase and ATP are added to the mixture of the first step. Generally, it is convenient to employ $KPO_4$ buffers in the first step to buffer pH and to provide optimal salt concentration for specific P450 isoforms by varying its concentration. However, some $KPO_4$ buffers carry sufficient amounts of iPP contaminant which may inhibit luciferase and thus impair luciferin detection. By adding an iPPase to the reaction mixture, inhibition by the presence of any iPP contaminant may be reduced or prevented.

In another embodiment of this invention, the pyrophosphatase, e.g., iPPase, may be included in any luciferase reaction, including cell-free or cell-based luciferase assays. The addition of pyrophosphatase, e.g., iPPase, as a reaction component would allow these assays to be performed in conventional phosphate buffers without concern for iPP inhibition of luciferase. Other applications may include the use of iPPase in luciferase assays where the iPP generated by the luciferase reaction accumulates to inhibitory levels.

In another embodiment of the invention, a kit is provided for determining the activity of a CYP450 or the effect of a substance, e.g., a drug candidate, on cytochrome P450 enzyme activity. Such kits comprise, in one or more containers, usually conveniently packaged to facilitate use in assays, quantities of various compositions essential for carrying out the assays and methods in accordance with the invention. Thus, the kit may include one or more types of cytochrome P450 enzymes; one or more luminogenic molecules, e.g., D-luciferin derivatives, that are substrates for one or more types of cytochrome P450 enzymes and a pro-substrate of a bioluminescent enzyme, e.g., luciferase enzyme; a bioluminescent enzyme, e.g., luciferase enzyme; and directions for using the kit. Optionally, the kit includes ATP, a source of Mg ions, non-ionic detergent, a pyrophosphatase, e.g., iPPase, and/or buffers or any other reaction components to provide a solution at suitable pH and ionic strength. As indicated, the various components can be combined, e.g., in solution or a lyophilized mixture, in a single container or in various combinations (including individually) in a plurality of containers The preferred kit includes vial(s) with P450 substrate (e.g., D-luciferin derivative), vial(s) containing a mixture of bioluminescent enzyme, e.g., luciferase, and optional iPPase (preferably from *Saccharomyces cervisiae*) (preferably a lyophilized preparation) and a vial with a dilution buffer that contains ATP for the bioluminescent enzyme, e.g., luciferase (in the case of a lyophilized luciferase/ATP preparation, this buffer is a "reconstitution buffer"). The dilution buffer or reconstitution buffer would also contain the detergent.

The kits can also include, as well known to the ordinary skilled in the art, various controls and standards, including no P450 (negative control), to ensure the reliability and accuracy of the assays carried out using the kits.

EXAMPLES

Materials

Sf9 cell expressed CYP450 preparations (Supersomes™), pooled human liver microsomes and NADPH generating system (NADP+, glucose-6-phosphate and glucose-6-phosphate dehydrogenase) were purchased from GenTest (Woburn, Mass.). The substrates, luciferin 6' methyl (Luc ME), ethyl (Luc EE), chloroethyl (Luc CEE) and benzyl (Luc BE) ethers and dehydroxyluciferin (H-Luc) were manufactured by Promega Biosciences (San Luis Obispo, Calif.). Luc ME and Luc EE were also purchased from Sigma-Aldrich (St. Louis). The recombinant, mutant of firefly luciferase from *Photuris pennsylvanica* was from Promega (17). All chemical reagents and solvents referred to herein are readily available from a number of commercial sources including Aldrich Chemical Co. or Fischer Scientific. NMR spectra were run on a Hitachi 60 MHz R-1200 NMR spectrometer or a Varian VX-300 NMR spectrometer. JR spectra were obtained using a Midac M series FT-IR instrument. Mass spectral data were obtained using a Finnegan MAT 90 mass spectrometer. All melting points are corrected.

Example 1

Synthesis of Luciferin Derivatives (a) Preparation of 2-cyanobenzothiazole Derivatives
Luciferol:
A suspension of D-luciferin free acid (0.43 g, 1.53 mmol) in THF (15 mL) was cooled in a −20° C. bath (dry ice-isopropanol). To the suspension was added dropwise via syringe a solution of borane-THF (1.8 mL of a 1 M solution in THF, 1.8 mmol). The pale yellow solution was allowed to warm to ambient temperature overnight (about 15 h) under nitrogen. Additional borane-THF (2.5 mL of a 1 M solution in THF, 2.5 mmol) was added and the reaction went an additional 24 h. The excess borane-THF was quenched by the addition of 10% aqueous acetic acid solution and the resulting bilayer was extracted with ethyl acetate (3×75 mL). Combined extracts were dried and evaporated to give an orange solid that was purified by chromatography on silica gel (70 g) using 4:1 dichloromethane-methanol. This operation separated the remaining D-luciferin free acid from a less polar product mixture. The less polar product mixture was separated by reverse-phase HPLC on a 1-inch Synergi 4μ MAX-RP 80A column (100×21.20 mm) using a methanol-water gradient. Appropriate fractions were pooled and evaporated to provide 10 mg (3% yield) of the desired product as a pale yellow solid. This product was 95.4% pure by HPLC analysis. MS (ESI−): m/z 264.4 (M−H)−; calc'd: 265.01.

2-Cyanobenzothiazole

A suspension of potassium cyanide (1.50 g, 23.0 mmol) in dimethylsulfoxide (DMSO, 100 mL) was prepared in a 1-L 3-necked flask fitted with a reflux condenser, a heating mantle and an internal temperature probe. The 2-chlorobenzothiazole (2.6 g, 2.0 mL, 15.3 mmol) was added to the reaction flask via pipet and the reaction was heated at 80° C. (internal temperature). The reaction was monitored periodically by TLC (9:1 heptane-ethyl acetate). After 5 hours the reaction appeared to be about 50% complete. After 17 hours the reaction was judged complete by TLC analysis. The reaction mixture was allowed to cool to room temperature and was then extracted with ether (5×100 mL). The extracts were dried over sodium sulfate and concentrated to give a yellow-orange solid. The crude solid was purified on silica gel (100 g) using 9:1 heptane-ethyl acetate. Fractions containing product were pooled and concentrated to give 1.4 g (57%) of the desired product as a yellow-orange solid. The structure was confirmed by $^1$H NMR analysis in DMSO-d6.

6-(2-Chloroethoxy)-2-cyanobenzothiazole

A suspension of 2-cyano-6-hydroxybenzothiazole (1.0 g, 5.68 mmol) in acetone (5 mL) was prepared in a 50-mL 2-necked round-bottomed flask fitted with a reflux condenser. Anhydrous potassium carbonate (1.57 g, 11.3 mmol) was added to the reaction mixture and the suspension turned to a yellow solution. Then 1-bromo-2-chloroethane (1.06 g, 0.56 mL, 7.38 mmol) was added by syringe and the reaction mixture was heated at reflux using a heated stir plate and oil bath. The reaction was monitored periodically by RP HPLC. After 5 hours the reaction appeared to be about 30% complete. Additional 1-bromo-2-chloroethane was added (2.84 mmol, 0.21 mL) and the reaction was refluxed overnight. HPLC analysis indicated the reaction was about 50% complete. Additional 1-bromo-2-chloroethane (2.84 mmol, 0.21 mL) and potassium carbonate (0.60 g, 4.37 mmol) were added and the reaction was refluxed for the rest of the day (about 7 h). The reaction was about 64% complete, and it was refluxed overnight. The next morning the reaction was found to be about 84% complete. Additional 1-bromo-2-chloroethane (2.84 mmol, 0.21 mL) and potassium carbonate (0.60 g, 4.37 mmol) were added and the reaction was refluxed for the rest of the day (about 7 h). At this point the reaction was about 92% complete. The reaction mixture was allowed to cool to room temperature and it was then filtered through glass fiber paper and rinsed with acetone. The filtrate was concentrated to give a yellow-brown solid. The crude solid (1.3 g) was purified on silica gel (100 g) using 4:1 heptane-ethyl acetate. Fractions containing product were pooled and concentrated to give 1.0 g (74%) of the desired product as an off-white solid. The structure was confirmed by $^1$H NMR analysis in DMSO-d6.

6-(4-Trifluoromethylbenzyloxy)-2-cyanobenzothiazole

A suspension of 2-cyano-6-hydroxybenzothiazole (1.0 g, 5.68 mmol) in acetone (5 mL) was prepared in a 100-mL 2-necked round-bottomed flask fitted with a reflux condenser. Anhydrous potassium carbonate (0.94 g, 6.82 mmol) was added to the reaction mixture and the suspension turned to a yellow solution. Then 4-(trifluoromethyl)benzyl bromide (1.49 g, 6.25 mmol) was added and the reaction mixture was heated at reflux for 15 h using a heated stir plate and oil bath. The reaction mixture was allowed to cool to ambient temperature and then filtered to remove inorganic salts. The filtrate was concentrated by rotoevaporation to provide 1.7 g (89% yield) of an off-white solid that was used without purification. The structure was confirmed by $^1$H NMR analysis in DMSO-d6.

6-(Benzyloxy)-2-cyanobenzothiazole

A suspension of 2-cyano-6-hydroxybenzothiazole (0.35 g, 2.00 mmol) in acetone (35 mL) was prepared in a 100-mL 2-necked round-bottomed flask fitted with a reflux condenser. Anhydrous potassium carbonate (0.33 g, 2.40 mmol) was added to the reaction mixture and the suspension turned to a yellow solution. Then benzyl bromide (0.41 g, 0.29 mL, 2.40 mmol) was added and the reaction mixture was heated at reflux for 15 h using a heated stir plate and oil bath. The reaction mixture was allowed to cool to ambient temperature and then filtered to remove inorganic salts. The filtrate was concentrated by rotoevaporation to provide 0.51 g of a pale yellow solid. The crude product was purified by flash chromatography on silica gel (24 g) using a mobile phase consisting of a mixture of 4:1 heptane-ethyl acetate to provide 410 mg (77% yield) of the desired product as a white foam. The structure was confirmed by $^1$H NMR analysis in DMSO-d6.

6-(2-Phenylethoxy)-2-cyanobenzothiazole

A suspension of 2-cyano-6-hydroxybenzothiazole (1.00 g, 5.68 mmol) in acetone (5 mL) was prepared in a 100-mL 2-necked round-bottomed flask fitted with a reflux condenser. Anhydrous potassium carbonate (1.18 g, 8.52 mmol) was added to the reaction mixture and the suspension turned to a yellow solution. Then (2-bromoethyl)benzene (1.37 g, 0.88 mL, 7.38 mmol) was added and the reaction mixture was heated at reflux for using a heated stir plate and oil bath. Progress of the reaction was monitored by HPLC analysis of reaction aliquots. After 15 h of reflux the reaction was about 40% complete. Additional (2-bromoethyl)benzene (0.5 equivalents, 2.84 mmol) and potassium carbonate (0.5 equivalents, 2.84 mmol) were added periodically during the course of two days until the starting material was consumed. The reaction mixture was allowed to cool to ambient temperature and then filtered to remove inorganic salts. The filtrate was concentrated by rotoevaporation to provide 2.2 g of a crude oil. The crude product was purified by flash chromatography on silica gel using an initial mobile phase consisting of a mixture of 9:1 heptane-ethyl acetate. The mobile phase was adjusted to a mixture of 5:1 heptane-ethyl acetate, and then adjusted to a mixture of 7:3 heptane-ethyl acetate to provide 800 mg (50% yield) of the desired product as an off-white foam. The structure was confirmed by $^1$H NMR analysis in DMSO-d6.

6-(Geranyloxy)-2-cyanobenzothiazole

To a dry 25-ml round-bottomed flask containing acetone (5 mL), anhydrous potassium carbonate (1.2 g, 8.4 mmole), and geranyl bromide (1.5 mL, 7.3 mmole) was added 6-hydroxy-2-cyanobenzothiazole (1 g, 5.6 mmole). The mixture was refluxed under argon with stirring. Reaction progress was monitored by TLC analysis, developing with 2:1 heptane-ethyl acetate. After 20 h, the potassium carbonate was filtered from the cooled reaction mixture. The solution was concentrated in vacuo to yield 2.1 g of solid. The solid was further purified by flash chromatography using a mixture of 9:1 heptane-ethyl acetate. Appropriate fractions were pooled and evaporated to yield 0.84 g of solid. The structure was confirmed by $^1$H NMR analysis in DMSO-d6.

6-(Prenyloxy)-2-cyanobenzothiazole

To a dry 25-ml round-bottomed flask containing acetone (5 mL), anhydrous potassium carbonate (1.2 g, 8.4 mmol), and prenyl bromide (839 microliters, 7.3 mmole) was added 6-hydroxy-2-cyanobenzothiazole (1.0 g, 5.6 mmol). The mixture was refluxed under argon with stirring. Reaction progress was monitored by TLC analysis, developing with 2:1 heptane-ethyl acetate. After 28 h, the potassium carbonate was filtered from the cooled reaction mixture. The solution was concentrated in vacuo to yield 1.7 g of solid. The solid was further purified by flash chromatography using 9:1 heptane-ethyl acetate and gradually stepping to 4:1 heptane-ethyl acetate. Appropriate fractions were pooled and evaporated to yield 0.8 g of solid. The structure was confirmed by $^1$H NMR analysis in DMSO-d6.

6-(2-Picolinyloxy)-2-cyanobenzothiazole (Bromomethyl)pyridine hydrobromide (1.87 g, 7.38 mmol) and 2-cyano-6-hydroxybenzothiazole (1.00 g, 5.68 mmol) were suspended in acetone (50 mL). After introduction of potassium carbonate (1.96 g, 14.2 mmol), the suspension was refluxed for 72 h under nitrogen. After cooling down the mixture and filtering the solids, the filtrate was concentrated and the residue was purified by silica gel chromatography using 50%-75% ethyl acetate in heptane. A yellowish solid was obtained in 72% yield. MS (ESI+): m/z 267.90 (M+H)$^+$; calc'd: 268.05.

6-(3-Picolinyloxy)-2-cyanobenzothiazole

To a solution of 2-cyano-6-hydroxybenzothiazole (0.39 g, 2.2 mmol) in acetone (50 mL) was added 3-(bromomethyl) pyridine hydrobromide (0.7 g, 2.76 mmol), cesium carbonate (2.15 g, 6.6 mmol), and a catalytic amount of sodium iodide. After adding 3A molecular sieves, the yellow suspension was refluxed for 40 h under nitrogen. After cooling down the mixture and filtering the solids, the filtrate was concentrated and the residue was purified by silica gel chromatography using 50%-100% ethyl acetate in heptane. A yellowish solid was obtained in 61% yield. MS (ESI+): m/z 267.64 (M+H)$^+$; calc'd: 268.05.

6-(4-Picolinyloxy)-2-cyanobenzothiazole

To a solution of 2-cyano-6-hydroxybenzothiazole (1.18 g, 6.71 mmol) in acetone (50 mL) was added 3 Å molecular sieves and cesium carbonate (3.98 g, 12.2 mmol). The resulting suspension was stirred at room temperature for two hours. Then another equivalent of cesium carbonate (1.99 g, 6.1 mmol) was introduced, followed by addition of 4-(bromomethyl)pyridine hydrobromide (1.0 g, 6.1 mmol) and a catalytic amount of cesium iodide. The resulting yellow suspension was refluxed for 48 h under nitrogen. After cooling down the mixture and filtering the solids, the filtrate was concentrated and the residue was purified by silica gel chromatography, using 30% ethyl acetate in heptane to remove the starting material and then 25% methanol in ethyl acetate. A yellowish solid was obtained in 70% yield. MS (ESI+): m/z 267.74 (M+H)$^+$; calc'd: 268.05.

(b) General Procedures for the Conversion of 2-cyanobenzothiazole Derivatives to D-luciferin Derivatives.

A solution of 0.39 M aqueous cysteine hydrochloride monohydrate (1.3 equivalents, based on the quantity of the 2-cyanobenzothiazole derivative) was added dropwise to an equal volume of a 0.39 M solution of potassium carbonate, maintaining the pH at 6-7 by addition of 6 M HCl. In a separate reaction flask the 2-cyanobenzothiazole derivative was dissolved in sufficient methanol to prepare a 0.1 M solution. This solution was purged with nitrogen to remove oxygen. The cysteine/potassium carbonate solution described above was added dropwise to the reaction flask containing the 2-cyanobenzothiazole derivative, maintaining the pH at 6-7 by addition of 6 M HCl. The reaction was monitored by TLC, and when complete the reaction mixture was concentrated by rotoevaporation using a cold water bath (<30° C.).

6'-Deoxyluciferin (H-Luc)

Prepared from 2-cyanobenzothiazole (100 mg, 0.62 mmol) according to the general procedure. The crude solid product was purified by flash chromatography on silica gel (20 g) using 9:1 dichloromethane-methanol to afford 163 mg (99%) of desired product as a pale yellow solid. This material was 96% pure by HPLC analysis. MS (ESI−): m/z 263.40 (M−H)⁻; calc'd: 262.99.

Luciferin 6'-(2-chloroethyl)ether (Luc CEE)

Prepared from 6-(2-chloroethoxy)-2-cyanobenzothiazole (1.0 g, 4.19 mmol) according to the general procedure. The solid product thus obtained was 99.5% pure by HPLC analysis and further purification was not deemed necessary. The yield of this product was 1.36 g (95% yield). MS (ESI+): m/z 342.94 (M+H)⁺; calc'd: 343.00.

Luciferin 6'-benzyl ether (Luc BE)

Prepared from 6-(benzyloxy)-2-cyanobenzothiazole (0.41 g, 1.5 mmol) according to the general procedure. The crude solid product was purified by flash chromatography on silica gel (90 g) using 100% dichloromethane initially, gradually stepping up to 8:2 dichloromethane-methanol to afford 190 mg (34% yield) of desired product. MS (ESI−): m/z 368.67 (M−H)⁻; calc'd: 369.04.

Luciferin 6'-(4-trifluoromethyl)benzyl ether (Luc TFMBE)

Prepared from 6-(4-trifluoromethylbenzyloxy)-2-cyanobenzothiazole (1.7 g, 5.08 mmol) according to the general procedure. The resulting solid was purified by flash chromatography on silica gel using initially a mixture of 99:1 dichloromethane-methanol, gradually stepping up to 9:1 dichloromethane-methanol. Appropriate fractions were pooled and evaporated to yield 700 mg (31%) of the desired product as a solid.

Luciferin 6'-(2-phenylethyl)ether (Luc PEE)

Prepared from 6-(2-chloroethoxy)-2-cyanobenzothiazole (0.80 g, 2.85 mmol) according to the general procedure. The resulting solid was purified by flash chromatography on silica gel using initially a mixture of 6:3:1 heptane-ethyl acetate-methanol, then a mixture of 5:3:2 methanol-heptane-ethyl acetate. Appropriate fractions were pooled and evaporated to yield 145 mg (14%) of the desired product as a solid. MS (ESI+): m/z 384.52 (M+H)⁺; calc'd 385.07.

Luciferin 6'-geranyl ether (Luc GE)

Prepared from 6-geranyloxy-2-cyanobenzothiazole (0.8 g) according to the general procedure. The resulting solid was purified by flash chromatography on silica gel using 9:1 dichloromethane-methanol. Appropriate fractions were pooled and evaporated to yield 101 mg of solid. The structure was confirmed by ¹H NMR analysis in DMSO-d6.

Luciferin 6'-prenyl ether (Luc PE)

Prepared from 6-prenyloxy-2-cyanobenzothiazole (0.8 g) according to the general procedure. The resulting solid was first purified by flash chromatography using 9:1 dichloromethane-methanol gradually stepping to 8:2 dichloromethane:methanol. The solid was then repurified by flash chromatography using 2:1 heptane-ethyl acetate. Appropriate fractions were pooled and evaporated to yield 339 mg of yellowish solid. The structure was confirmed by ¹H NMR analysis in DMSO-d6. Fluorescence HPLC analysis indicated background luciferin, so the solid was further purified by preparative reverse-phase HPLC.

Luciferin 6'-(2-picolynyl)ether (Luc 2PE)

Prepared from 6-(2-picolinyloxy)-2-cyanobenzothiazole (250 mg, 0.94 mmol) according to the general procedure. The solid product thus obtained was 92.0% pure by HPLC analysis and the yield of this product was 80%. MS (ESI+): m/z 371.55 (M+H)⁺; calc'd 372.04.

Luciferin 6'-(3-picolynyl)ether (Luc 3PE)

Prepared from 6-(3-picolinyloxy)-2-cyanobenzothiazole (250 mg, 0.94 mmol) according to the general procedure. The solid product thus obtained was 99.8% pure by HPLC analysis and further purification was not deemed necessary. The yield of this product was 60%. MS (ESI+): m/z 371.64 (M+H)⁺; calc'd 372.04.

Luciferin 6'-(4-picolynyl)ether (Luc 4PE)

Prepared from 6-(4-picolinyloxy)-2-cyanobenzothiazole (267 mg, 1.0 mmol) according to the general procedure except that 5 mL DMF was used to dissolve the starting material. The solid product thus obtained was 96.0% pure by HPLC analysis and further purification was not deemed necessary. The yield of this product was 20%. MS (ESI+): m/z 371.61 (M+H)⁺; calc'd 372.04.

Example 2

Two step CYP450/Luciferase Reaction and Luciferin Derivatives Evaluation

In this Example, a procedure for a two-step CYP450/luciferase assay is provided. Luciferin derivatives were evaluated as P450 substrates and luciferase pro-substrates using this procedure. 20 microliter CYP450 reactions were prepared at pH 7.4 in an amount of KPO₄ buffer that is optimal for a given CYP450 isoform (100 mM for CYP1A1, CYP1A2, CYP2B6, CYP2D6 and CYP2E1; 50 mM for CYP2C8 and CYP2C19; 25 mM for 2C9 and for pooled human liver microsomes; 200 mM for CYP3A4). For CYP2A6 100 mM Tris at pH 7.5 was substituted for $KPO_4$. Reaction mixes also contained 1.3 mM NADP+, 3.3 mM glucose-6-phosphate, 0.4 U/ml glucose-6-phosphate dehydrogenase, 3.3 mM $MgCl_2$ and a luciferin derivative/CYP450 substrate. Reactions were initiated by addition of 0.4 pmoles recombinant human CYP450 co-expressed with CYP450 reductase in Sf9 cell microsomal membranes or 4 microgram pooled human liver microsomes and incubation at 37° C. After an initial incubation period at 37° C. 20 microliter CYP450 reactions were mixed with an 80 microliter luciferase reaction mix. The luciferase reaction mix contained 250 micromolar ATP, 5-25 microgram/mL thermostable luciferase from *Photuris pennsylvanica* prepared as described in WO/9914336, published Mar. 25, 1999 which is incorporated by reference in its entirety), 20 mM Tricine pH 7.8, 0.1 mM EDTA, 8 mM $MgCl_2$, 0.6 mM coenzyme A and 33 mM DTT. Assays were also performed using 50 microliter CYP450 and luciferase reaction volumes (e.g., FIG. 3, panel B, table 3). Light output was measured immediately in a Turner Reporter, Turner 20/20 or Berthold Orion luminometer. Because the calibration of instruments from different manufacturers varies the quantitation of light output is instrument-specific and direct comparisons between instruments cannot be made.

O-dealkylation and hydroxylation are common CYP450 catalyzed xenobiotic transformations (9). A panel of recombinant human CYP450 microsome preparations was tested for O-dealkylase activity against luciferin 6' methyl (Luc ME), ethyl (Luc EE), chloroethyl (Luc CEE), benzyl (Luc BE), p-CF3 benzyl (Luc TFMBE), phenylethyl (Lluc PEE), geranyl (Luc GE), 2, 3 and 4 picolinyl (Luc 2PE, Luc 3PE and Luc 4PE) and prenyl (Luc PE) ethers and for hydroxylase activity against dehydroluciferin (H-Luc) (FIG. 2). These compounds are either inactive in a light generating luciferase reaction or only modestly active as compared to authentic luciferin. The CYP450 activities tested are contained in microsome fractions from insect cells that over-express a single recombinant human CYP450 isoform in combination with NADPH CYP450 reductase. It was reasoned that if CYP450s dealkylated or hydroxylated the luciferin derivatives at the 6' position, authentic luciferin would be generated that could be detected enzymatically in a light generating firefly luciferase reaction as described by the equation in FIG. 1.

Luc ME, Luc EE, Luc CEE, Luc BE, H-Luc, Luc TFMBE, Luc PEE, Luc GE, Luc 2PE, Luc 3PE and Luc 4PE and Luc PE were subjected to a two-step assay where they were first incubated with a panel of CYP450 enriched microsomes or control microsomes (with no detectable CYP450 activity) under conditions where the CYP450s are known to be active. The panel included CYP1A1, CYP1A2, CYP2A6, CYP2B6, CYP2C8, CYP2C9, CYP2C19, CYP2D6, CYP2E1 and CYP3A4. After an initial incubation with CYP450, luciferase and its requisite cofactors were added and light output was monitored (FIGS. 3 and 9). Light output was increased significantly over controls by CYP1A2, CYP2C8 and CYP2C9 with Luc ME, CYP2C8, CYP2C9 and CYP3A4 with Luc BE, CYP1A1, CYP1A2, CYP2C8 and CYP2C9 with Luc EE, by CYP1A1, CYP1A2, CYP2C8 and CYP2C9 with Luc CEE, by CYP1A1, CYP2C8 and CYP2C9 by Luc TFMBE, by CYP3A4 with Luc PE, Luc PEE, by CYP1A1 with Luc GE and by CYP3A4 with Luc PE (FIG. 3). With Luc 2PE, Luc 3PE and Luc 4PE the most obvious increase in light output was with CYP1A1 and CYP3A4, the effect being most pronounced for both isoforms with Luc 3PE (FIG. 9). These isoforms apparently dealkylated luciferin 6' alkyl ethers and 6' substituted alkyl ethers to form luciferin while the other isoforms tested did not. When H-Luc was used as substrate CYP1A2 and CYP2C9 increased light output over controls. H-Luc was apparently hydroxylated to form luciferin and within the panel tested the reaction was most significant with the CYP2C9 isoform. Values for isoform/substrate combinations not shown were similar to Sf9 cell membrane controls. For each of the panel screens, background luminescence reflects at least in part the presence of contaminating D-luciferin in the unreacted preparations of d-luciferin derivatives. Luminescent CYP1A1, CYP1A2, CYP2C8, CYP2C9 and CYP3A4 reactions were dose-dependent with respect to substrate (data not shown).

Example 3

Figure 4A:
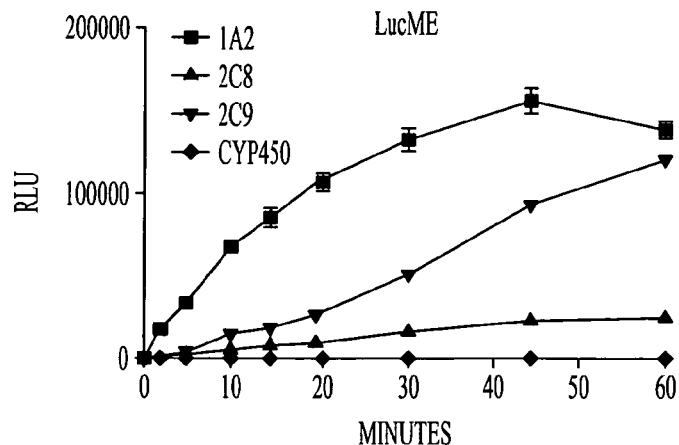
FIG. 4. Time-dependence of CYP450/substrate incubation in two-step luminescent CYP450 reactions. D-luciferin derivatives were incubated in a CYP450 reaction mix for the indicated times at 37° C. before combining with a luciferase reaction mixture. For —CYP450 controls CYP450 Sf9 cell microsomes were replaced with H₂O. Luminescence was read within 12 minutes of combining the reactions on a Turner Reporter (panels A and C) or Berthold Orion (panel B) luminometer.
Figure 4B:
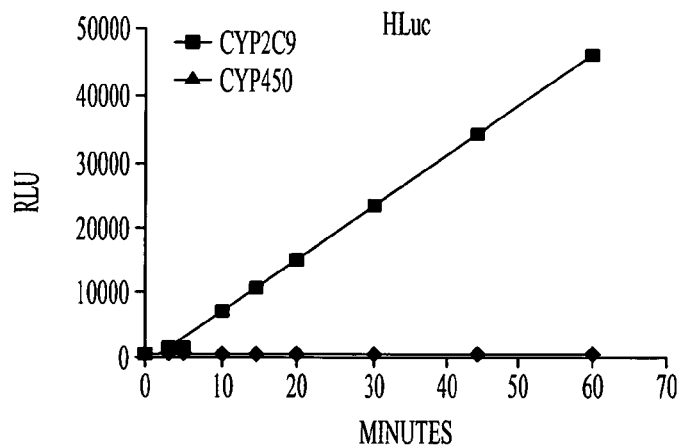
Figure 4C:
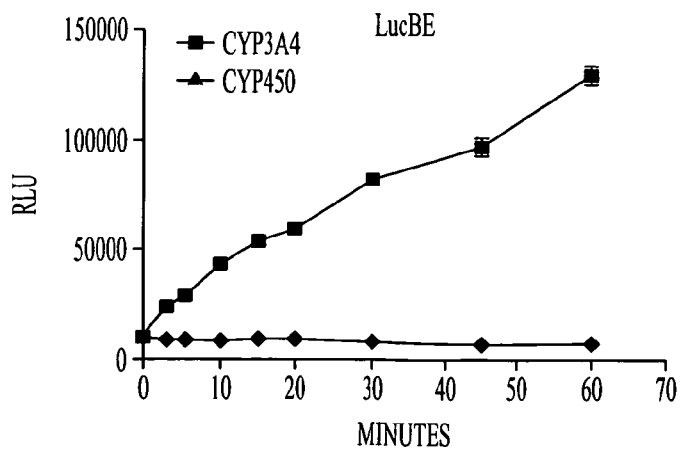

Time-Dependence of CYP450/Substrate Incubation in Two-Step Luminescent CYP450 Reactions Time courses were performed for incubation of CYP1A2, CYP2C8 and CYP2C9 with Luc ME, CYP2C9 with H-Luc and CYP3A4 with Luc BE (FIG. 4). Light output measured within 12 minutes of adding a luciferase reaction mix to the CYP450 reaction mix increased in a linear fashion for up to 60 minutes with CYP2C9 and Luc ME or H-Luc and for CYP3A4 with Luc BE. With CYP1A2 and CYP2C8 there was a time dependent increase but the rate of increase declined and was increasing only modestly by 60 minutes for CYP2C8, and not at all for CYP1A2. These time courses mirror the activity of CYP1A2, CYP2C8, CYP2C9 and CYP3A4 with the conventional substrates phenacetin, paclitaxel, diclofenac and testosterone, respectively (10, 11, 12).

Example 4

Time Course of Light Input from Two-Step Luminescent CYP450 Reactions

Figure 5:
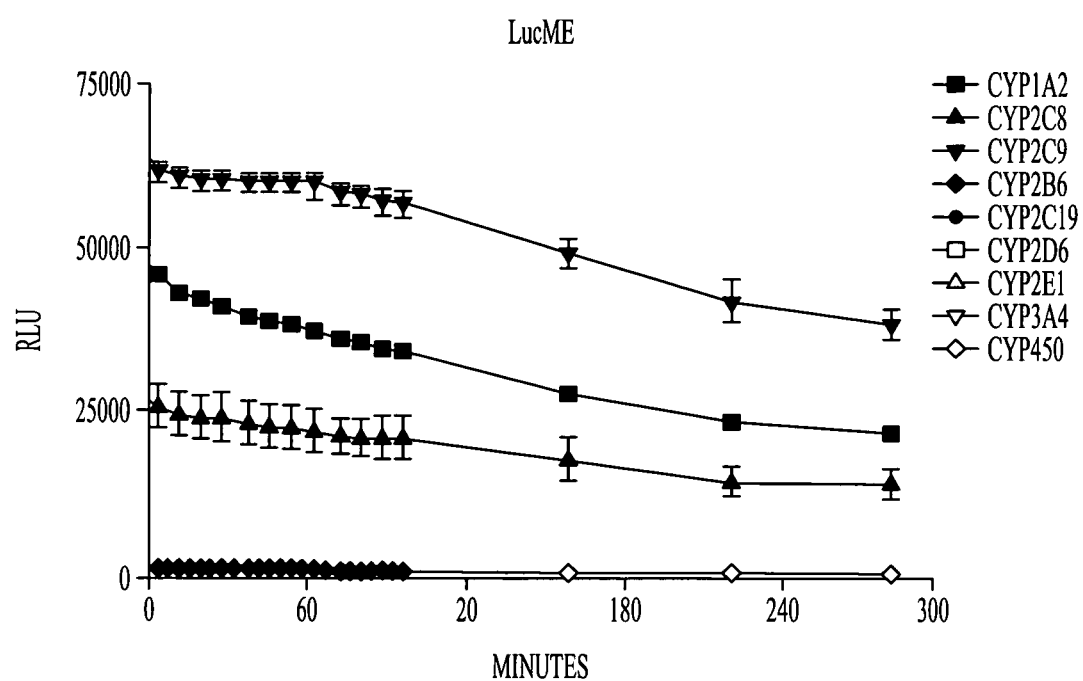
FIG. 5. Time course of light output from two-step luminescent CYP450 reactions. Luc ME was incubated in CYP450 reaction mixes for 60 minutes at 37° C. before combining with a luciferase reaction mixture. In CYP450 controls CYP450 Sf9 cell microsomes were replaced with H₂O. Luminescence was read on a Turner Reporter luminometer beginning 3 minutes after combining the reactions and at successive intervals as indicated for 284 minutes.

In this Example, a luminescent signal was generated after combining luciferase reaction components with a CYP450 reaction and was monitored over time (FIG. 5). D-luciferin derivatives were incubated in a CYP450 reaction mix for 60 minutes at 37° C. before combining with a luciferase reaction mixture. In —CYP450 controls CYP450 Sf9 cell microsomes were replaced with $H_2O$. Luminescence was read on a Turner Reporter luminometer beginning 3 minutes after combining the reactions and at successive intervals as indicated for 284 minutes. For the CYP450s and substrates tested, the signals were quite stable, decaying with a half-life of greater than 5 hours.

Example 5

One Step CYP450/Luciferase Reaction at Room Temperature

In this Example, a procedure for a one-step CYP450/luciferase assay is provided. Luciferin derivatives were evaluated as P450 substrates and luciferase pro-substrates using this procedure. 100 microliter CYP450 reactions were prepared at pH 7.4 in an amount of $KPO_4$ buffer that is optimal for a given CYP450 isoform (see two step reaction method). Reaction mixes also contained 1.3 mM NADP+, 3.3 mM glucose-6-phosphate, 0.4 U/ml glucose-6-phosphate dehydrogenase, 3.7 mM $MgSO_4$, 0.6 mM coenzyme A, a luciferin derivative/CYP450 substrate, 250 micromolar ATP and 21 microgram/mL thermostable luciferase from *Photuris pennsylvanica* prepared as described in WO/9914336, published Mar. 25, 1999 which is incorporated by reference in its entirety). Reactions were initiated by addition of 2.0 pmoles recombinant human CYP450 co-expressed with CYP450 reductase in Sf9 cell microsomal membranes (e.g. GenTest Supersomes™) and incubation at room temperature or 37° C. Light output was measured immediately and continuously in a Turner Reporter or Berthold Orion luminometer.

Figure 6A:
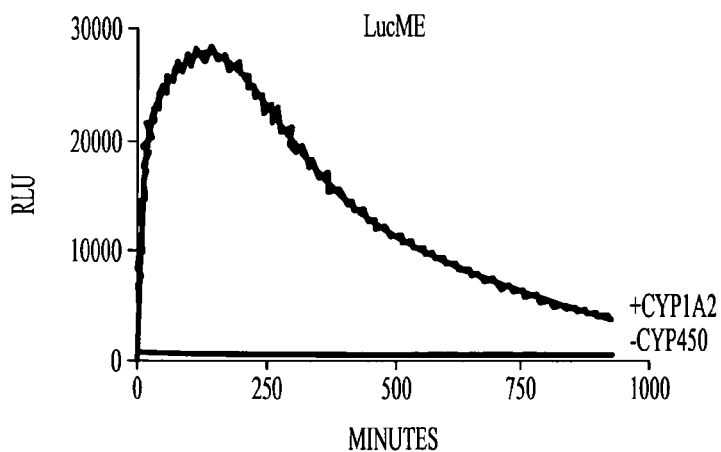
FIG. 6. One-step luminescent CYP450 assays at room temperature. Luc ME was incubated in combined CYP450 and luciferase reaction mixes at room temperature (~22° C.). For —CYP450 controls CYP450 Sf9 cell microsomes were replaced with H₂O. CYP450 and a luciferase reaction mix were added simultaneously to a CYP450 reaction mix and light output was read immediately (time=0). Readings were then taken every 4.25 minutes for 15.5 hours on a Turner Reporter luminometer.
Figure 6B:
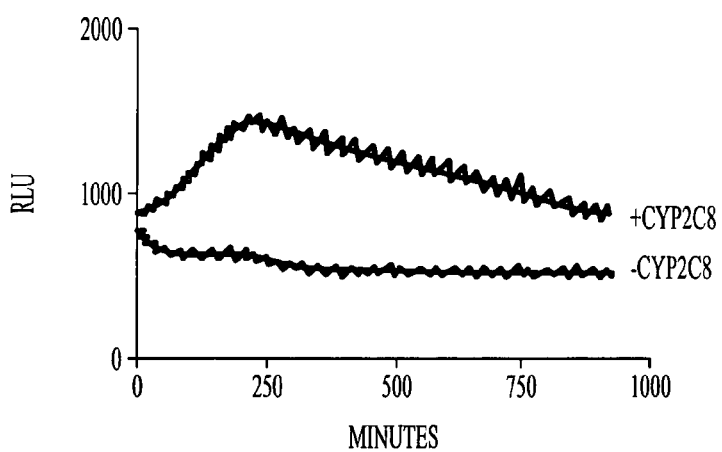
Figure 6C:
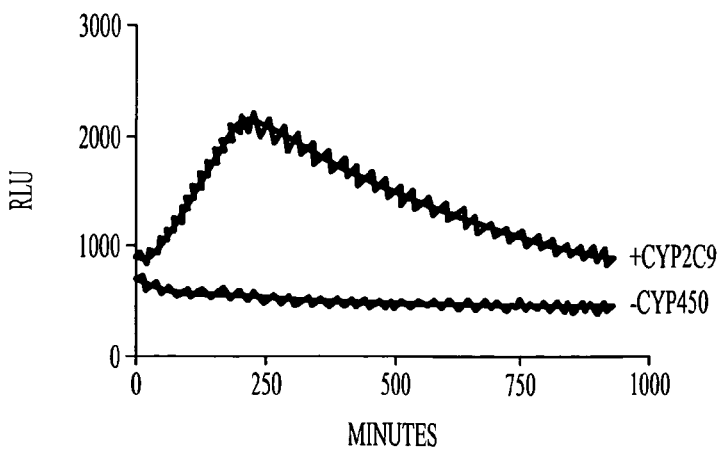
Figure 7A:
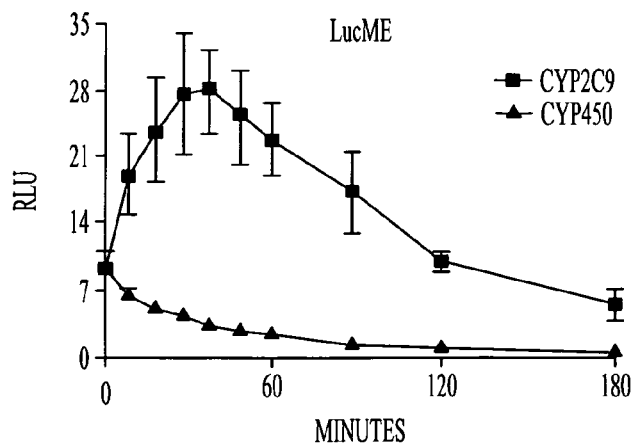
FIG. 7. One-step luminescent CYP450 assays at 37° C. D-luciferin derivatives were incubated in combined CYP450 and luciferase reaction mixes at 37° C. For —CYP450 controls CYP450 Sf9 cell microsomes were replaced with H₂O. CYP450 and a luciferase reaction mix were added simultaneously to a CYP450 reaction mix and light output was read immediately (time=0). Readings were then taken every 10 minutes for 3 hours on a Turner 20/20 luminometer.
Figure 7B:
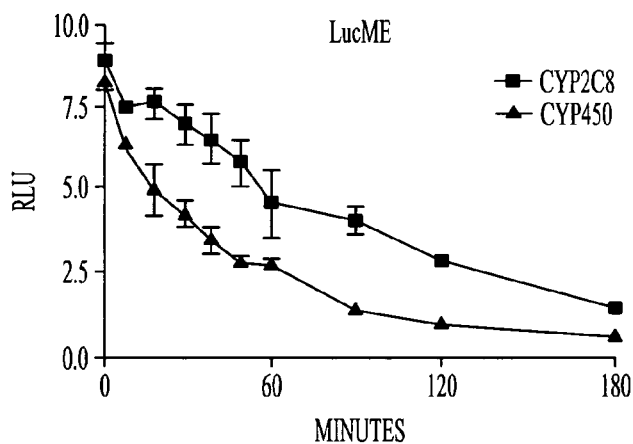
Figure 7C:
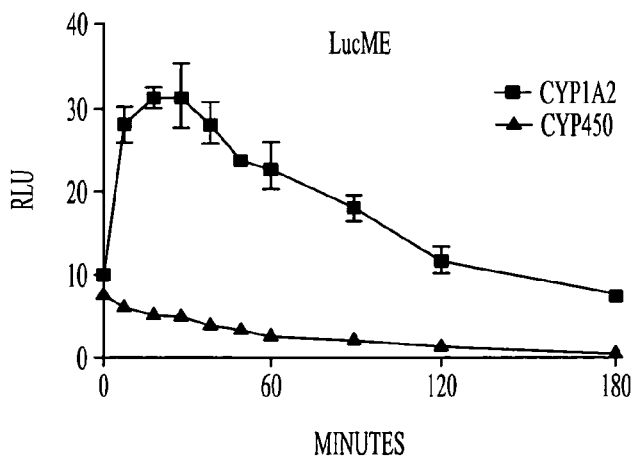
Figure 7D:
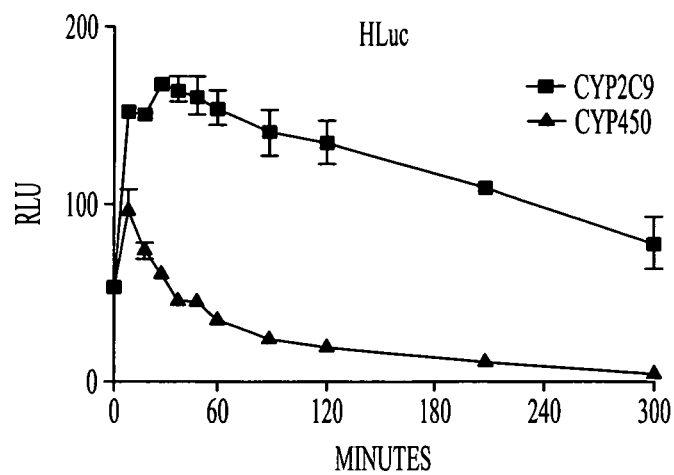
Figure 7E:
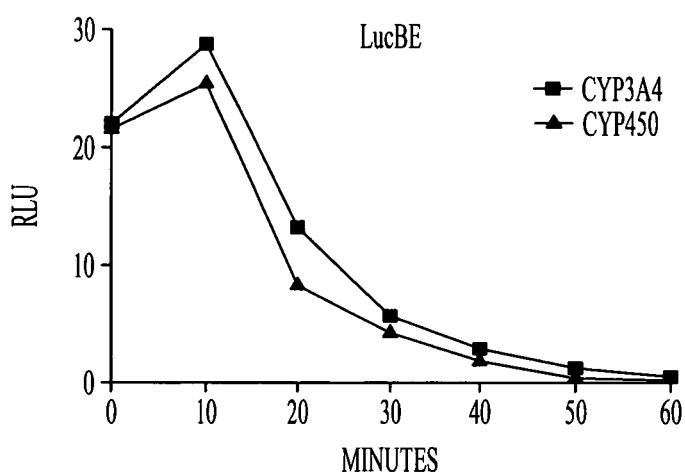
Figure 8A:
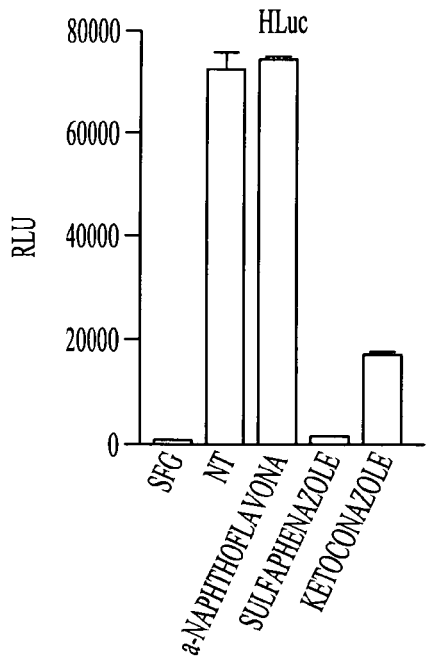
FIG. 8. Pooled human liver microsomes in two-step luminescent CYP450 reactions. D-luciferin derivatives were incubated in a CYP450 reaction mix with pooled human liver microsomes for 60 minutes at 37° C. before combining with a luciferase reaction mixture. For controls liver microsomes were replaced with control (no CYP450) Sf9 cell membranes. Luminescence was read within 12 minutes of combining the reactions on a Berthold Orion luminometer. Vehicle for sulfaphenazole, ketoconazole and alpha-naphthoflavone was 1% acetonitrile and 1 mg/mL bovine serum albumin in H₂O. Values labeled "nt" are vehicle controls. Concentrations of sulfaphenazole, ketoconazole and alpha-naphthoflavone in the reactions were 100 micromolar, 100 micromolar and 10 micromolar, respectively.
Figure 8B:
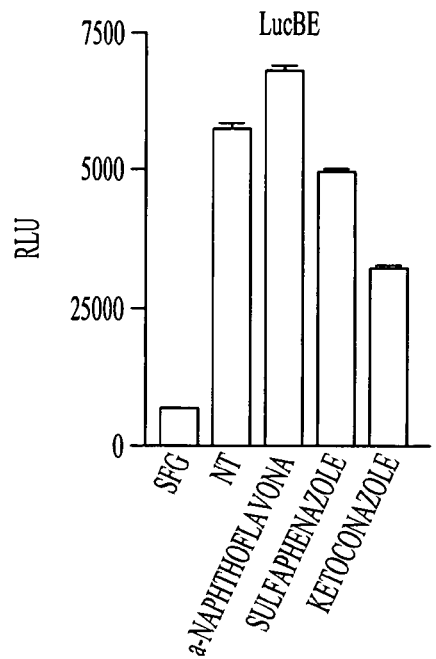
Figure 8C:
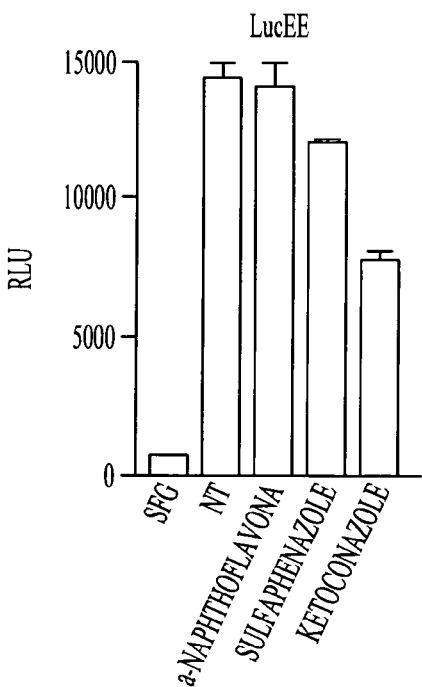
Figure 8D:
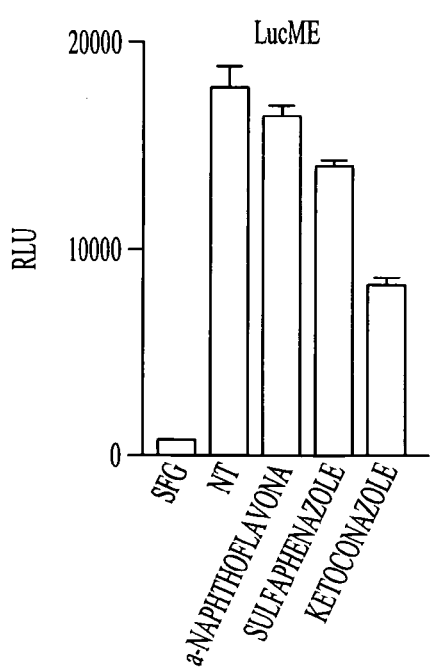
Figure 10A:
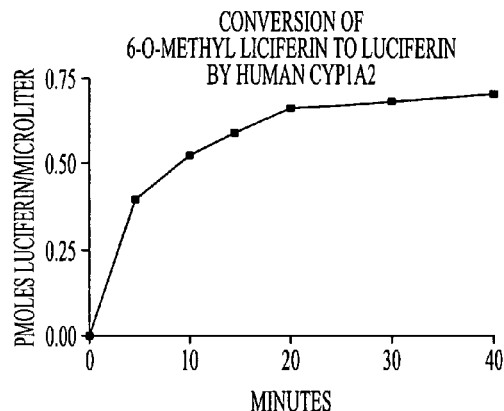
FIG. 10. CYP450-catalyzed conversion of luciferin derivatives to luciferin. Luciferin derivatives (100 micromolar) were incubated in a CYP450 reaction mix for the indicated time intervals. At the end of each time interval, the reaction mixture was quenched with Tergitol to 0.1% (v/v), then frozen in liquid nitrogen. 95 microliter aliquots of the reaction mixture were analyzed by HPLC and luciferin was detected by fluorescence with excitation at 330 nm and emission at 520 nm. The zero time points represent the luciferin content of the derivatives from controls (no enzyme).
Figure 10B:
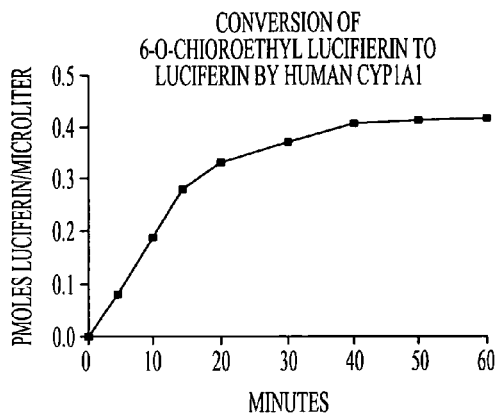
Figure 10C:
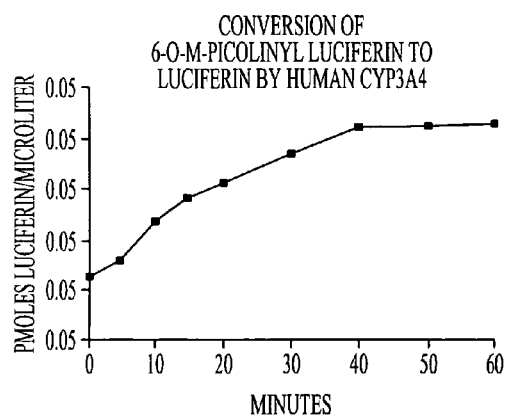
Figure 10D:
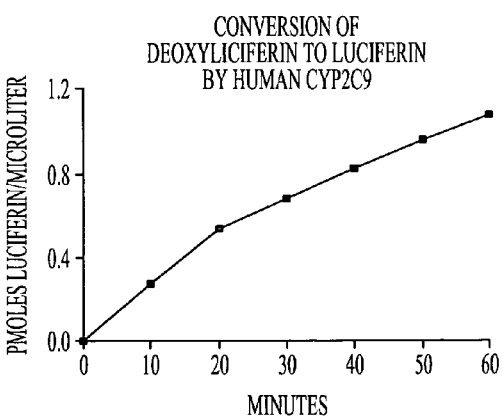

The one-step assays were performed at room temperature (~22° C.) with Luc ME, which was co-incubated with CYP1A2, CYP2C8 and CYP2C9 microsome preparations, and luciferase with its requisite cofactors. Initial baseline luminescence was measured and then light output was monitored over time from the point reactions were initiated by adding CYP450 (FIG. 6). For each reaction a time dependent increase in light output was observed when CYP450 was included in the reaction mix. The most robust response at room temperature was seen with CYP1A2. Light output increased to a maximum level after about forty minutes, remained steady for about 3 hours and then declined gradually over the remainder of the assay. Light output from CYP2C8 and CYP2C9 room temperature reactions increased gradually for about 3 hours, remained steady for about 1 hour then declined gradually over the remainder of the assay. Similar one-step assays were also performed with H-Luc and CYP2C9 and with Luc EE and CYP2C8 (data not shown).

Example 6

One Step CYP450/Luciferase Reaction at 37° C.

In this Example, the one step assay of Example 5 was performed at 37° C. and light was monitored over time from the point where the reactions were initiated by adding CYP450 (FIG. 7). Cyp1A2, CYP2C8 and CYP2C9 were assayed against Luc ME, CYP2C9 against H-Luc and CYP3A4 against Luc BE. Cyp1A2 and CYP2C9 were similar, increasing to a peak of light output by about 30 minutes and declining thereafter. In a CYP2C8 reaction light output exceeded that from a —CYP450 control but declined from initial values over the course of the reaction in both test and control conditions. CYP2C9 with H-Luc was similar to Luc ME, increasing to a maximum by about 30 minutes and declining thereafter. The difference in light output between CYP3A4 with Luc BE and a —CYP450 control was modest. Light output from —CYP450 controls in each case was likely a consequence of luciferin contamination in the unreacted D-luciferin derivative preparation.

Example 7

Pooled Human Liver Microsomes in Two-Step Luminescent CYP450 Reaction

A pooled human liver microsome preparation containing a mixture of CYP450 activities was used in two-step luminescent CYP450 assays that employed H-Luc, Luc ME, Luc EE and Luc BE (FIG. 8) as substrates. As compared to Sf9 cell membranes with no CYP450 activity significant amounts of CYP450 activity was detected by the luminescent method with each substrate. The contributions of individual isoforms to the total light output were implied by inhibition with sulfaphenazole (CYP2C9 inhibitor), alpha-naphthoflavone (CYP1A2 inhibitor) and ketoconazole (CYP2C8 and CYP3A4 inhibitor) (13). Of particular note was the near complete inhibition of light output with H-Luc by the CYP2C9 selective inhibitor sulfaphenazole. Partial inhibition of the H-Luc reaction by 100 micromolar ketoconozole is also consistent with the effect of this inhibitor on CYP2C9 activity. This coupled with the demonstration the H-Luc is selective for CYP2C9 (FIG. 3) indicates that the microsomal activity against H-Luc is predominantly CYP2C9. The effects of sulfaphenazole and ketoconazole on Luc ME and Luc EE activity are consistent with the presence of CYP2C8 activity because CYP2C8 is active against both of these substrates and inhibited by both inhibitors. Inhibition of Luc BE activity by ketoconazole is consistent with the presence of CYP3A4 and/or CYP2C8 because both isoforms are active against Luc BE and both are inhibited by ketoconazole. The lack of inhibition by alpha-naphthoflavone indicates that there is little or no CYP1A2 activity present in the microsome preparation. The slight stimulation of activity against Luc BE by alpha-naphthoflavone may reflect the presence of CYP3A4 activity because this isoform is stimulated by alpha-naphthoflavone (16).

Example 8

Detection of CYP450 Inhibition by Known P450 Inhibitors

Luciferin derivatives as substrates for luminescent CYP40 assays should be useful as probes for detecting CYP450 inhibition by drugs or other xenobiotics. To test this hypothesis, known CYP450 inhibitors and certain luciferase derivatives were added to the reactions and IC50s were determined. Inhibitors tested were sulfaphenazole for CYP2C9, alpha-naphthoflavone for CYP1A2, and ketoconazole for CYP2C8 and 3A4. Two-step assays were performed as described in Example 2. These drugs inhibited the reactions in a dose-dependent manner (Table 1). In many cases, the IC50s were comparable to those reported for assays with other substrates (13). The inhibitors were acting on the CYP450s. Inhibition of luciferase was not detected in control assays that used luciferin as substrate (data not shown).

Table 1 summarizes the inhibition of CYP450 reactions with conventional substrates and D-luciferin derivatives by ketoconazole, alpha-naphthoflavone and sulfaphenazole. CYP450 assays with luciferin derivatives were performed in two steps essentially as described in Example 2. In this case the CYP450s were exposed to inhibitors at concentrations ranging from about 40 nM to 10 micromolar for 10 minutes prior to exposure to a D-luciferin derivative. $IC_{50}S$ were calculated by non-linear regression analysis with GraphPad Prism software. Entries marked with an asterisk were taken from reference 13.

TABLE 1

Inhibition of CYP450 reactions by CYP450 inhibitors.

| P450/substrate | Alpha-Naphptho-flavone | Ketoconazole | Sulfa-phenazole |
|---|---|---|---|
| CYP1A2/Luc ME | 0.2 | — | — |
| CYP1A2/ethoxyresorufin* | 0.4 | — | — |
| CYP1A2/phenanthrene* | 3.8 | — | — |
| CYP1A2/imaprine* | 0.1 | — | — |
| CYP2C8/Luc EE | — | 26.4 | — |
| CYP2C8/phenanthrene* | — | 8.9 | — |
| CYP2C9/H-Luc | — | — | 0.7 |
| CYP2C9/Luc ME | — | — | 0.4 |
| CYP2C9/Luc EE | — | — | 0.5 |
| CYP2C9/diazepem* | — | — | 0.5 |
| CYP2C9/phenanthrene* | — | — | 0.7 |
| CYP3A4/Luc BE | — | 0.06 | — |
| CYP3A4/diazepem* | — | 0.5 | — |

TABLE 1-continued

Inhibition of CYP450 reactions by CYP450 inhibitors.

| P450/substrate | Alpha-Naphpthoflavone | Ketoconazole | Sulfaphenazole |
|---|---|---|---|
| CYP3A4/phenanthrene* | — | 0.03 | — |
| CYP3A4/testosterone* | — | 0.04 | — |

$IC_{50}$s (micromolar) against CYP450 isoform/substrate reactions are shown.
*From reference 13.

Example 9

CYP450-Catalyzed Conversion of Luciferin Derivatives to Luciferin

In this Example, the conversion of Luc ME, H-Luc, Luc CEE and Luc 3PE to luciferin by cytochrome P450 enzymes was confirmed by HPLC analysis (FIG. 10). 100 micromolar Luc ME, H-Luc, Luc CEE and Luc 3PE was incubated with CYP1A2, CYP2C9, CYP1A1 and CYP3A4, respectively in reaction volumes of 150 microliters at 37 C. At various time intervals, the reactions were stopped by the addition of Tergitol to 0.1% (v/v) and flash freezing in liquid nitrogen. 95 microliter aliquots of each reaction mixture were subjected to fractionation by HPLC. HPLC method: High-performance liquid chromatography was performed on an HP 1050 LC system equipped with a multi-wavelength absorbance (HP 1050 MWD) and fluorescence detector (HP 1046A). Separation was achieved on a 5 micron Adsorbosphere HS C18 column (Alltech Associates) with a solvent gradient of 0.05M $KH_2PO_4$/pH 6 (solvent A) and 80:20 acetonitrile/water (solvent B). The gradient conditions used were 15% B to 95% B over 10 min. Substrates were detected by absorbance at either 262 or 330 nm and Luciferin was detected by fluorescence at 520 nm (emission) with an excitation wavelength of 330 nm. The zero time points represent the luciferin content of deoxyluciferin or luciferin 6' methyl ether from no enzyme controls.

Example 10

Detection of CYP450 Inhibition by Known CYP450 Substrates

Figure 11A:
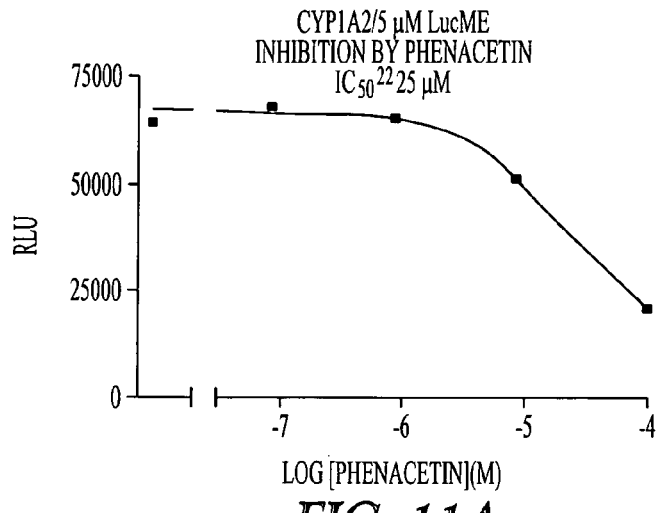
FIG. 11. Detection of Cyp450 inhibition by known CYP450 substrates. Luciferin derivatives as substrates for luminescent CYP450 assays were evaluated as probes for detecting other CYP450 substrates. CYP450 substrates tested were diclofenac for CYP2C9 and phenacetin for CYP1A1 and CYP1A2. The reactions were performed as described in Example 1 except the first step (CYP450 reaction) was in a 50 microliter reaction volume with 1 picomole of CYP450. In the second step a 50 microliter luciferase reaction was added to give final concentrations of 50 micrograms/mL Ultra Glo luciferase, 200 micromolar ATP, 0.1% Tergitol (v/v), 4.0 mM MgSO₄ and 100 mM Tricine pH 8.4. Panel A illustrates inhibition of CYP1A2 by phenacetin using Luc ME as substrate. Panel B illustrates inhibition of CYP1A1 by phenacetin using Luc CEE as substrate. Panel C illustrates inhibition of CYP2C9 by diclofenac using HLuc as substrate.
Figure 11B:
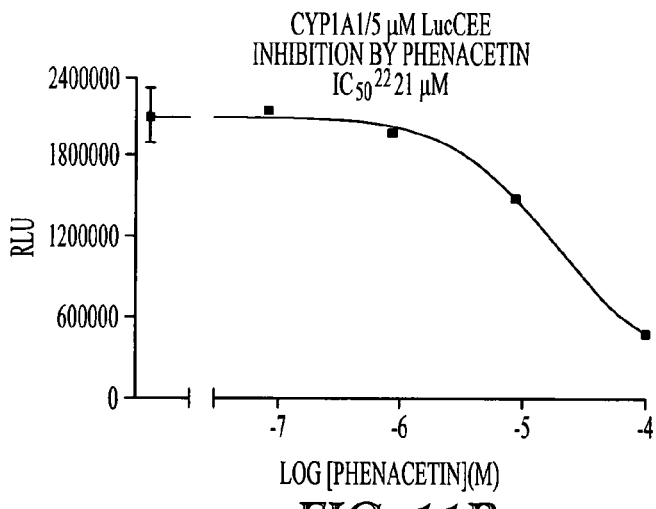
Figure 11C:
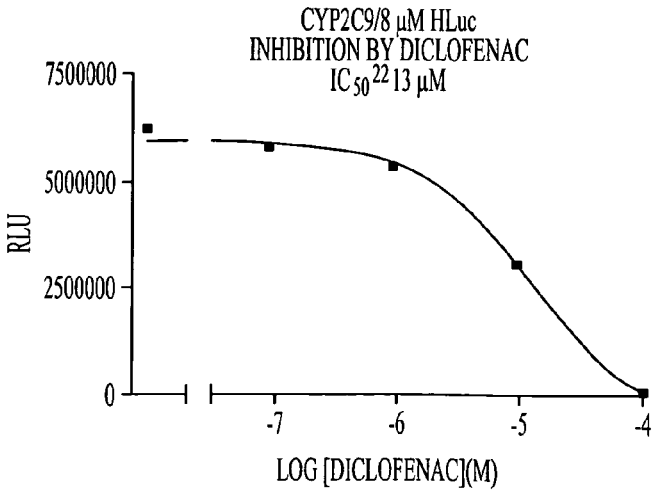
Figure 12A:
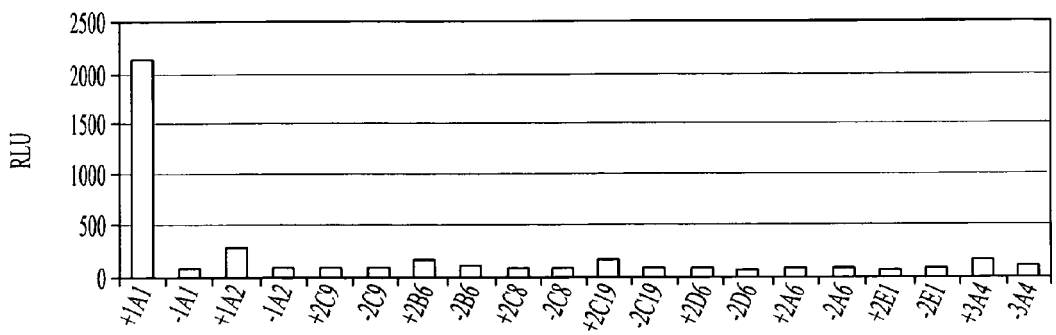
FIG. 12: P450 action on methoxy-coelenterazine HH, coelenterazine HH and coelenterazine by chemiluminescent and bioluminescent detection. Panel A shows bioluminescence from methoxy-coelenterazine-HH in relative light units (RLU) generated in a *Renilla* luciferase containing reaction following incubation of methoxy-coelenterazine HH with (+) or without (−) various P450 isozymes. Panel B shows the fold increase in bioluminescence from reactions containing methoxy-coelenterazine HH and P450 (+P450 RLU/−P450 RLU). Panel C shows chemiluminescence from methoxy-coelenterazine HH in RLU generated following incubation of methoxy-coelenterazine HH with (+) or without (−) various P450 isozymes. Panel D shows the fold increase in chemiluminescence from reactions containing methoxy-coelenterazine HH and P450 (+P450 RLU/−P450 RLU). Panel E shows bioluminescence from coelenterazine HH in RLU generated in a *Renilla* luciferase containing reaction following incubation of coelenterazine HH with (+) or without (−) various P450 isozymes. Panel F shows the fold decrease in bioluminescence from reactions containing coelenterazine HH and P450 (+P450 RLU/−P450 RLU). Panel G shows chemiluminescence from coelenterazine HH in RLU generated following incubation of coelenterazine HH with (+) or without (−) various P450 isozymes. Panel H shows the decrease in chemiluminescence from reactions containing coelenterazine HH and P450 (+P450 RLU/−P450 RLU). Panel I shows bioluminescence from coelenterazine in RLU generated in a *Renilla* luciferase containing reaction following incubation of coelenterazine with (+) or without (−) various P450 isozymes. Panel J shows the decrease in bioluminescence from reactions containing coelenterazine and P450 (+P450 RLU/−P450 RLU). Panel K shows chemiluminescence from coelenterazine in RLU generated following incubation of coelenterazine with (+) or without (−) various P450 isozymes. Panel L shows the decrease in chemiluminescence from reactions containing coelenterazine and P450 (+P450 RLU/−P450 RLU).
Figure 12B:
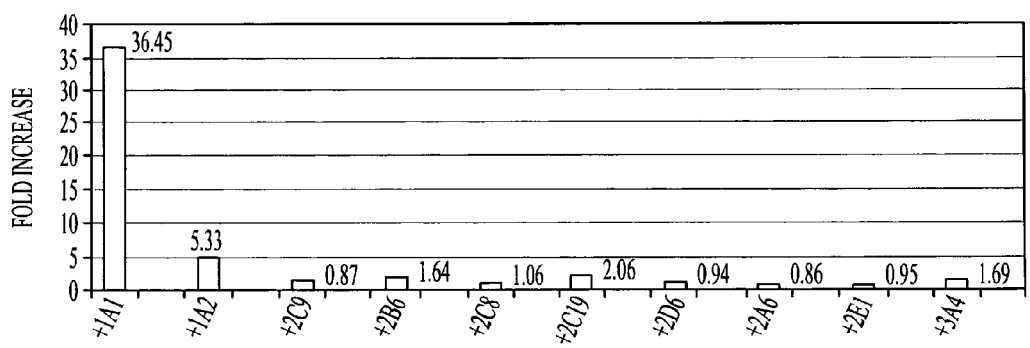
Figure 12C:
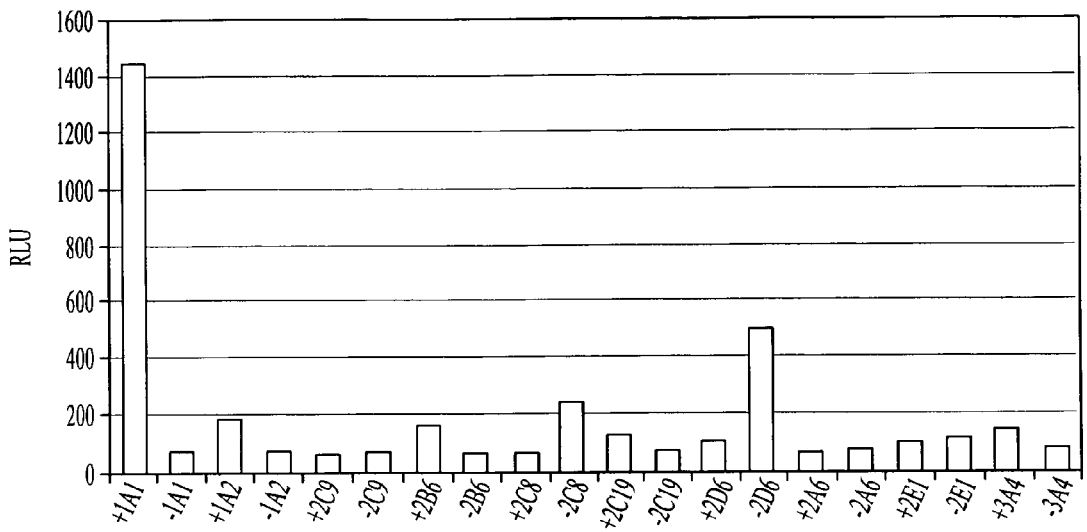
Figure 12D:
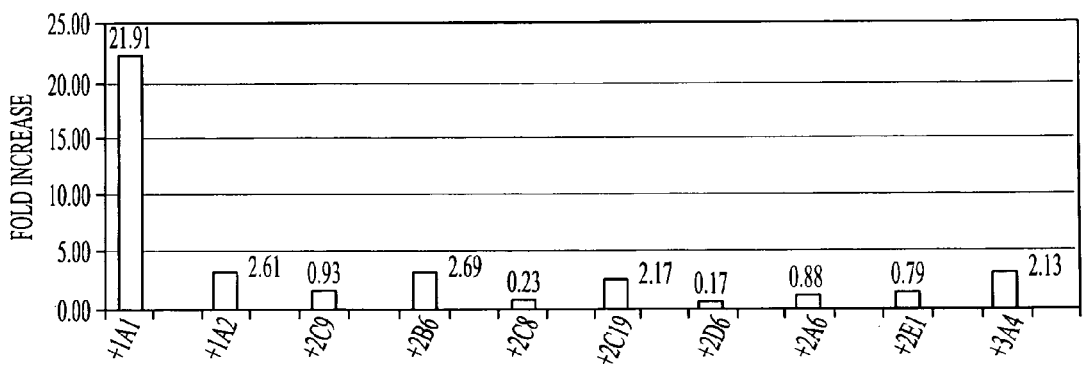
Figure 12E:
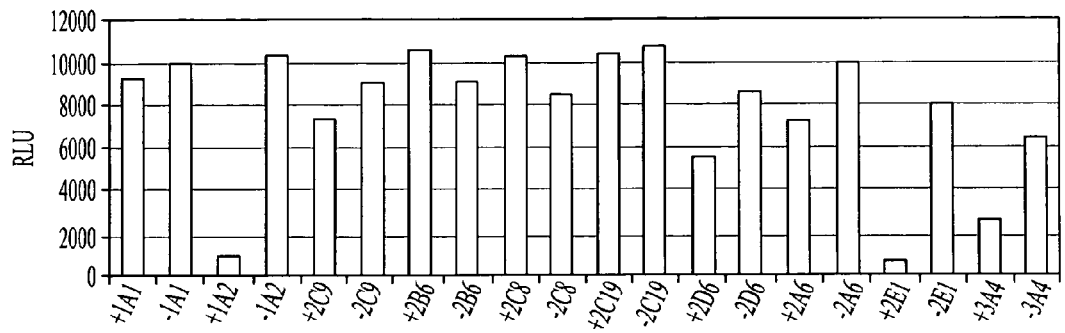
Figure 12F:
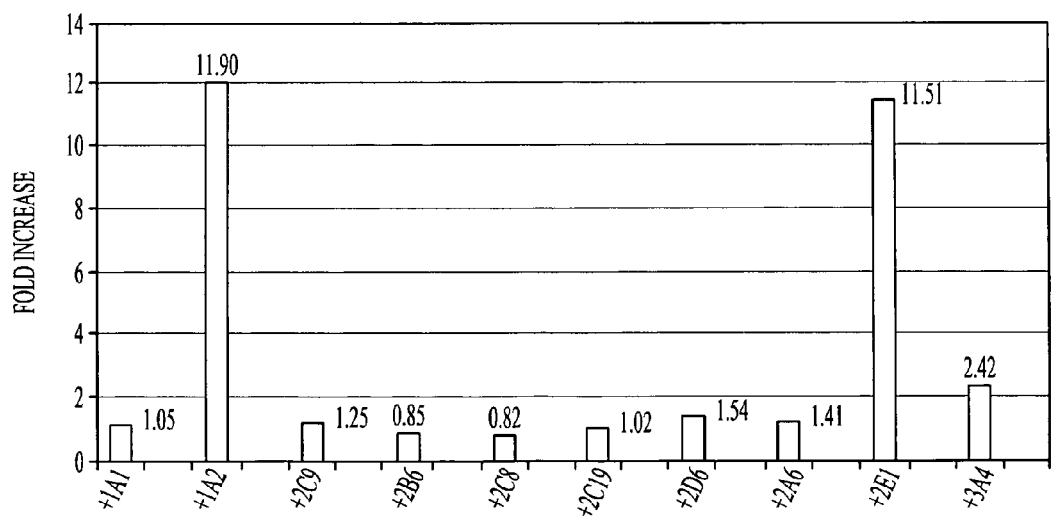
Figure 12G:
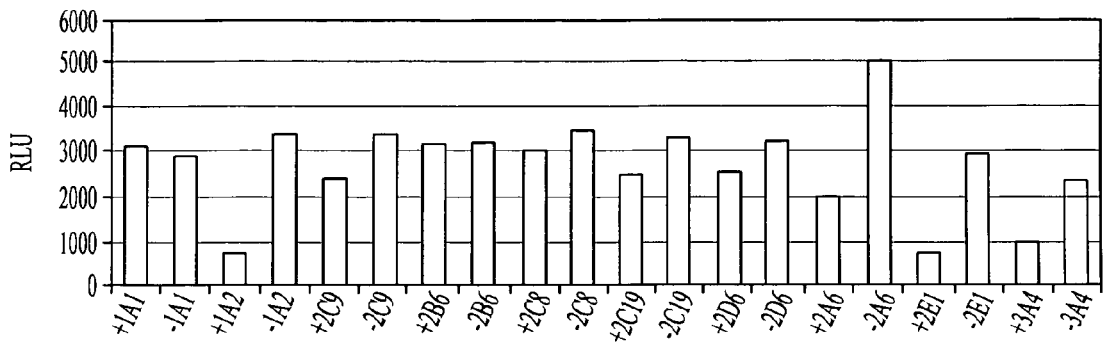
Figure 12H:
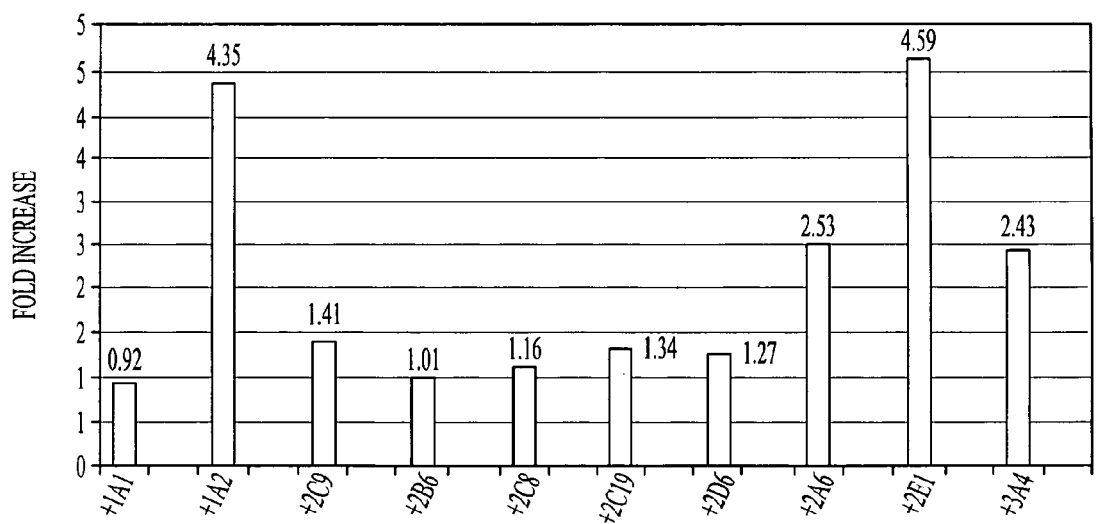
Figure 12I:
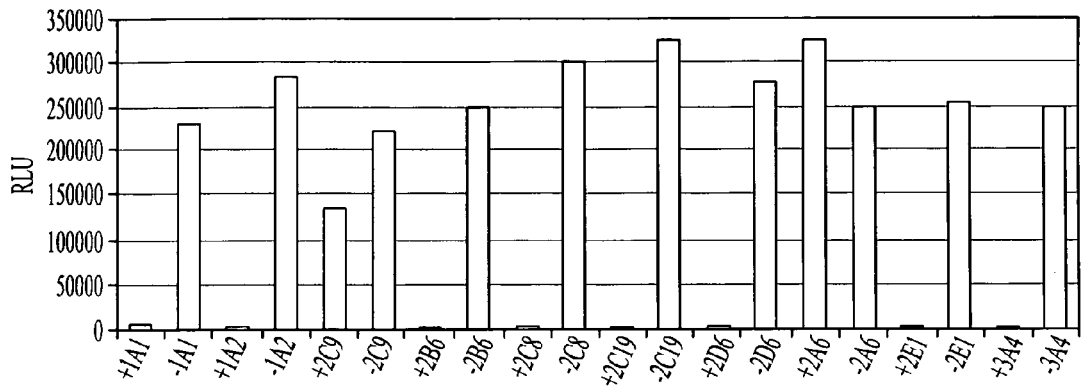
Figure 12J:
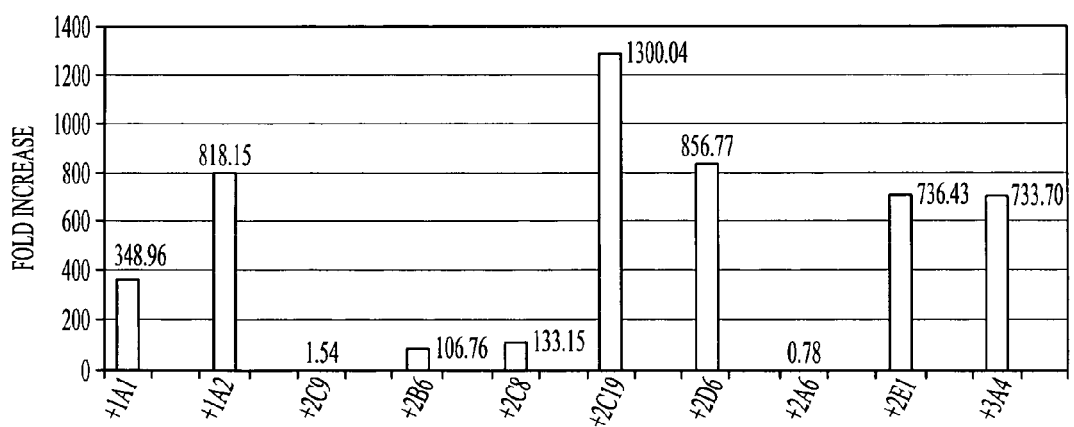
Figure 12K:
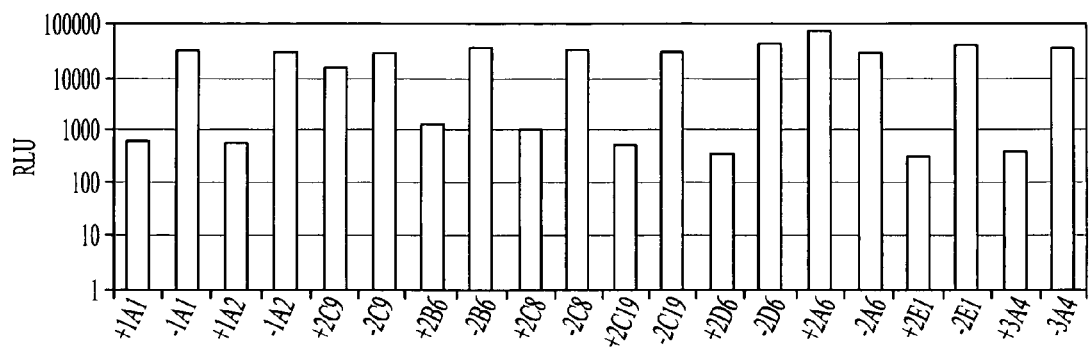
Figure 12L:
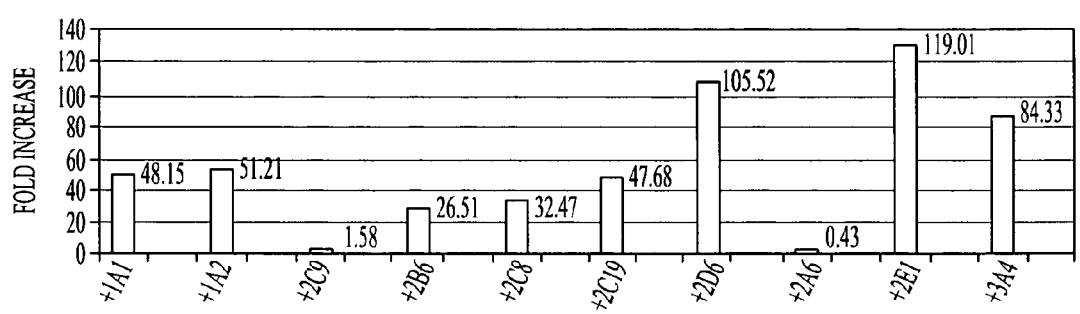

Luciferin derivatives as substrates for luminescent CYP450 assays would be useful as probes for detecting other CYP450 substrates. Because two distinct substrates for the same CYP450 isoform will likely compete for the active site, it is possible to characterize known substrates and to identify novel substrates by observing their capacity to inhibit the luminescent reactions with luciferin derivatives. To test this hypothesis, known CYP450 substrates were added to the reactions (Tassaneeyakul, W. et al (1993) "Specificity of substrate and inhibitor probes for human cytochromes P450 1A1 and 1A2", *J. Pharmacol. Exp. Ther.*, 265, 401-407; Mancy, A. et al "Diclofenac and its derivatives as tools for studying human cytochromes p450 active sites: particular efficiency and regioselectivity of p450 2Cs", *Biochemistry*, 38, 14264-14270). Substrates tested were diclofenac for CYP2C9 and phenacetin for CYP1A1 and CYP1A2. The drugs inhibited the reactions in a dose-dependent manner, thus verifying the expectation that CYP450 substrates can be detected by these luminescent assays (see table below). IC50s were calculated by non-linear regression analysis with the program GraphPad PRISM™ (San Diego, Calif.). The reactions were performed as described in Example 2 except the first step (CYP450 reaction) was in a 50 microliter reaction volume with 1 picomole of CYP450. In the second step a 50 microliter luciferase reaction was added to give final concentrations of 50 micrograms/mL recombinant, mutant of firefly luciferase from *Photuris pennsylvanica* from Promega (17), 200 micromolar ATP, 0.1% tergitol (v/v), 4.0 mM $MgSO_4$ and 100 mM Tricine pH 8.4. FIGS. 11(a)-(c) illustrate the actual inhibition curves.

TABLE 2

| CYP450 isoform/substrate | Diclofenac | Phenacetin |
|---|---|---|
| CYP2C9/H-Luc | 13 | ND |
| CYP1A1/Luc CEE | ND | 21 |
| CYP1A2/Luc ME | ND | 25 |

Values shown are $IC_{50}$S (micromolar).

Example 11

Two-step Cyp450/*Renilla* Reaction and Coelenterazine Derivative Evaluation

In this Example, P450 activity was determined using coelenterazine and coelenterazine derivatives, methoxy-coelenterazine HH and coelenterazine HH, in a two-step reaction system. In these assays, P450 acts on the coelenterazine or coelenterazine derivatives in one of two ways. In the first type of reaction coelenterazine derivatives that are neither substrates for *Renilla*-type luciferases nor exhibit the characteristic coelenterazine chemiluminescence (luminescence in the absence of luciferase) are altered by P450 to become substrates for *Renilla*-type luciferase and exhibit chemiluminescence. An example of this type of coelenterazine derivative is methoxy-coelenterazine HH. In the second type of reaction coelenterazine or coelenterazine HH, which exhibit chemiluminescence and are competent substrates for *Renilla*-type luciferase, are altered by P450 resulting in a loss of chemiluminescence and activity with *Renilla*-type luciferases. In both types of assay it is possible to detect P450 activity either directly by a change in chemiluminescence or indirectly by a change in bioluminescence from a *Renilla*-type luciferase.

(I) Synthesis of Coelenterazine Derivatives

2-Oxo-3-phenyl-propionaldehyde

Phenylpyruvic acid (25.0 g, 152.0 mmol) was coevaporated twice with dry pyridine and then redissolved in dry pyridine (250 mL). To this solution was added acetic anhydride (170 mL, 1.8 moles) and the solution was stirred at ambient temperature for 15 h. The reaction progress was monitored by TLC. When the reaction was complete, the solution was evaporated to a viscous syrup. The syrup was dissolved in dichloromethane (700 mL) and then washed three times with 0.1 M aqueous HCl solution (3×200 mL). The organic phase was dried over anhydrous sodium sulfate, filtered and evaporated to an amber-colored syrup. This product was purified by flash chromatography on silica gel (250 g) using dichloromethane as mobile phase. Appropriate fractions were pooled and evaporated to afford 24 g of a dry solid. This material was dissolved in THF (150 mL) and the solution was cooled in an ice-water bath. To the solution was added dropwise oxalyl chloride (51 mL, 580 mmol). After 10 min DMF (7.5 mL) was added to the reaction mixture and the reaction was stirred for 4 h at 0° C. Toluene (100 mL) was added and the reaction mixture was evaporated to give a thick oil. This material was coevaporated twice with toluene and the crude product was dried under vacuum for 5 h. The dried product was dissolved in a 1:1 mixture of THF-dichloromethane (200 mL) and the solution was cooled to −78° C. (dry ice-isopropanol bath) under argon. Then, lithium tri-tert-butoxyaluminohydride (152 mL of a 1.0 M solution in THF, 152 mmol) was added at a rate such that the internal temperature of the reaction was below 60° C. After addition was complete, the reaction was stirred below −60° C. for 10 h. The reaction was quenched by the slow addition of 2 M aqueous HCl solution (100 mL) and the mixture was allowed to warm to ambient temperature. The reaction mixture was diluted with dichloromethane (500 mL) and then washed twice with 0.1 M aqueous HCl solution (2×100 mL). The organic phase was dried over anhydrous sodium sulfate, filtered and evaporated to give an amber-colored syrup. This material was purified by flash chromatography on silica gel (250 g) starting with 95:5 heptane-ethyl acetate, then with 9:1 heptane-ethyl acetate as mobile phase. Appropriate fractions were pooled and evaporated to afford 13.5 g (80%) of the desired compound.

2,8-Dibenzyl-6-phenyl-7H-imidazo[1,2-a]pyrazin-3-one (Coelenterazine HH)

A solution of 2-amino-3-benzyl-5-phenylpyrazine[20] (2.0 g, 8.0 mmol) and 2-oxo-3-phenyl-propionaldehyde (3.0 g, 16 mmol) in ethanol (125 mL) was deoxygenated with argon gas for 20 min. To the solution was added concentrated hydrochloric acid (4.0 mL) and the reaction mixture was heated at reflux for 18 h. The reaction was allowed to cool to ambient temperature and then evaporated to a brown solid. The crude product was triturated with ethanol (40 mL) and the resulting solid material was collected by centrifugation and then dried in a vacuum oven to afford 1.28 g (41%) of the desired compound. This product was 80% pure according to HPLC analysis.

2,8-Dibenzyl-3-methoxy-6-phenyl-imidazo[1,2-a]pyrazine (Coelenterazine HH methyl ether)

To a stirred solution of 2,8-dibenzyl-6-phenyl-7H-imidazo[1,2-a]pyrazin-3-one (0.25 g, 0.6 mmol) in dry DMF (10 mL) at ambient temperature under argon was added diisopropylethylamine (1.1 mL, 6.0 mmol) all at once, followed by dropwise addition of methyl iodide (0.4 mL, 6.0 mmol). After stirring for 1 h the reaction was complete by TLC analysis. The reaction mixture was diluted with dichloromethane (75 mL) and washed twice with water. The organic extracts were dried over anhydrous sodium sulfate, filtered and evaporated to provide a brown oil. The crude oil was purified by flash chromatography on silica gel (30 g) using dichloromethane as mobile phase. Appropriate fractions were pooled and evaporated to afford 200 mg (77%) of the desired compound.

(II) P450 Assays

P450 reactions (20 microliter) containing 200 mM $KPO_4$ pH 7.4 (for CYP3A4) or 100 mM $KPO_4$ pH 7.4 for (CYP1A1, 1A2, 2B6, 2D6, 2E1) or 50 mM $KPO_4$ pH 7.4 (for CYP2C8, 2C19) or 25 mM $KPO_4$ pH 7.4 (for CYP2C9) or 100 mM Tris pH 7.5 (for CYP2A6); insect cell microsomes containing baculovirus expressed P450 (1 pmole) and P450 reductase or for no P450 control reactions wild type baculovirus infected insect cell microsomes; 1.3 mM $NADP^+$; 3.3 mM Glucose-6-Phosphate; 3.3 mM MgCl; 0.4 units/ml Glucose-6-Phophate Dehydrogenase; and substrate (3 micromolar Coelenterazine, 3 micromolar Coelenterazine HH and 10 micromolar Methoxy-coelenterazine HH) were incubated for 60 min at 37° C.

Chemiluminescence of P450 altered coelenterazine or coelenterazine derivatives was determined immediately following addition of 80 microliter of 37.5 mM Hepes pH7.4; 625 mM KCl; 0.125 mM EDTA pH 8.0; 0.25% Triton X-100; 0.125% Mazu; 1.25% Glycerol; 0.25 mg/mL gelatin to the P450 reactions. *Renilla* luciferase (1.2 ng/mL) (purchased from Chemicon) was added for detection of bioluminescence of P450 altered coelenterazine or coelenterazine derivatives.

As shown in FIG. 12, there was a large increase in both chemiluminescence (panels C and D) and bioluminescence (panels A and B) following incubation of methyl-coelenterazine HH with CYP1A1. There were modest increases in chemiluminescence and bioluminescence with CYP1A2, 2B6 and 2C19 (2-5×). There was a significant reduction in both chemiluminescence (panels G and H) and bioluminescence (panels E and F) following incubation of coelenterazine HH with CYP1A2 and 2E1. Finally, there was a very large reduction in both chemiluminescence (panels K and L) and bioluminescence (panels I and J) following incubation of coelenterazine with all of the P450 isozymes tested except 2C9 and 2A6.

Example 12

Luciferase Protection from Inhibitory Buffer by the Addition of Yeast iPPase

This Example illustrates the reversal of inhibition of a luciferase-based P450 reaction in the presence of inhibitory buffer by iPPase. As defined herein, "inhibitory" refers to a reagent (such as a buffer) that includes iPP in sufficient amounts to inhibit the luciferase reaction. A "non-inhibitory reagent" is a reagent that includes substantially no iPP, as measured by its effect on the luciferase reaction. The iPP content is determined empirically by the finding that firefly luciferase is inhibited by iPP, an inhibition is relieved by addition of iPPase and that the inhibition can be recreated by the addition of PPi.

P450 reactions (50 microliter) contained: 1 pmole CYP1A2 (control reactions contained SF9 membranes), 1.3 mM $NADP^+$, 3.3 mM glucose-6-phosphate, 0.2 U/ml glucose-6-phosphate dehydrogenase, 3.3 mM $MgCl_2$, 0.01 mM Luc-ME and either 100 mM $KPO_4$ pH7.4 (inhibitory buffer) or 100 mM $KPO_4$ pH 7.4 (non-inhibitory buffer). Reactions were incubated at 37° C. for 1 hour. The detection of luciferin generated by the P450 reaction was carried out by addition of equal volume of a reagent containing: thermostable luciferase (100 mg/mL) from *Photuris pennsylvanica* prepared as described in WO/9914336, published Mar. 25, 1999 which is incorporated by reference in its entirety); 400 micromolar ATP, 0.4% Prionex, 40 mM Tricine pH 7.8, 8 mM $MgSO_4$, 0.2% Tergitol. iPPase (Sigma Company, Catalog No. 11891) was added to some of the reactions. Luminescence was detected using a Berthold Orion Microplate Luminometer.

Figure 13:
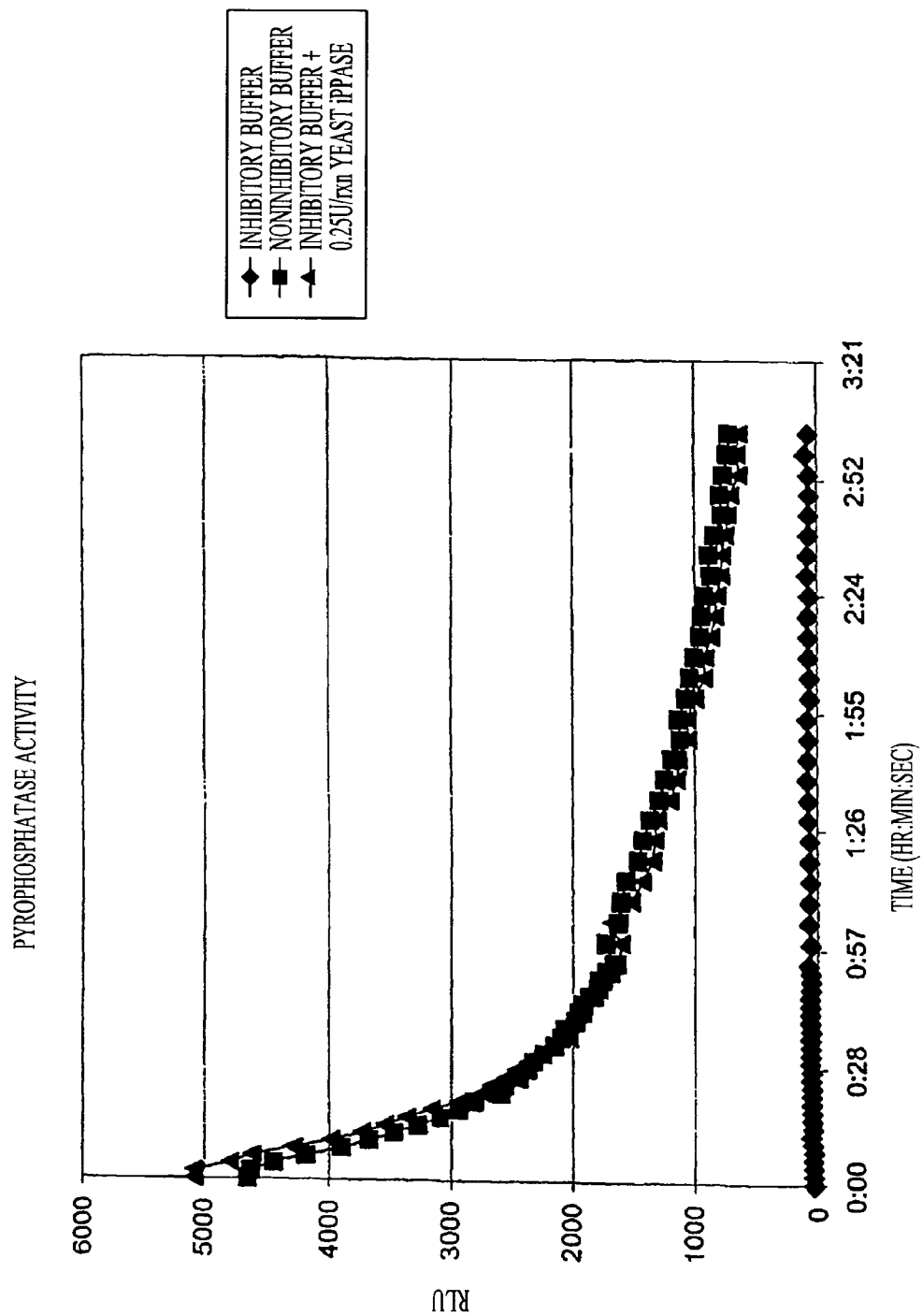
FIG. 13. Protection of luciferase from inhibitory buffer using yeast iPPase. Yeast inorganic pyrophosphatase was found to be effective in reversing iPP inhibition of luciferase when inhibitory KPO₄ buffer used.
Figure 15:
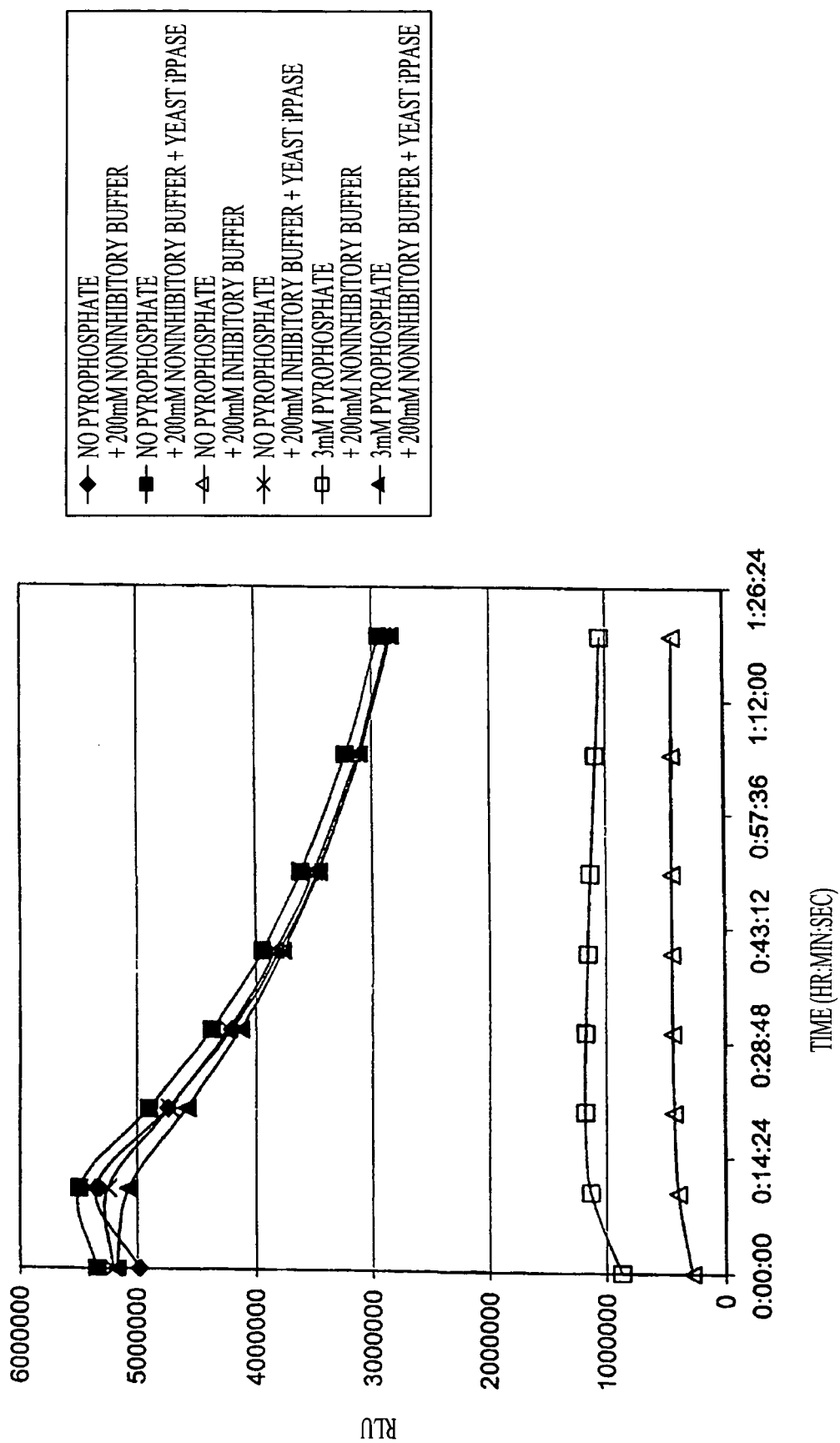
FIG. 15. Protection of luciferase from added iPP using iPPase. Inorganic pyrophosphatase was found to be effective in reversing iPP inhibition of a luciferase-based reaction when iPP is added to the reaction.
Figure 16A:
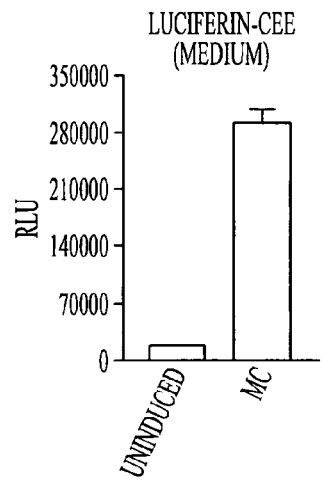
FIG. 16. Cell-based Luminescent CYP450 Assays. Primary rat hepatocytes were treated for 2 days with inducers of CYP450 gene expression: 5 micromolar 3-methylcholanthrene (MC), 50 micromolar dexamthasone (Dex) or 50 micromolar rifampicin (Rif) and their vehicle controls, 0.05, 0.1 and 0.1% DMSO, respectively (uninduced); and an inhibitor of CYP450: 100 micromolar troleandomycin (Tro). The induction medium was then replaced with 300 microliters of 100 micromolar luciferin-CEE (panels A and B), 200 micromolar luciferin-BE or 200 micromolar luciferin-BE plus Tro dissolved in hepatocyte culture medium and allowed to incubate for 4 hours. 100 microliters of medium was then removed from wells and combined with luciferin detection reagent (see example 15) and 200 microliters of luciferin detection reagent was added to the remaining 200 microliters of medium on cells. Luminescence from 200 microliters of culture medium reactions (panels A & C) and cell lysate reactions (panels B & D) was quantified.
Figure 16B:
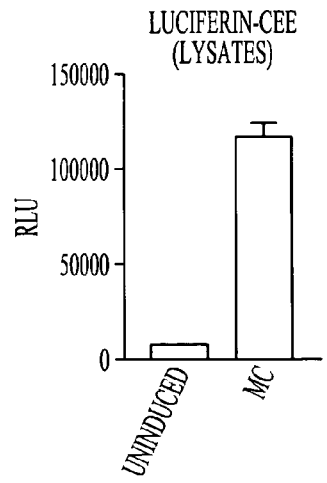
Figure 16C:
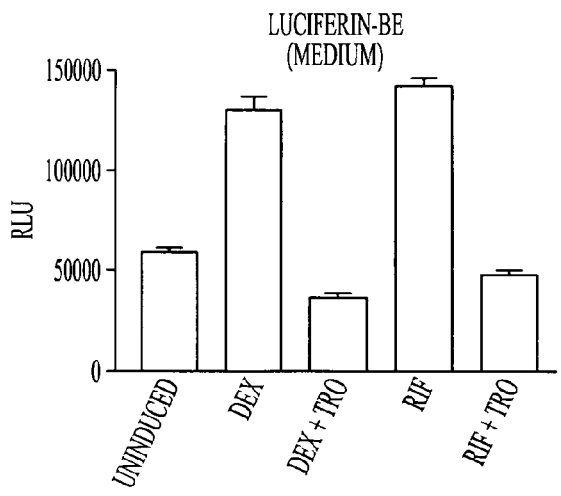
Figure 16D:
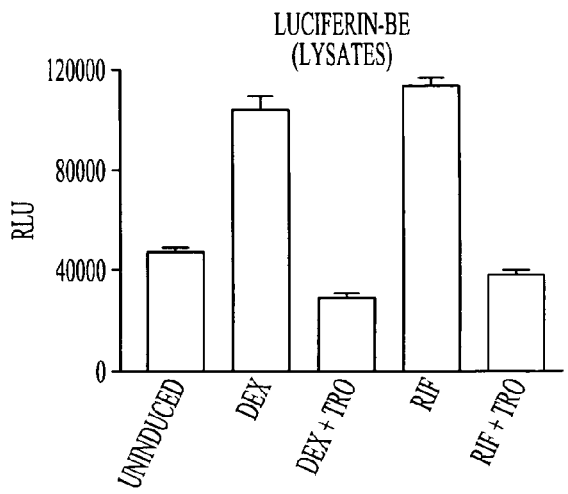

As shown in FIG. 13 and in FIG. 15, yeast inorganic pyrophosphatase was effective in reversing iPP inhibition of luciferase when inhibitory buffer is used.

Example 13

Inorganic Pyrophosphatases Protect Luciferase from Pyrophosphatase Contamination In this experiment, thermostable inorganic pyrophosphatase from three sources, New England Biolabs, Inc. (Beverly, Mass., Catalog #M0296), a commercially available yeast inorganic pyrophosphatase from Sigma (Cat No. 11891), and a pyrophosphatase isolated from *Thermus thermophilus* (Tth), isolated by conventional methods, were evaluated for their efficiencies at reversing the effect of iPP contaminated buffer in a luciferase-based P450 reaction.

In this experiment, P450 reaction mixtures (50 microliter) were prepared. The reactions contained: 1 pmole CYP1A2 (control reactions contained Sf9 membranes), 1.3 mM $NADP^+$, 3.3 mM glucose-6-phosphate, 0.2 U/mL glucose-6-phosphate dehydrogenase, 3.3 mM $MgCl_2$, 0.01 mM LucME, and either 100 mM $KPO_4$ pH7.4 (inhibitory buffer) or 100 mM $KPO_4$ pH 7.4 (non-inhibitory buffer. Reactions were incubated at 37° C. for one hour. The detection of luciferin generated by the P450 reaction was carried out by addition of equal volume of a reagent containing 100 mg/mL thermostable Luciferase from *Photuris pennsylvanica* prepared as described in WO/9914336, published Mar. 25, 1999 which is incorporated by reference in its entirety), 400 mM ATP, 0.6% Prionex, 40 mM Tricine pH 7.8, 8 mM $MgSO_4$, 0.2% Tergitol, 0.02% Mazu. iPPase from New England Biologics, Inc. (Beverly, Mass., Catalog #M0296), Sigma (Cat No. 11891), or *Thermus thermophilus* (Tth), isolated by conventional methods was added to some of the reactions. Following incubation at room temperature for 30 minutes luminescence was detected using a Berthold Orion Microplate Luminometer.

Figure 14:
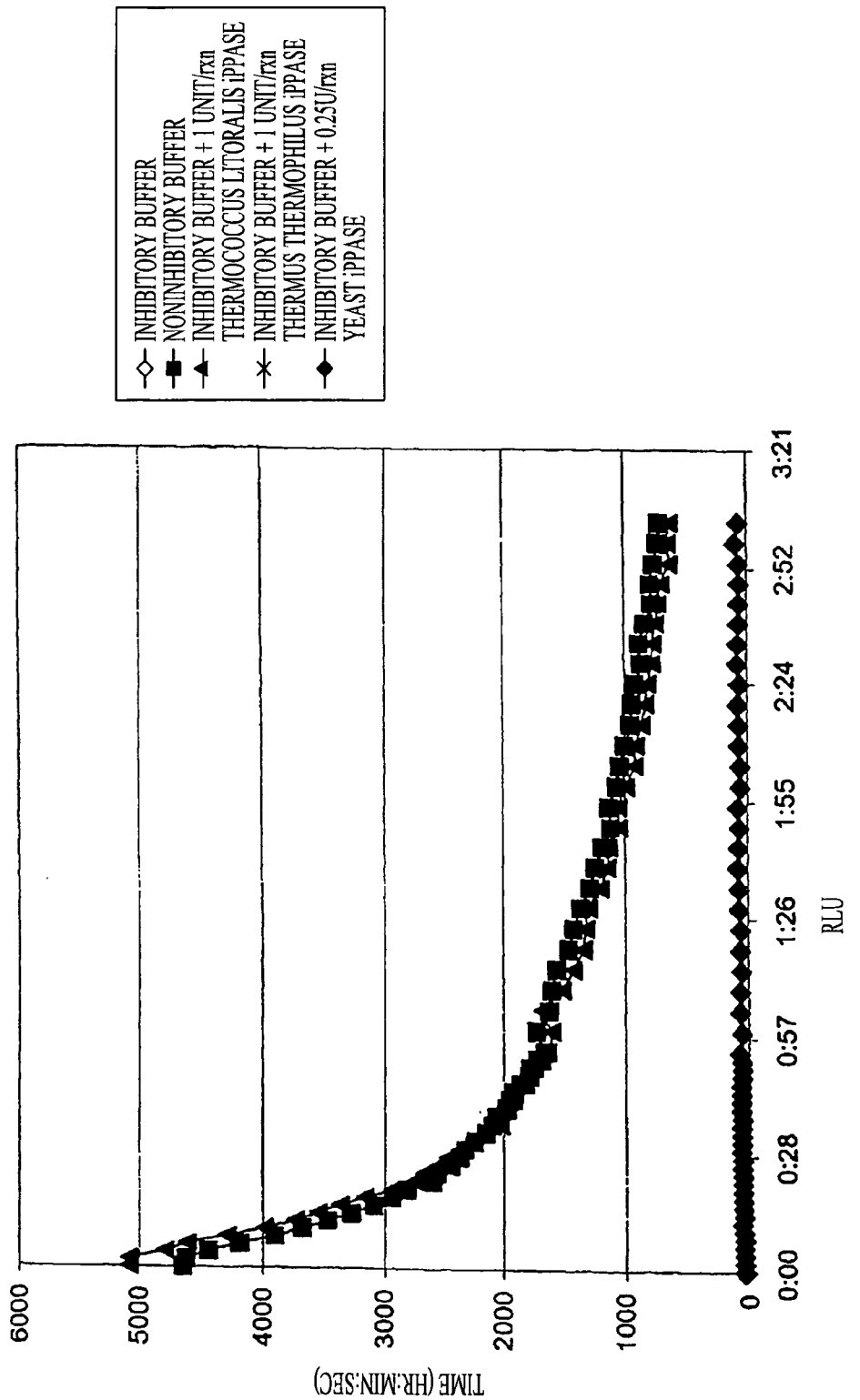
FIG. 14. Inorganic pyrophosphatases protect luciferase from pyrophosphatase contamination. Inorganic pyrophosphatases from different sources were found to reverse iPP inhibition of luciferase when inhibitory KPO₄ buffer is used.

As shown in FIG. 14, inorganic pyrophosphatase from different sources reversed inhibition of luciferase when inhibitory $KPO_4$ buffer is used in a P450 reactions. Reaction conditions, temperature and enzyme concentrations were found to affect the efficiencies of the various iPPase enzymes in reversing iPP inhibition (data not shown).

Example 14

Protection of Luciferase from Added iPP Using Yeast iPPase

This Example illustrates iPPase reversal of inhibition of a luciferase reaction in the presence of added iPP and shows that the performance of 200 mM non-inhibitory $KPO_4$ Buffer with 3 mM NaPPi is similar to that of 200 mM inhibitory $KPO_4$ buffer and that iPPase reverses the effect of the added NaPPi.

The reactions contained: 100 mM Tricine pH 8.4, 10 mM $MgSO_4$, 0.1% Tergitol, 0.01% Mazu, 50 mg/mL thermostable luciferase (from *Photuris pennsylvanica* prepared as described in WO/9914336, published Mar. 25, 1999 which is incorporated by reference in its entirety), 200 mM ATP, 0.2% Prionex, 0.5 mM luciferin. All reactions contained either 200 mM non-inhibitory $KPO_4$ pH 7.4 or 200 mM inhibitory $KPO_4$ pH7.4. iPPase (Sigma 11891) was added to some of the reactions to a final concentration of 2 units/mL. Sodium pyrophosphate (NaPPi) was added to some reactions to a final concentration of 3 mM. The reactions were performed at room temperature. Luminescence was detected using a Berthold Orion Microplate Luminometer.

As shown in FIG. 15 inorganic pyrophosphatase was effective in reversing inhibition of luciferase when inhibitory $KPO_4$ buffer is used. Without being bound to a mechanism, the inventors observed that the addition of iPP to an otherwise active buffer can recreate an inhibitory buffer, and that the inhibition can be reversed by the addition of iPPase. These findings imply that the inhibitor is iPP.

Example 15

Cell-Based Luminescent CYP450 Assay

In this Example, a cell-based luminescent CYP450 assay is described. Inducers of CYP450 gene expression were evaluated for their effect on CYP450 activity. Primary hepatocytes from sexually mature male Sprague Dawley rats were obtained cryopreserved from Xenotech, LLC (Kansas City, Kans.). On the first day cells were thawed as recommended by the supplier and the percentage of live cells estimated by the method of trypan blue exclusion. Approximately $1.5 \times 10^5$ cells per $cm^2$ were seeded on collagen-coated 24-well tissue culture plates. Cells were cultured at 37° C., 95% relative humidity and 5% $CO_2$ in 0.3 mL/well HepatoZyme SFM medium supplemented with 2 mM L-glutamine and 1× penicillin-streptomycin (Life Technologies, Inc., Rockville, Md.). Initially cells were allowed to attach to plates for 6 hours then the medium was replaced with fresh medium supplemented to 0.25 mg/ml with Matrigel™ (BD Biosciences, Bedford, Mass.). Medium was changed daily.

On the third day after seeding of cells, culture medium was removed and replaced with 0.3 ml medium containing CYP450 gene inducers or their vehicle controls. On the fourth day medium was removed and replaced with fresh induction or vehicle control medium so that cells were exposed for 2 days.

On the fifth day induction and vehicle control media were replaced with fresh medium that contained luminogenic CYP450 substrates. At the end of the incubation period with luminogenic substrate, two types of luminescent assays were performed. Both assay formats were possible because the luminogenic substrates enter cells, likely by passive diffusion. The first type of assay is possible because the luciferin product of CYP450 reaction exits cells, again likely by passive diffusion. For the first type of assay a sample of medium was removed and combined with an equal volume of a luciferin detection reagent (200 mM tricine, pH 8.4, 100 micrograms/mL thermostable mutant of firefly luciferase from *Photuris pennsylvanica* (Ultra Glow™ luciferase, available from Promega, Corp.), 400 micromolar ATP, 20 mM $MgSO_4$ and 2% Tergitol) to initiate a luminescent reaction. For blank determinations for the first assay type luminogenic substrate was withheld from some wells but combined with an aliquot of medium after it was first combined with the luciferin detection reagent. For the second type of assay, an equal volume of luciferin detection reagent was added directly to the cell culture medium to stop CYP450 activity, produce a cell lysate and initiate a luminescent reaction. For blank determinations for the second reaction type luminogenic substrate was withheld from some wells but added to these wells after the luciferin detection reagent was first added. Aliquots of both types of reactions were transferred to white, opaque 96-well plates and luminescence was read on a Fluostar Optima luminometer (BMG, Inc.). Luminescence values from blank wells were subtracted from the values of corresponding wells. The results are shown in FIG. 16.

Example 16

Stabilization of Luminescent Signal Using Luciferase Inhibitors

In this Example, two luciferase competitive inhibitors, 2-amino-6-methylbenzothiazole (AMBT) or 2-(4-aminophenyl)-6-methylbenzothiazole (APMBT), were evaluated to determine their effect on stabilizing a luminescent signal.

50 microliter CYP1A1 reactions (0.5 μmol recombinant CYP1A1 enzyme, 30 μM Luciferin chloroethyl ether, 100 mM $KPO_4$, 1.3 mM $NADP^+$, 3.3 mM glucose-6-phosphate, 3.3 mM $MgCl_2$, 0.02 unit glucose-6-phosphate dehydrogenase) were incubated at 37° C. for 20 min. After the incubation, 50 microliters of a luciferin detection reagent (100 micrograms/mL thermostable luciferase (from *Photuris pennsylvanica*), 400 micromolar ATP, 0.6% Prionex, 2 units/mL iPPase, 200 mM Tricine pH 8.4, 20 mM $MgSO_4$, 2% Tergitol) containing either 100 micromolar APMBT, 100 micromolar AMBT, or no inhibitor were added to each CYP1A1 reaction. Luminescence was read immediately and at subsequent 5 minute intervals for 1 hour. The results are shown in FIG. 17.

Figure 17:
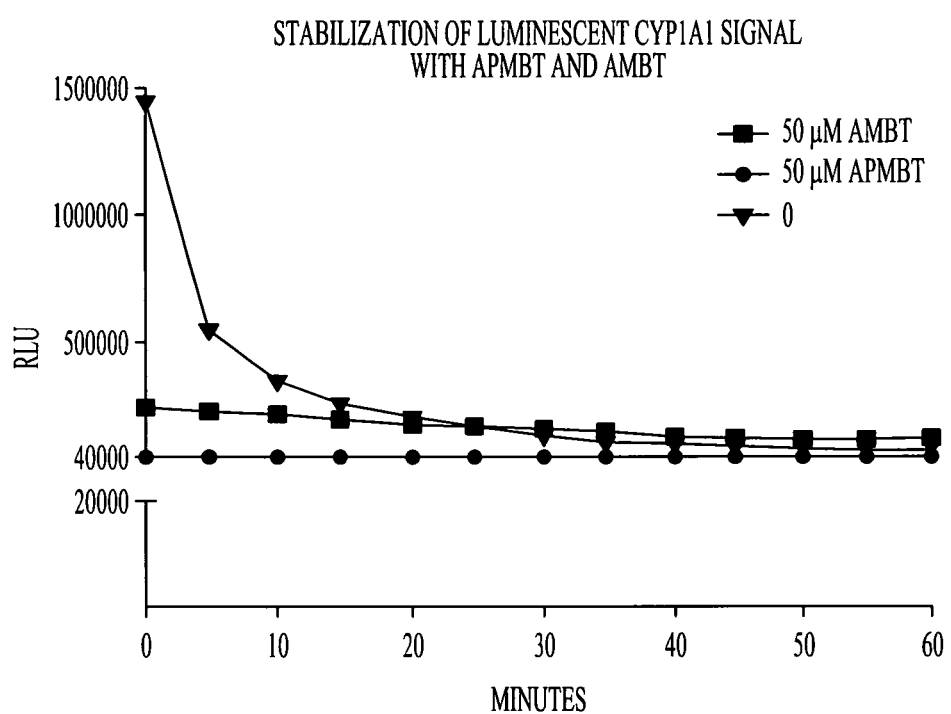
FIG. 17. Stabilization of luminescent signals using luciferase inhibitors. Inhibition of luciferase by an inhibitor 2-(4-aminophenyl)-6-methylbenzothiazole (APMBT) or 2-amino-6-methyl benzothiazole (AMBT) stabilizes the luminescent signal in a luminescent CYP450 assay. 50 microliter CYP1A1 reactions (0.5 μmol recombinant CYP1A1 enzyme, 30 μM Luciferin chloroethyl ether, 100 mM $KPO_4$, 1.3 mM $NADP^+$, 3.3 mM glucose-6-phosphate, 3.3 mM $MgCl_2$, 0.02 unit glucose-6-phosphate dehydrogenase) were incubated at 37° C. for 20 min. After the incubation, 50 microliters of a luciferin detection reagent (100 micrograms/mL thermostable luciferase (from *Photuris pennsylvanica*), 400 micromolar ATP, 0.6% Prionex, 2 units/mL iPPase, 200 mM Tricine pH 8.4, 20 mM $MgSO_4$, 2% Tergitol) containing either 100 micromolar APMBT, 100 micromolar AMBT, or no inhibitor were added to each aliquot of CYP1A1 reaction. Luminescence was read immediately and at subsequent 5 minute intervals for 1 hour.

As shown in FIG. 17, inhibition of luciferase by an inhibitor such as 2-(4-aminophenyl)-6-methylbenzothiazole (APMBT) or 2-amino-6-methyl benzothiazole (AMBT) stabilizes the luminescent signal in a luminescent CYP450 assay.

While the present invention has now been described and exemplified with some specificity, those skilled in the art will appreciate the various modifications, including variations, additions and omissions, that may be made in what has been disclosed herein without departing from the spirit of the invention. Accordingly, it is intended that these modifications also be encompassed by the present invention and that the scope of the present invention be limited solely by the broadest interpretation that lawfully can be accorded the appended claims.

REFERENCES

1. Black, S. D. and Coon, M. J. (1987) "P450 cytochromes: structure and function", *Adv. Enzymol. Relat. Areas Mol Biol*, 60, 35-87.
2. Phillips, I. R. and Shephard, E. A. eds. (1998) "Cytochrome P450 protocols", *Methods in Mol. Biol.*, 107, v-vi.
3. Nelson, D. R. et at (1996) "P450 superfamily: update on new sequences, gene mappin, accession numbers and nomenclature", *Pharmacogenetics*, 6, 1-42.
4. Wrighton, S. A. and Stevens, J. C. (1992) "The human hepatic cytochromes P450 involved in drug metabolism", *Critical Reviews in Toxicology*, 22 (1), 1-21.
5. Flickinger, B. (2001) "Using metabolism data in early development", *Drug Disc. Dev.*, 4 (9), 53-56.
6. Miller, V. P. et al (2000) "Fluorometric high-throughput screening for inhibitors of Cytochrome P450", *Ann. NY Acad. Sci*, 919, 26-32.
7. Makings, L. R. and Zlokarnik, G. (2000) "Optical molecular sensors for Cytochrome P450 activity", U.S. Pat. No. 6,143,492.
8. Hardman, J. G. et al (eds.) *The Pharmacological Basis of Therapeutics*, 9th ed., pp. 1-27, McGraw-Hill, 1996.
9. Guengerich, F. P. (2001) "Common and uncommon cytochrome P450 reactions related to metabolism and chemical toxicity", *Chem. Res. Tox.*, 14(6), 611-650.
10. Tassaneeyakul, W. et al (1993) "Specificity of substrate and inhibitor probes for human cytochromes P450 1A1 and 1A2", *J. Pharmacol. Exp. Ther.* 265 (1), 401-407.
11. Rahman, A. et al (1994) "Selective biotransformation of taxol to 6 alpha-hydroxytaxol by human cytochrome P450 2C8", *Cancer Res.* 54 (21), 5543-5546.
12. Leemann, T. et al (1993) "Cytochrome P450TB (CYP2C): a major monooxygenase catalyzing diclofenac 4'-hydroxylation in human liver", *Life Sci.* 52 (1), 29-34.
13. Sai, Y. et al (2000) "Assessment of specificity of eight chemical inhibitors using cDNA-expressed Cytochrome P450", *Xenobiotica* 30 (4), 327-343.
14. Yun, C-H, et al (2000) "Rate-determining steps in phenacetin oxidations by human Cytochrome P450 1A2 and selected mutants", *Biochemistry* 39, 11319-11329.
15. Miller, V. P. et al (2000) "Fluorometric high-throughput screening for inhibitors of cytochrome P450", *Ann. N.Y. Acad. Sci.* 919, 26-32.
16. Shou, M. et al (2001) "A kinetic model for the metabolic interaction of two substrates at the active site of cytochrome P450 3A4", *J. Biol. Chem.* 276 (3), 2256-2262.
17. International publication WO 01/20002 (Promega Corp.).
18. Graham-Lorence, S. and J. A. Peterson, "P450s: Structural similarities and functional differences," FASEB J., 10:206-214 (1996).
19. Prosite: PDOC00081 Cytochrome P450 cysteine heme-iron ligand signature (November, 1997).
20. This compound was prepared from phenylglyoxal aldoxime[21] and 1-cyano-2-phenyl-ethylamine hydrochloride[22] according to the procedure described by Kishi, Y. et al. Tetrahedron Letters, No. 27, pp 2747-2748, 1972.
21. This compound was prepared from acetophenone according to the procedure described by Usami, K. et al. Tetrahedron, Vol 52, No. 37, pp 12061-12090, 1996.
22. This compound was prepared from phenylacetaldehyde according to the procedure described by Hirano, T. et al. Tetrahedron, Vol 53, No. 38, pp 12903-12916, 1997.

What is claimed is:
1. The compound having the structure

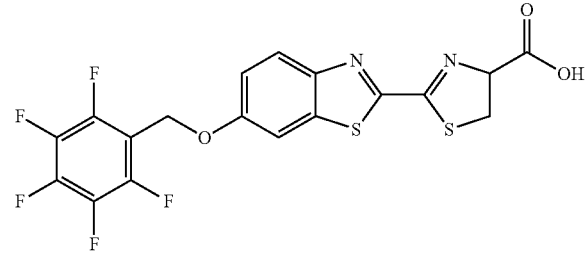 [SMILES: O=C(O)C1CSC(c2nc3ccc(OCc4c(F)c(F)c(F)c(F)c4F)cc3s2)=N1]

or a salt thereof.

2. A composition comprising a compound of claim 1 and an aqueous carrier.

3. The composition of claim 2, further comprising a pyrophosphatase.

4. The composition of claim 3 wherein the pyrophosphatase is an inorganic pyrophosphatase.

* * * * *